(12) United States Patent
Hurley et al.

(10) Patent No.: US 6,528,517 B1
(45) Date of Patent: Mar. 4, 2003

(54) SYNTHESIS OF QUINOBENZOXAZINE ANALOGUES WITH TOPOISOMERASE II AND QUADRUPLEX INTERACTIONS FOR USE AS ANTINEOPLASTIC AGENTS

(75) Inventors: Laurence H. Hurley, Austin, TX (US); Qingping Zeng, Ballwin, MO (US); Yan Kwok, Sunnyvale, CA (US); Jongsik Gam, Austin, TX (US); Sean M. Kerwin, Round Rock, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/245,019

(22) Filed: Feb. 4, 1999

Related U.S. Application Data
(60) Provisional application No. 60/073,658, filed on Feb. 4, 1998.

(51) Int. Cl.[7] .......................... A61K 31/44; A61K 31/54
(52) U.S. Cl. ................. 514/279; 514/224.5; 514/253.08
(58) Field of Search .............................. 514/253.08, 12, 514/29, 227.8, 230.2, 279, 224.5, 312, 152, 195, 209, 23, 450, 37

(56) References Cited

U.S. PATENT DOCUMENTS
5,308,843 A * 5/1994 Coughlin et al.
5,476,854 A * 12/1995 Young et al.
5,624,924 A    4/1997 Chu et al.

OTHER PUBLICATIONS

Chen et al., "XB596, A Promising Bis–Naphthalimide Anti––Cancer Agent," *Anti–Cancer Drugs*, 4(4), 447–457, Aug. 1993.

Chu and Maleczka Jr., "Synthetis of 4–0xo–4H–quino[2,3, 4–Ij][1,4]–benoxazine–5–carboxylic acid derivatives," *J. Heterocyclic Chem.*, 24:453–456, 1987.

Chu et al., "Synthesis and antitumour activities of quinolone antineoplastic agents," *Drugs Exptl. Clin. Res.*, 18:275–282, 1992.

Chu et al., "Synthesis and antitumour activities of tetracyclic quinolone antineoplastic agents," *Drugs Exptl. Clin. Res.*, 20:177–183, 1994.

Clement et al., "Biological characterization of a novel antitumour quinolone," *Cancer Res.*, 55:830–835, 1995.

Fan et al., "Self-assembly of a quinobenzoxazine–$^{Mg2+}$ complex on DNA: a new paradigm for the structure of a drug–DNA complex and implications for the structure of the quinolone bacterial gyrase–DNA complex," *J. Med. Chem.*, 38:408–424, 1995.

Fedoroff et al., "NMR–based model of a telomerase–inhibiting compound bound to g–quadruplex DNA," *Biochemistry*, 37:12367–12374, 1998.

Han et al., "A DNA polymerase stop assay for Q–quadruplex–interactive compounds," *Nucelic Acids Research*, 27(2):537–542, 1999.

Hansen et al., "Molecular details of the structure of a psorospermin–DNA covalent/intercalation complex and associated DNA sequence selectivity," *J. Am. Chem. Soc.*, 118:5553–5561, 1996.

Henderson et al., "Telomere G–strand structure and function analyzed by chemical protection, base analogue substitution, and utilization by telomerse in vitro," *Biochemistry*, 29:732–737, 1990.

Kwok et al., "Topoisomerase II–mediated site–directed alkylation of DNA by psorospermin and its use in mapping other topoisomerase II poison binding sites," *Proc. Natl. Acad. Sci. U.S.A.*, 95:13531–13536, 1998.

Kwok and Hurley, "Topoisomerase II site–directed alkylation of DNA by psorospermin and its effect on topoisomerase II–mediated DNA cleavage," *J. Biol. Chem.*, 49:33020–33026, 1998.

Kwok et al., "Structural insight into a quinolone–topoisomerase II–DNA complex," *The J. of Bio. Chem.*, 274:1–10, 1999.

Liu, "DNA topoisomerase poisons as antitumor drugs," *Annu. Rev. Biochem.*, 58:351–375, 1989.

MacDonald et al., "A solid phase approach to quinolones using the Diversomer® technology," *Tetrahedron Lett.*, 37:4815–4818, 1996.

Maxam and Gilbert, "Sequencing end–labeled DNA with base–specific chemical cleavages," *Methods Enzymol.*, 65:499–560, 1980.

Mergny and Hélène, "G–quadruplex DNA: a target for drug design," *Nature Medicine*, 4:1366–1367, 1998.

Mitscher et al., "Structure–activity relationships of fluoro–4–quinolones," Springer–Verlag: New York, 1990, pp. 115–146.

Morin, "Is telomerase a universal cancer target?" *J. Natl. Cancer Inst.*, 87:859–861, 1995.

Mosmann, "Rapid colorimetric assay for cellular growth and survival: application to proliferation and cytotoxicity assays," *J. Immunol. Methods*, 65(1–2):55–63, 1983.

Parkinson, "Do telomerase antagonists represent a novel anti–cancer strategy?" *Br. J. Cancer*, 73:1–4, 1996.

(List continued on next page.)

Primary Examiner—Sean McGarry
Assistant Examiner—Janet Epps
(74) Attorney, Agent, or Firm—Fulbright & Jaworski L.L.P.

(57) ABSTRACT

The present invention discloses a novel quinobenzoxazine self-assembly complex on DNA and on the topoisomerase II-DNA complex. The related model is used to design a new series of quinobenzoxazines, pyridobenzophenoxazines, pyrridonaphthophenoxazines, and other related compounds that may exhibit anticancer or antibiotic activity. The anti-cancer activity of these compounds is thought to operate via stabilization of the topoisomerase II-DNA complex and/or interaction with G-quadruplexes, while the antibiotic activity of these compounds derives from their ability to inhibit gyrase, the bacterial type II topoisomerase.

20 Claims, 22 Drawing Sheets

OTHER PUBLICATIONS

Figure 1A:
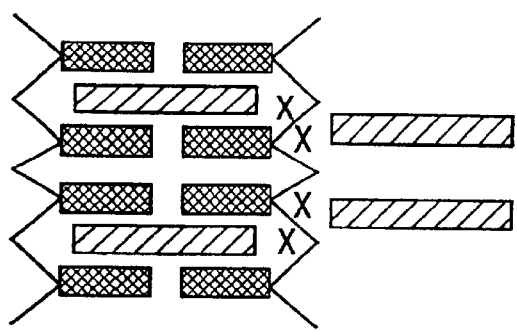

Rádl and Zikán, "Synthesis and antimicrobial activity of some 3-OXO-3H-pyrido[3,2,1-kl] phenoxazine-2-carboxylic acids," *Collect. Czech. Chem. Commun.*, 54:506–515, 1989.

Permana et al., "Quinobenoxazines: a class of novel antitumor quinolones and potent mammalian DNA topoisomerase II catalytic inhibitors," *Biochemistry*, 33:11333–11339, 1994.

Raymond et al., "Agents that target telomerase and telomeres," *Curr. Opinion Biotch.*, 7:583–591, 1996.

Rodi et al., "Screening of a library of phage–displayed peptides identifies human Bcl–2 as a taxol–binding protein," *J. Mol. Biol.*, 285:197, 1999.

Rubinstein et al., "Comparison of in vitro anticancer–drug–screening data generated with a tetrazolium assay versus a protein assay against a diverse panel for human tumor cell lines," *J. Natl. Cancer Inst.*, 82(13):1113–1118, 1990.

Shen et al., "Mechanism of inhibition of DNA gyrase by quinolone antibacterials: specificity and cooperativity of drug binding to DNA," *Biochemistry*, 28:3879–3885, 1989a.

Shen et al., "Mechanism of quinolone inhibition of DNA gyrase," *J. Biol. Chem.*, 264:2973–2978, 1989b.

Shen et al., "Mechanism of inhibition of DNA gyrase by quinlone antibacterials: a cooperative drug–DNA binding model," *Biochemistry*, 28:3886–3894, 1989c.

Sun et al., "Inhibition of human telomerase by a g–quadruplex–interactive compound," *J. Med. Chem.*, 40:2113–2116, 1997.

Wang and Patel, "Solution structure of the human telomeric repeat d[AG$_3$(T$_2$AG$_3$)$_3$] g–tetraplex," *Structure*, 1:263–282, 1993.

Weitzmann et al., "The development and use of a DNA polymerase arrest assay for the evaluation of parameters affecting intrastrand tetraplex formation," *J. Biol. Chem.*, 271:20958–20964, 1996.

Wheelhouse et al., "Cationic porphyrins as telomerase inhibitors: the interaciton of tetra–(N–methyl–4–pyridyl)porphine with Quadruplex DNA," *J. Am. Chem. Soc.*, 120:3261–3262, 1998.

Willmott and Maxwell, "A single point mutation in the DNA gyrase a protein greatly reduces binding of fluoroquinolones to the gyrase–DNA complex," *Anitmicrob. Agents Chemother.*, 37:126–127, 1993.

Yu et al., "Evidence of the formation of 2:2 drug–Mg$^{2+}$ dimers in solution and for the formation of dimeric drug complexes on DNA form the DNA–accelerated photochemical reaction of antineoplastic quinobenzoxazines," *J. Am. Chem. Soc.*, 118:7040–7048, 1996.

Zeng et al., "Design of new topoisomerase II inhibitors based upon a quinobenzoxazine self–assembly model," *J. Med. Chem.*, 41:4273–4278, 1998.

Zeng et al., "Design of new topoisomerase II inhibitors based upon a quinobenzoxazine self–assembly model," *J. Med. Chem.*, 41:4273–4278, 1998.

Yamakuchi et al., "New quinolones, ofloxacin and levofloxain, inhibit telomerase activity in transitional cell carcinoma cell lines,"Abstract, *Cancer Letters*, 119(2):213–219, 1997.

Kaufmann and Hancock, "Topoisomerase II as a target for anticancer chemtherapy," Abstract, *Acta Bicochimica Polonica*, 42(4):381–393, 1995.

Ebisuno et al., "The cytotoxic effects of fleroxacin and ciprofloxacin on transitional cell carcinoma in vitro," *Cancer*, 80(12):2263–2267, 1997.

Wentland et al., "Mammalian topoisomerase II inhibitory activity of 1–cyclopropyl–6,8–difluro–1,4–dihydro–7–(2, 6–dimethyl–4–pyridinyl)–4–oxo–3–quinolinecarboxylic acid and related derivatives," *J. Med. Chem.*, 36:2801–2809, 1993.

Hertzberg et al., "Antineoplastic agents," *Ann. Rep. In Med. Chem.*, 28:167–176, 1993.

Palmer et al., "Potential antitumor agents. 54. Chromophore requirements for in vivo antitumor activity among the general class of linear tricyclic carbonxamides," *J. Med. Chem.*, 31:707–712, 1988.

Hsiung et al., "A mutation in yeast TOP2 homologous to a quinolone–resistant mutation in bacteria," *The J. of Biol. Chem.*, 270(35):20359–20364, 1995.

Khac and Moreau, "Interaction between fluoroquinolones, Mg$^{2+}$, DNA and DNA gyrase, studied by phase partitioning in an aqueous two–phase system and by affinity chromatography," *J. of Chromatography*, 668:241–247, 1994.

Chung et al., "p–Quinone methides as geometric analogues of quinolone carboxylate antibacterials," *Bioorganic & Medicinal Chem. Letters*, 6(12):1309–1312, 1996.

Lecomte et al., "NMR investigation of pefloxacin–cation–DNA interactions: the essential role of Mg$^{2+}$," *Intl. J. of Pharm.*, 164:57–65, 1998.

Rodighiero et al., "Angular furoquinolones, psoralen analogs: novel antiproliferative agents for skin diseases. Synthesis, biological activity, mechanism of action, and computer–aided studies," *J. Med. Chem.*, 39:1293–1302, 1996.

Llorente et al., "Using SAR and QSAR analysis to model the activity and structure fo the quinolone–DNA complex," *Bioorganic & Medicinal Chem.*, 4(1):61–71, 1996.

Lecomte and Chenon, "NMR investigation of pefloxacin/cation/DNA interactions. Mg$^{2+}$ and Ca$^{2+}$ binding," *Intl. J. of Pharm.*, 139:105–112, 1996.

Lecomte et al., "Effect of magnesium complexation by fluoroquinolones on their antibacterial properties," *Antimicrobial Agents and Chemo.*, 38(12):2810–2816, 1994.

Khac and Moreau, "Interactions between fluoroquinolones, Mg$^{2+}$, DNA and DNA gyrase, studied by phase partitioning in an aqueous two–phase system and by affinity chromotagraphy," *J. of Chromatography*, 668:241–247, 1994.

\* cited by examiner (A-62176)

(Norfloxacin)

Teoc= -CO₂CH₂CH₂Si(CH₃)₂
t-Boc= -CO₂C(CH₃)₃
TFA= trifluoroacetic acid

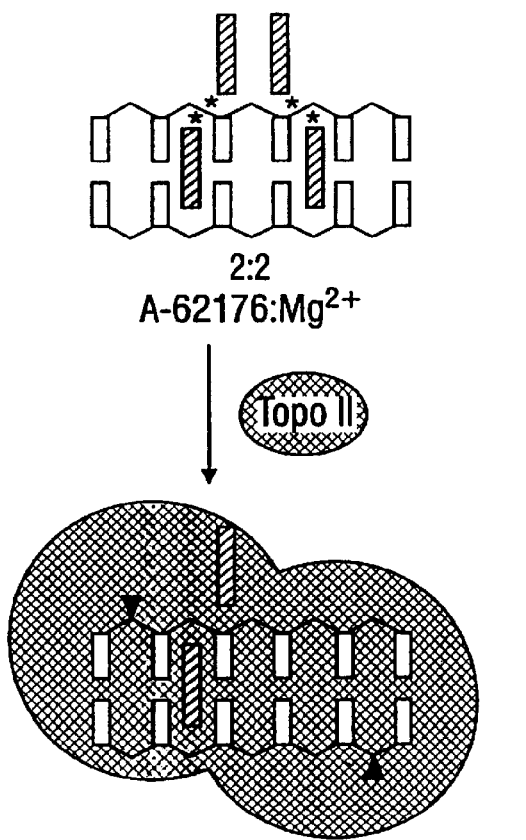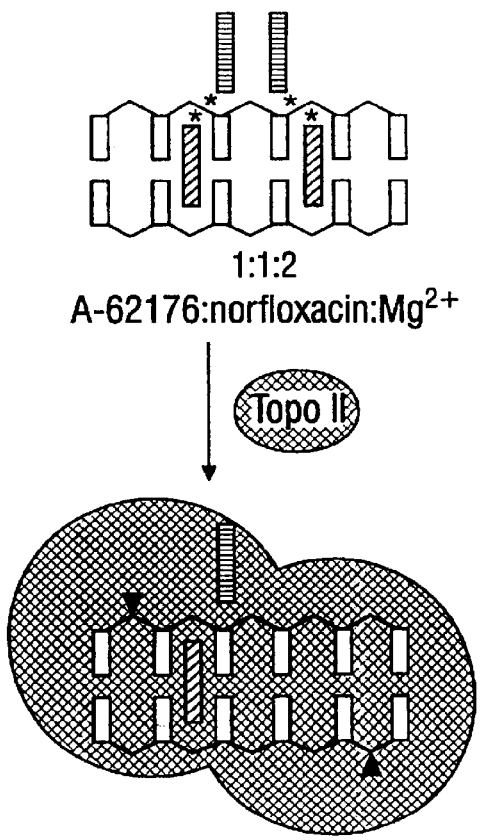
FIG. 10A
FIG. 10B

SYNTHESIS OF QUINOBENZOXAZINE ANALOGUES WITH TOPOISOMERASE II AND QUADRUPLEX INTERACTIONS FOR USE AS ANTINEOPLASTIC AGENTS

This application claims priority to and specifically incorporates by reference, the content of U.S. Provisional Application Serial No. 60/073,658, filed Feb. 4, 1998.

The government may have rights in the present invention pursuant to grant number CA-49751 from the National Cancer Institute.

1.0 BACKGROUND OF THE INVENTION

1. Field of the Invention

The present invention relates generally to novel quinobenzoxazines, methods of synthesis, and uses thereof. More particularly, it concerns the synthesis of quinobenzoxazine compounds, pyridobenzophenoxazines, pyrridonaphthophenoxazines, and other related compounds that can stabilize the topoisomerase II-DNA complex and interact with G-quadruplex DNA and that, as a consequence, exhibit anticancer and antibiotic activity.

2. Description of Related Art

There remains a persistent need for new compounds with antibiotic properties. Over time bacterial agents evolve to develop resistance to existing classes of antibiotics, thus driving the continual need for new and effective antibiotics. The development of new classes of compounds with both narrow and broad spectrum antibacterial properties is therefore desired.

Similarly, there also has been a need for, and much research focused on, the treatment of cancer using chemotherapies. Resources continue to be directed toward the development of antineoplastic agents for the treatment of cancers, including solid tumors, leukemias, and other forms of cancer. Many antineoplastic agents developed are not ideal because of problems associated with their cytotoxicity and multidrug resistance of some cancers. What is needed are compositions for the treatment of cancers that are effective while minimizing their adverse effects.

The cytotoxicity of the fluoroquinolones is due to their ability to shift the cleavage-religation equilibrium required for topoisomerase action toward cleavage, thereby effectively trapping the enzyme on DNA to form the "cleaved complex" (Shen et al., 1989a; Shen et al., 1989b; Shen et al., 1989c; Willmott and Maxwell, 1993). The quinobenzoxazines are potent mammalian DNA topoisomerase II inhibitors. It has been proposed that the quinobenzoxazines inhibit DNA topoisomerase II reaction at a step prior to the formation of the "cleaved complex" intermediate (Permana et al., 1994).

The quinobenzoxazines are synthetic analogues of antibacterial fluoroquinolones (Chu and Maleczka, Jr., 1987; Chu et al., 1992; Chu et al., 1994). Studies have shown that some quinobenzoxazine derivatives have curative activity against solid tumors, murine tumors, and human xenographs (Clement et al., 1995). The antineoplastic effects of related compounds, the quinobenzothiazines, are detailed in U.S. Pat. No. 5,624,924, and is incorporated herin by reference. DNA binding studies reveal that antibacterial fluoroquinolones prefer to bind single-stranded DNA to duplex DNA or bind the DNA-gyrase complex in the presence of $Mg^{2+}$ (Willmott and Maxwell, 1993). In contrast, the quinobenzoxazines bind duplex DNA through intercalation. A drug self-assembly model has been proposed for the quinobenzoxazines based on results of biophysical and biochemical studies (Fan et al., 1995; Yu et al., 1996). In this model, a 2:2 drug:$Mg^{2+}$ dimer binds DNA with one drug molecule intercalating between DNA base pairs and the other drug molecule externally bound through two chelated $Mg^{2+}$ ions. The two magnesium cations link the two drug molecules in a head-to-tail fashion in which the β-ketoacid moiety is the bidentate ligand as a head and the primary amino group of the amino-pyrrolidine side chain is the tail. Each magnesium cation also binds with one phosphate oxygen of DNA backbone and two water molecules to form an octahedral complex.

The model interacts with DNA as follows: the polyaromatic ring of one moiety intercalates into DNA base pairs and anchors the whole assembly on DNA; and the β-ketoacid functionality and the 3-amino-pyrrolidine substituent of the second moiety chelate $Mg^{2+}$ through which the external molecule is bound in the DNA minor groove. In this manner, one quinobenzoxazine molecule serves as a DNA intercalator and the other quinobenzoxazine molecule binds externally, held to the first drug molecule by two $Mg^{2+}$ ions (Fan et al., 1995). On the basis of this model, new combinations of antibacterials and anticancer agents can be designed that target the bacterial gyrase-DNA and topoisomerase II-DNA complexes, respectively. In each case, one molecule designed to optimally interact with the DNA by intercalation, and the other designed to interact with the enzyme by external interaction with the DNA, are predicted to produce greater efficacy than the same molecule serving both roles in a suboptimum manner. G-quadruplexes also have been proposed as molecular targets for anticancer agents (Mergny and Héléne, 1998). Drug interaction with G-quadruplexes leads to inhibition of telomerase (Sun et al., 1997; Wheelhouse et al., 1998; Fedoroff et al., 1998). Inhibition of telomerase has been proposed as a selective way to kill cancer cells because in large part only cancer cells depend upon telomerase for survival (Morin, 1995; Parkinson, 1996; Raymond et al., 1996).

Single agents that have dual mechanisms of action are proposed to have an advantage over agents that only have one defined mechanism of action. For example, studies have shown that Taxol not only targets tubulin, but also interacts with bcl-2 (Rodi, 1999). This may account for some of the efficacy of Taxol in its anticancer activity.

2.0 SUMMARY OF THE INVENTION

The present invention provides a new and novel solid- and solution-state parallel synthesis method for quinobenzoxazine analogues, a novel model of quinobenzoxazine self-assembling on DNA, and use of this model to design a series of new quinobenzoxazines, pyridobenzophenoxazines, pyrridonaphthophenoxazines and other related compounds that exhibit anticancer or antibiotic activity. The anticancer activity of these novel compounds is thought to operate via stabilization of the topoisomerase II-DNA complex and/or interaction with G-quadruplexes. The antibiotic activity of these compounds derives from their ability to interact with the gyrase-DNA complex, which is the bacterial type II topoisomerase.

The present invention therefore seeks to overcome deficiencies in the prior art by providing a new model for design and a new method for the synthesis, of a new series of quinobenzoxazines that display increased anticancer and antibiotic activities. One aspect of the invention includes a novel dimer model compound for use in developing quinobenzoxazines with potentiated anticancer and antibiotic activity. Further provided is a solid-state parallel synthesis method of producing these antineoplastic quinobenzoxazines and quinobenzoxazine derivatives.

The present invention contemplates a 2:2 quinobenzoxazine:$Mg^{2+}$ dimer model. This dimer binds DNA with one drug molecule intercalating between DNA base pairs and the other drug molecule externally binds through two chelated $Mg^{2+}$ ions. The magnesium cations link two drug molecules in a head-to-tail fashion in which the β-ketoacid moiety is the bidentate ligand as a head and the primary amino group of the amino pyrrolidine side chain is the tail. Each magnesium cation also binds with a single phosphate oxygen of the DNA backbone and two water molecules to form an octahedral complex. In this manner, one quinobenzoxazine molecule of the dimer serves as a DNA intercalator and the other quinobenzoxazine molecule binds externally, held to the first drug molecule by two $Mg^{2+}$ ions.

Alternatively, the 2:2 quinobenzoxazine:$Mg^{2+}$ dimer model utilizes a heterodimer. Based on the fact that fluoroquinolones, parent compounds to quinobenzoxazines, in the presence of quinobenzoxazines, can cooperatively interact with DNA in the presence of magnesium and have a cooperative effect on the lengthening of the DNA helix, a heterodimer model was made. The heterodimer is constructed by removal of the externally bound quinobenzoxazine molecule and substituting the nonintercalating fluoroquinolone parent molecule. The intercalating aspect of the dimer model remains a quinobenzoxazine. Upon addition of the nonintercalating fluoroquinolone to the quinobenzoxazine, a cooperative effect on DNA lengthening is observed that is consistent with the substitution of the externally bound quinobenzoxazine by the nonintercalating fluoroquinolone. This result provides useful information in that it reveals that both the intercalating and the externally bound moieties, as well as the $Mg^{2+}$ binding ability, of the quinobenzoxazine are useful in the design and synthesis of novel quinobenzoxazines with potentiated anticancer and antibiotic activity. Furthermore, the inventors demonstrate that this heterodimer model also exists in the presence of topoisomerase II bound to DNA. In an in vitro study using a prostate cancer cell line, it was found that addition of the nonintercalating fluoroquinolone Norfloxacin increased the potency of the quinobenzoxazine up to 20-fold, providing additional evidence for the 2:2 quinobenzoxazine:$Mg^{2+}$ dimer model.

In addition to topoisomerase II as a molecular target, some of the quinobenzoxazines interact with G-quadruplexes. As a result of G-quadruplex interaction, these compounds inhibit telomerase and cause chromosomal aberrations. Thus, in this present invention there are three categories of anticancer drugs. The first two groups of compounds are those that are either topoisomerase II interactive or G-quadruplex interactive, while the third group can interact with both targets.

The present invention further provides a novel method of solid-based parallel synthesis of quinobenzoxazines. The first step is the loading of a quinobenzoxazine precursor onto a solid support to provide a solid bound ester. A variety of solid supports may be utilized. Virtually any solid support that is capable of binding to a precursor to form a solid bound ester through a transesterification reaction is acceptable so long as the solid support is compatible with the protective groups used during peptide synthesis. These protective groups include Fmoc, t-Boc, and Teoc. The protective groups may be readily removed using conditions suitable for the particular group employed. For example, Fmoc is removed under basic conditions, t-Boc is removed under acidic conditions, and Teoc is removed in the presence of fluoride ion. Thus, for an acceptable solid support to work with the instant invention, it must contain properties that allow the growing peptide chains to be protected or deprotected as desired under appropriate conditions. In a preferred embodiment, a Wang resin is used as a solid support to which the precursor is bound by a transesterification reaction in the presence of a catalyst. Generally, any carboxyacetophenone containing fluorine atoms or nitro groups on the two and three positions of the benzene ring may be employed. These compounds may be modified using combinatorial chemistry techniques to produce a tetracyclic quinobenzoxazine scaffolding, which also can undergo a transesterification reaction to bind to the resin or other solid support. A preferred precursor is ethyl 2,3,4,5-tetrafluorobenzoacetate.

The next step in the disclosed solid-state synthesis comprises a generation of enaminoketoester from the solid bound ester formed during the transesterification reaction outlined above. This is considered a branch point from which diversified scaffolding can be made.

The invention thus provides for the formation of a tetracyclic scaffolding via a double cyclization step from the enaminoketoester. In a preferred embodiment, the organic base is tetramethylguanidine (TMG).

After formation of the scaffolding, the fluorine at the 7 position may be substituted by a nucleophilic (for example, a nitrogeneous base), thereby generating any of a wide variety of quinobenzoxazine analogues.

Once the quinobenzoxazine analogues have been formed by regio-specific substitution of the fluorine further derivatization may be accomplished by deprotection of the benzylic amino groups and subsequent coupling with an amino acid, acylating agent, or alkylating agent. The coupling agents are selected on the basis of their potential to exhibit increased DNA unwinding and DNA binding properties as compared with the parent quinobenzoxazines. One may select for these properties by first testing candidates in the dimer model previously discussed. It is demonstrated that benzo-annulated quinobenzoxazines will exhibit enhanced DNA binding and/or increased DNA unwinding compared with quinobenzoxazines.

Once a desired compound is synthesized by the disclosed method, the final step of the solid-state synthesis method is to cleave the compounds from the solid support.

The invention further provides novel quinobenzoxazines and quinobenzoxazine analogues. These molecules may be designed by use of the dimer model described and synthesized by the solid-state synthesis method disclosed herein.

It is understood that any benzo-annulated quinobenzoxazine, or any quinobenzoxazine containing a quinobenzoxazine with increased DNA binding or unwinding capacities, is encompassed by the instant invention. Particularly useful compounds are those with benzo-annulated ring systems and extended side chains.

3.0 BRIEF DESCRIPTION OF THE DRAWINGS

The following drawings form part of the present specification and are included to further demonstrate certain aspects of the present invention. The invention may be better understood by reference to one or more of these drawings in combination with the detailed descriptions of specific embodiments presented herein.

Figures 1, 4A:
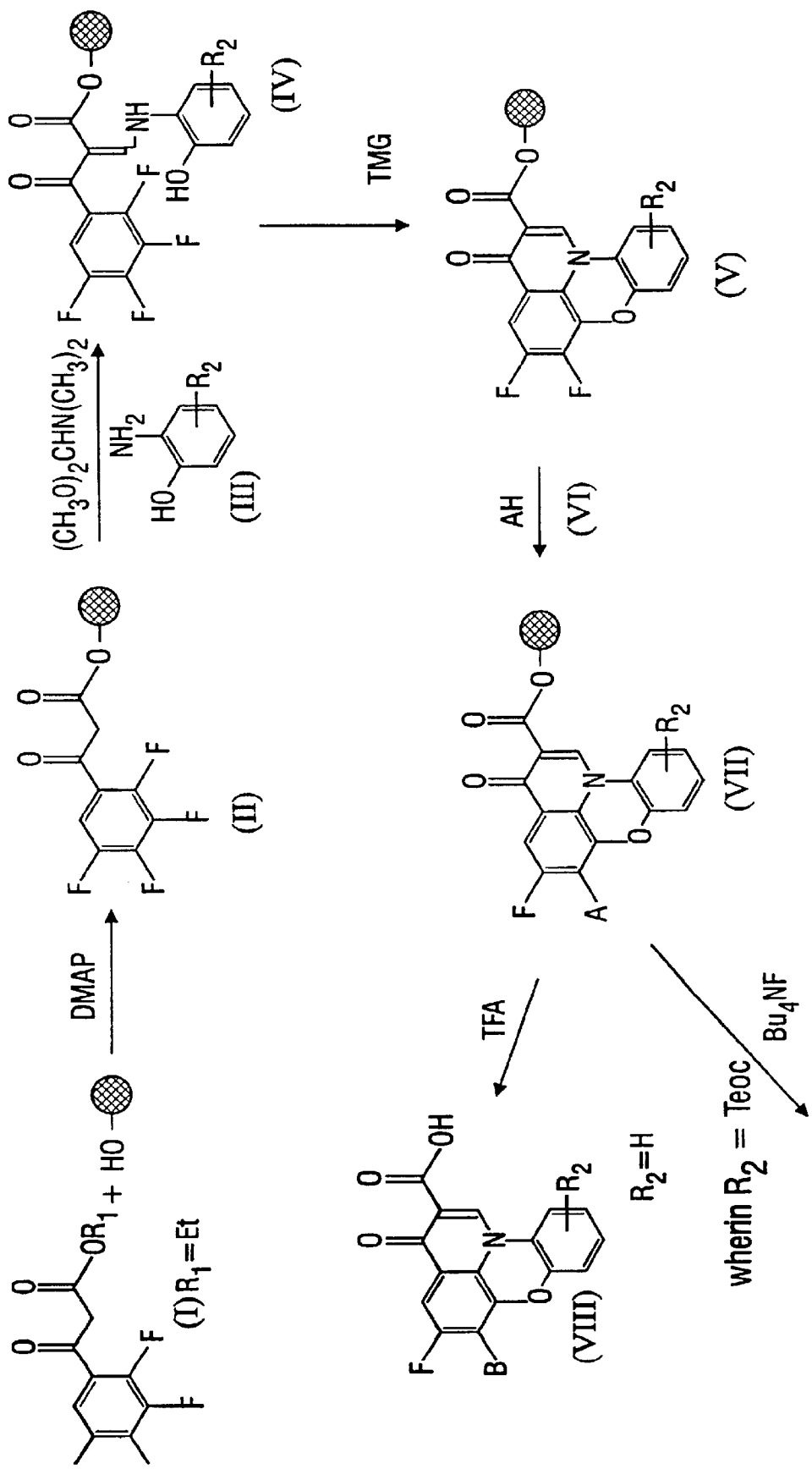

FIGS. 1, A–B. Self-assembly model for the quinobenzoxazines on DNA. (A) Both intercalating and externally bound molecules are A-62176. (B) The intercalating molecule is A-62176 and the externally bound molecule is Norfloxacin. Hatched bars=quinobenzoxazine, open bars=Norfloxacin, and x=$Mg^{2+}$.

Figures 2, 4A:
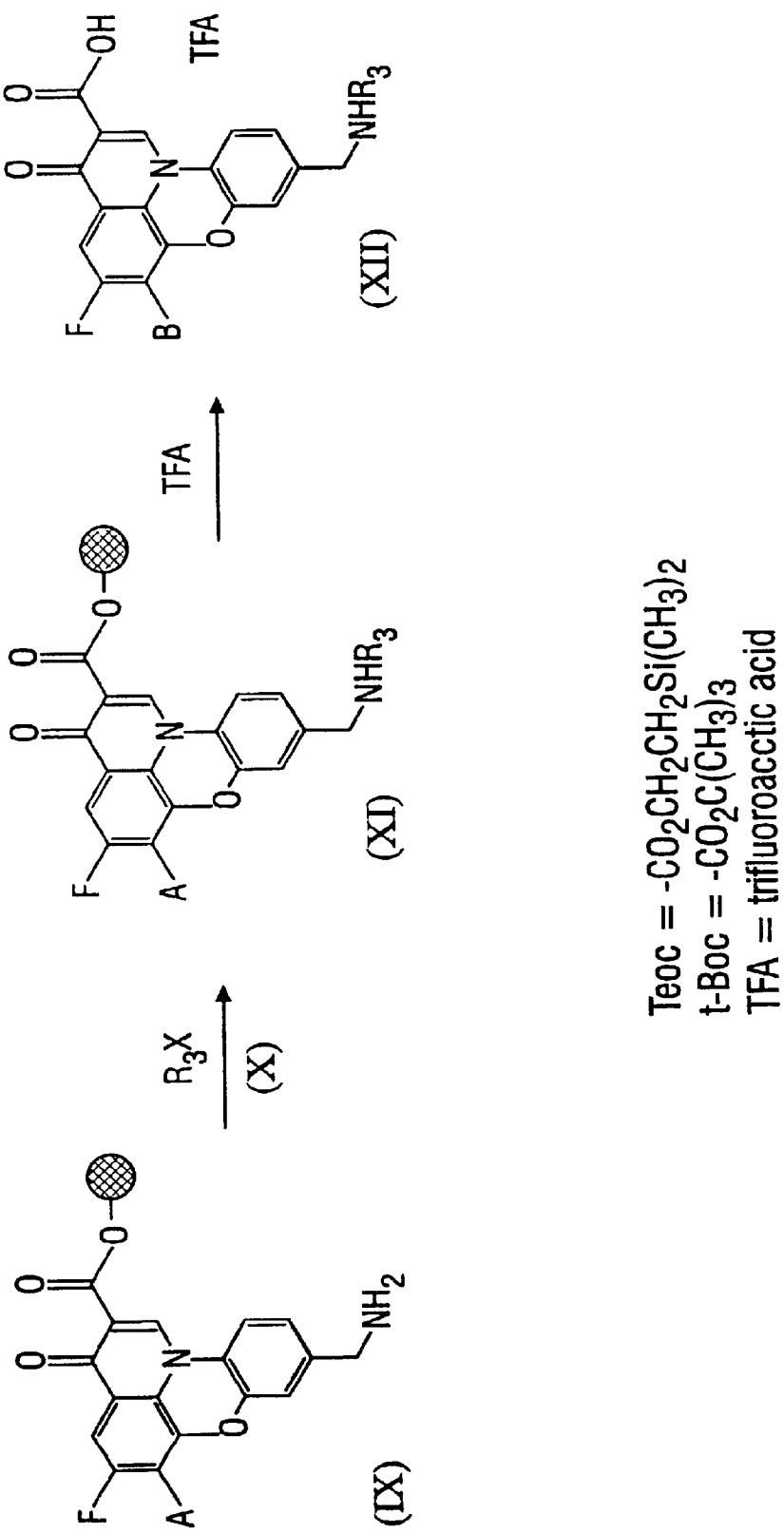

FIG. 2. Structures of select topo II-DNA-interactive compounds

Figure 9A:
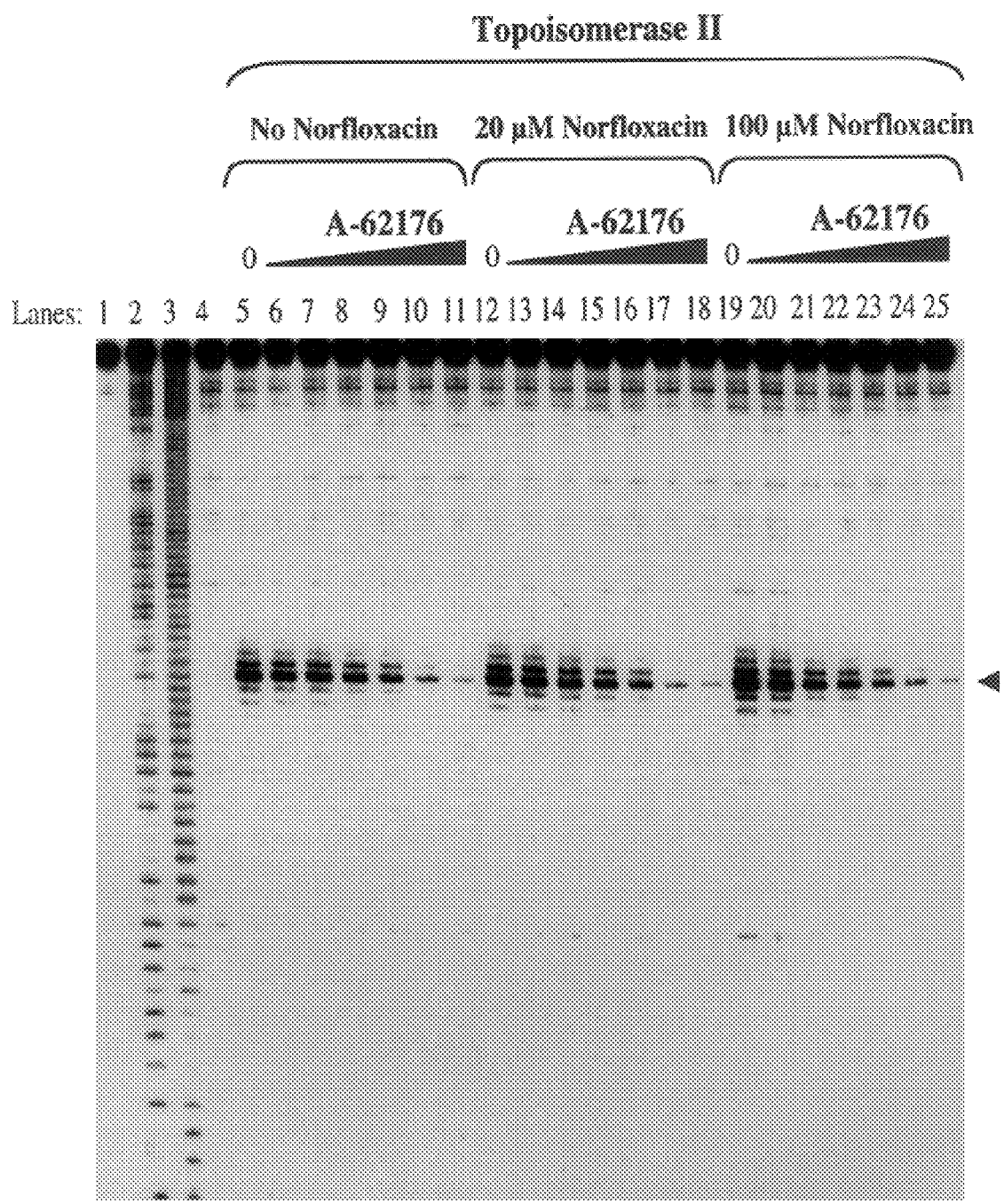
Figures 1, 9B:
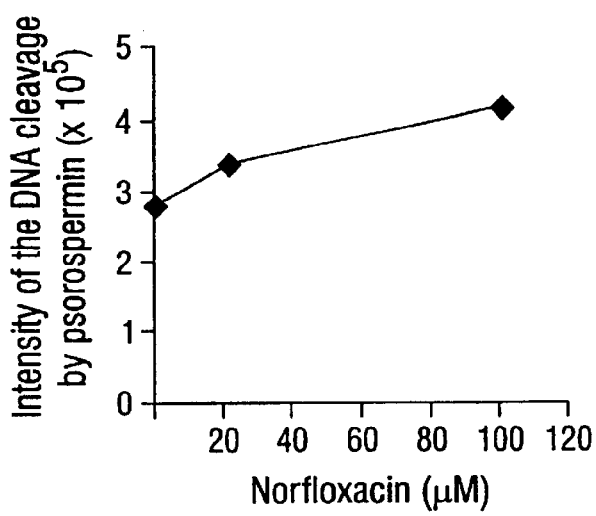
Figures 2, 9B:
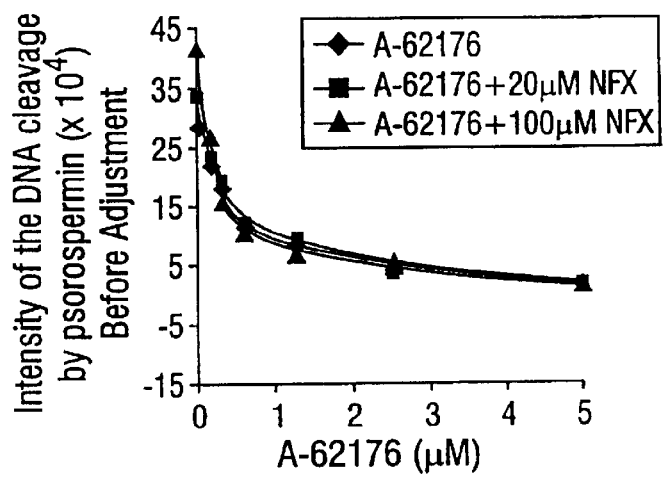
Figures 3, 9B:
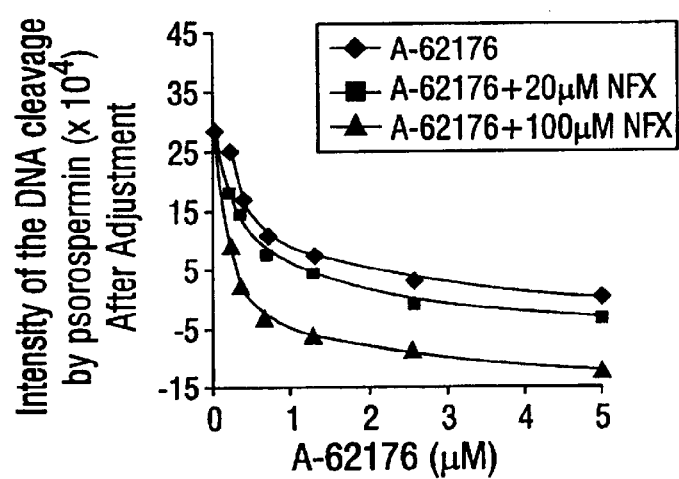

FIG. 3. Structures of the pyridobenzophenoxazines shown in Table 1.

FIGS. 4A–4E. (A) Solid-phase synthesis of N-substituted aminobenzylquinobenzoxazines, (B) solid-phase synthesis of phenanthrenyl-conjugated quinobenzoxazines, (C) solution-phase synthesis of benzo-annulated quinobenzoxazines, (D) solution-phase synthesis of di-benzofuran-conjugated quinobenzoxazines, (E) synthesis of an alkylating bromoacetyl-conjugated quinobenzoxazine.

Figure 5A:
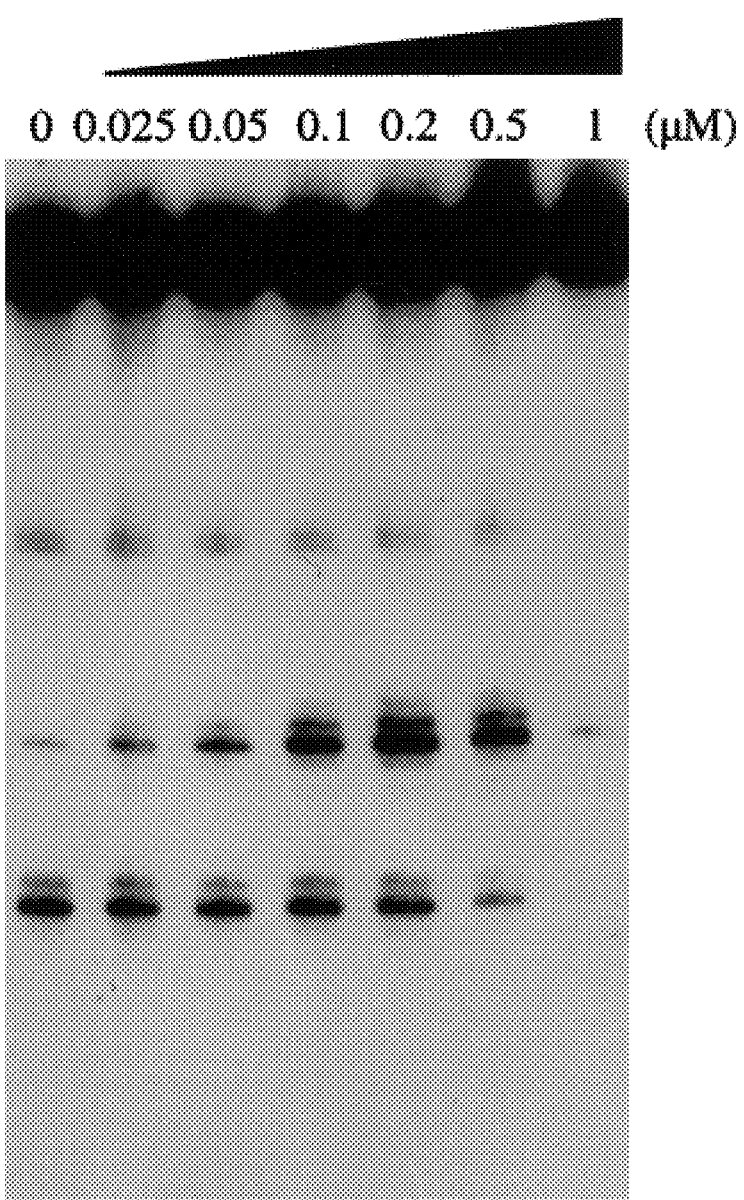
Figure 5B:
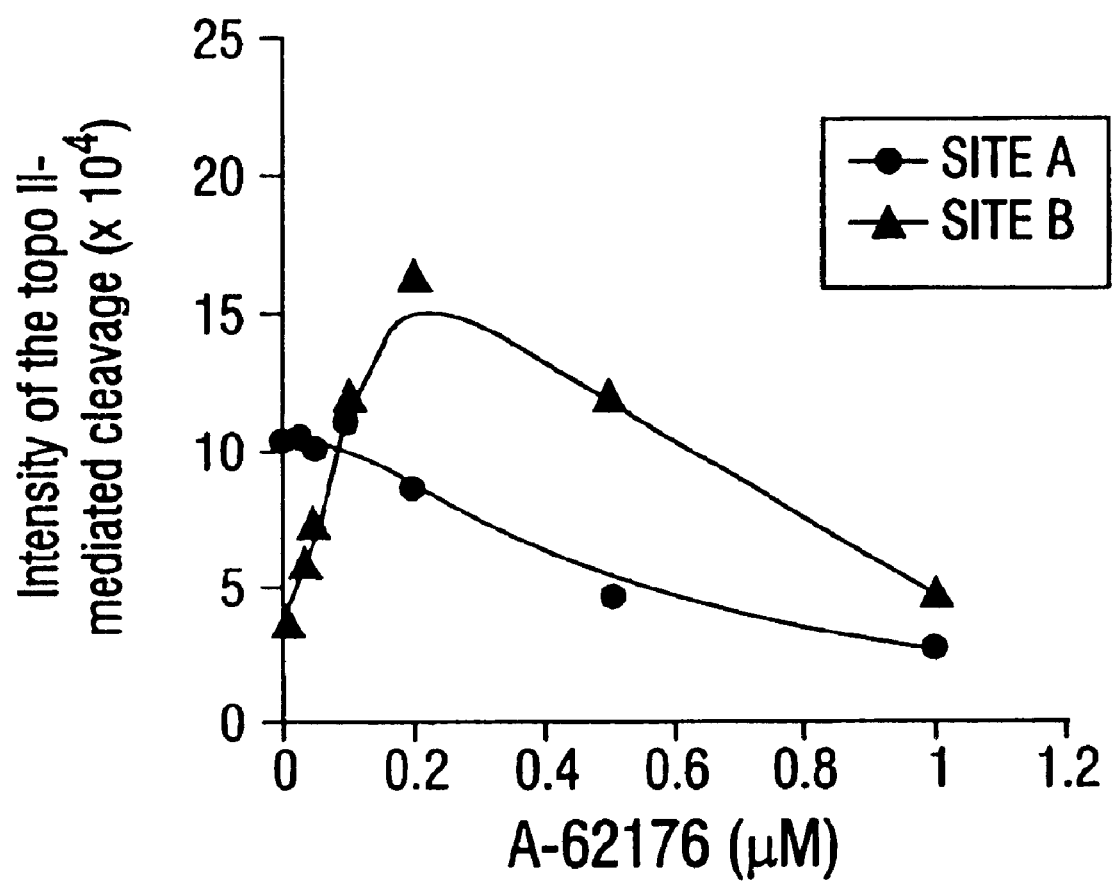

FIGS. 5, A–B. Effect of A-62176 (I in FIG. 2) on DNA cleavage by topo II in the presence of ATP. (A) Autoradiogram of a 12% denaturing polyacrylamide gel showing topo II-mediated cleavage pattern in the presence of A-62176. The cleavage reaction was done in a reaction buffer containing 10 mM imidazole-HCl (pH 6.0), 10 mM $MgCl_2$, 50 mM KCl, and 1 mM ATP, as described in the Materials and Methods section. Lanes 1–7 contain 20 units of Drosophila topo II. Lane 1 contains no drug. Lanes 2–7 contain 0.2, 0.5, 1, 2, 5 and 10 $\mu$M of A-62176, respectively. (B) Topo II cleavage products indicated by arrows in (A) were quantitated using a PhosphorImager and analyzed using ImageQuanNT software (Molecular Dynamics). The intensity of the topo II-mediated cleavage was determined from the volume of the bands [indicated by arrows in (A)] normalized by the total radioactivity in each lane.

Figure 6:
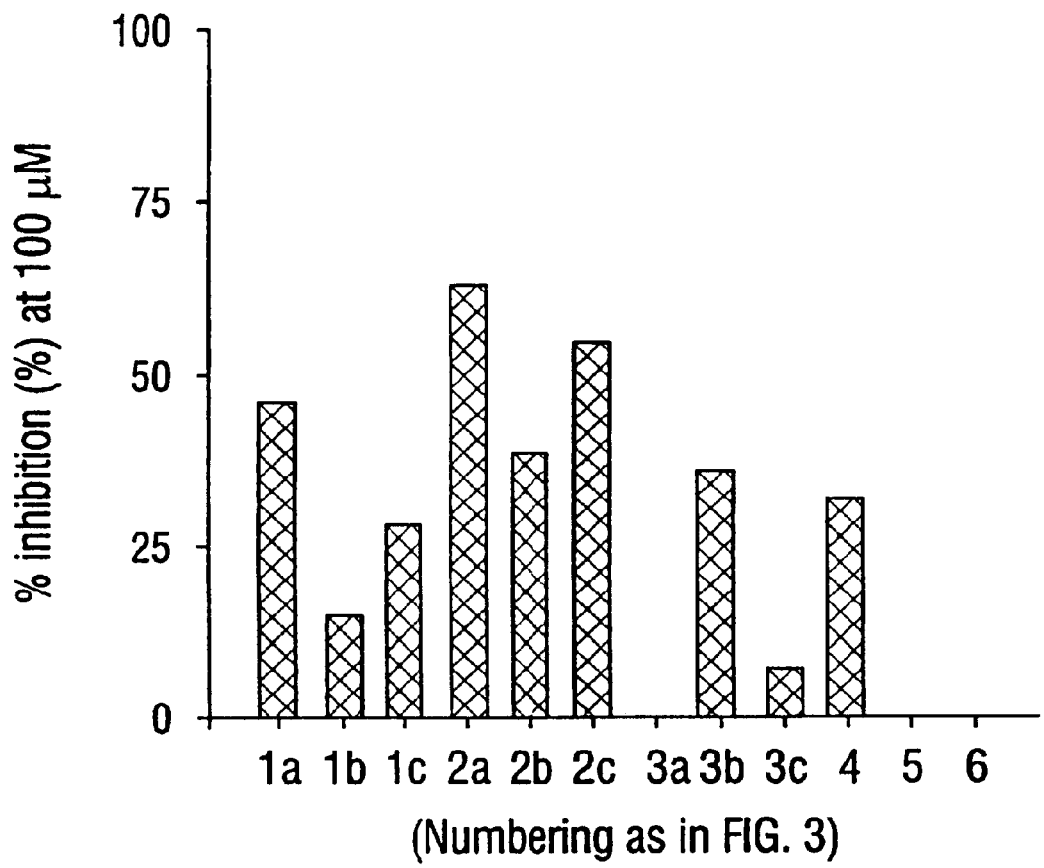

FIG. 6. Summary of telomerase inhibition studies.

Figure 7:
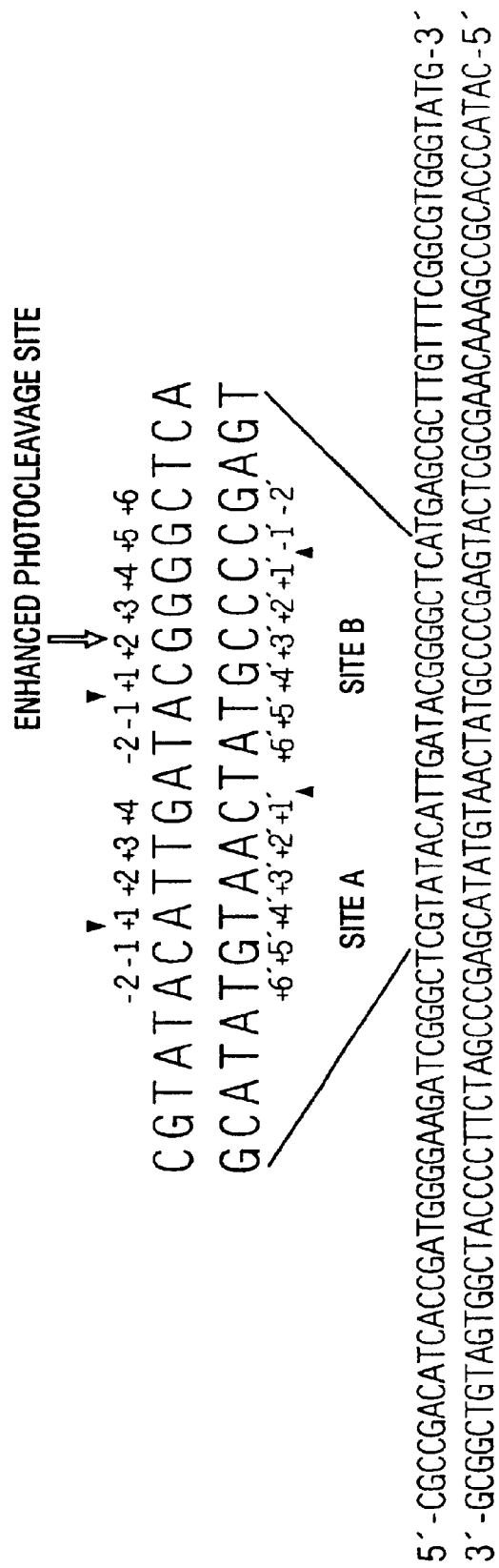

FIG. 7. The 80-base-pair oligonucleotide used in this study. In order to precisely define the location of the bases at the topo II cleavage site, negative and positive numbers ( . . . –2, –1, +1, +2 . . . ) are used to indicate the bases at the 3' and 5' termini of the cleaved phosphodiester bonds on the top strand, and corresponding negative and positive numbers ( . . . +2', +1', –1', –2' . . . ) are used for the bottom strand.

FIGS. 8, A–B. Results of competition studies between psorospermin and A-62176 (I in FIG. 2) or Norfloxacin (II in FIG. 2). (A) Lanes 1 and 2 are control DNA without and with heat treatment, respectively. Lanes 3 and 4 contain the Maxam-Gilbert sequencing reactions for AG and TC. Lane 5 contains DNA and psorospermin only. Lane 6 contains DNA, psorospermin, and topo II without A-62176 or Norfloxacin. Lanes 7–11 and 12–16 contain 0.5, 1, 2, 5, and 10 $\mu$M of A-62176 and Norfloxacin, respectively. (B) Strand breakage products indicated by the arrowheads in (A) were quantitated using a PhosphorImager and analyzed using ImageQuaNT software (Molecular Dynamics). The intensity of the DNA cleavage produced by psorospermin was determined from the volume of the bands [indicated by arrowheads in (A)] normalized by the total radioactivity in each lane.

Figure 8A:
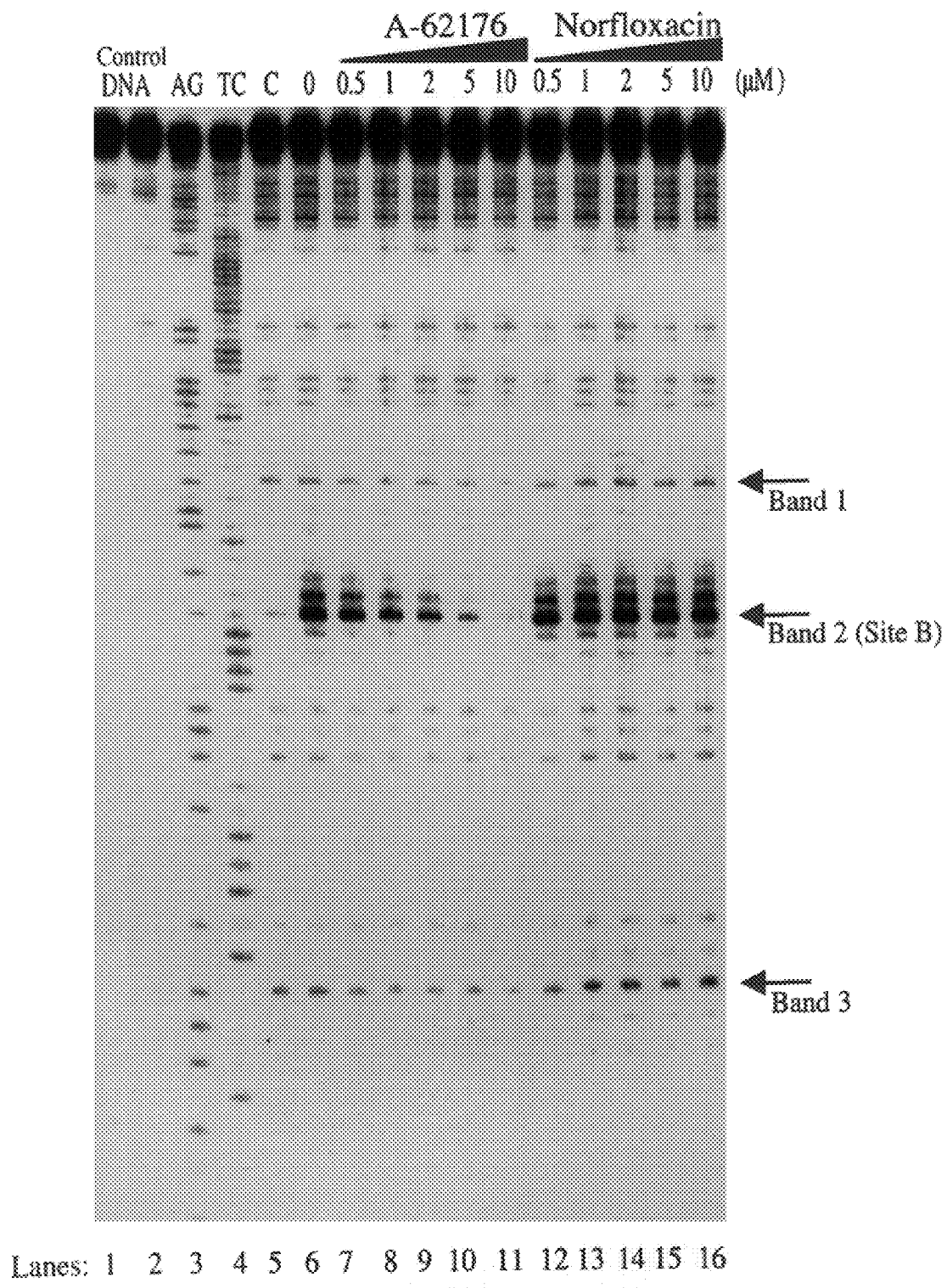
Figure 8B:
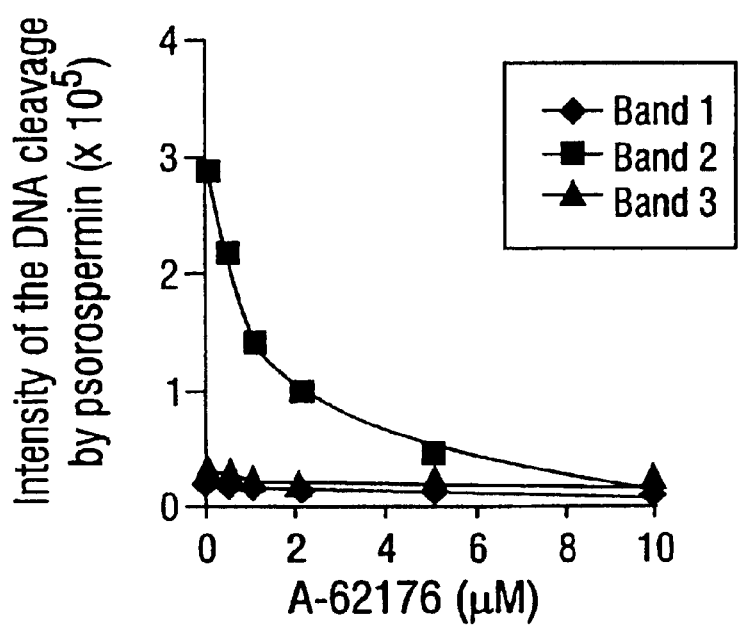
Figure 8C:
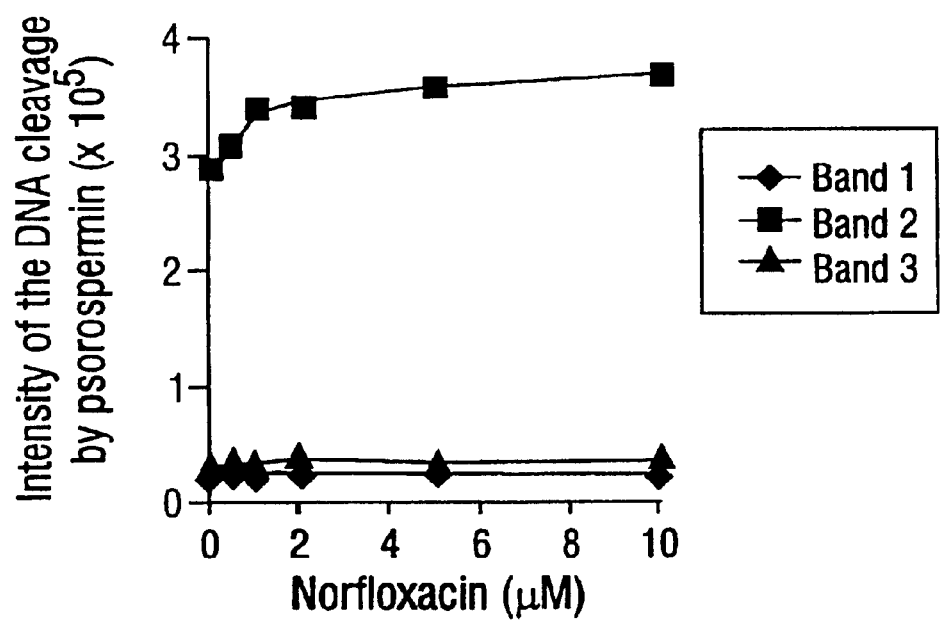

FIG. 8C. Strand breakage products indicated by the arrowheads in FIG. 8A were quantitated using a PhosphorImager and analyzed using ImageQuaNT software (Molecular Dynamics). The intensity of the DNA cleavage produced by psorospermin was determined from the volume of the bands normalized by the total radioactivity in each lane.

FIG. 9A and FIG. 9B. Results of competition studies between psorospermin and A-62176 in combination with Norfloxacin. (A) Lane 1 is control DNA with heat treatment. Lanes 2 and 3 contain the Maxam-Gilbert sequencing reactions for AG and TC, respectively. Lane 4 contains DNA and 10 $\mu$M of psorospermin only. Lanes 5–25 contain DNA, 10 $\mu$M of psorospermin, and 10 units of Drosophila topo II. Lanes 5–11 contain 0, 0.16, 0.32, 0.63, 1.25, 2.5, and 5 $\mu$M of A-62176, respectively. Lanes 12–18 contain 0, 0.16, 0.32, 0.63, 1.25, 2.5, and 5 $\mu$M of A-62176 plus 20 $\mu$M of Norfloxacin, respectively. Lanes 19–25 contain 0, 0.16, 0.32, 0.63, 1.25, 2.5, and 5 $\mu$M of A-62176 plus 100 $\mu$M of Norfloxacin, respectively. (B) Quantitations are the same as FIG. 7B for graphs I and II. The data in graph III were obtained by subtracting the difference between lanes 12 and 5 and lanes 19 and 5, which is the enhancement effect resulting from Norfloxacin only, from the data in graph II.

FIGS. 10, A–B. Schematic representation of ternary complexes topo II-A-62176-DNA (A), topo II-A-62176/Norfloxacin-DNA (B).

Figure 11:
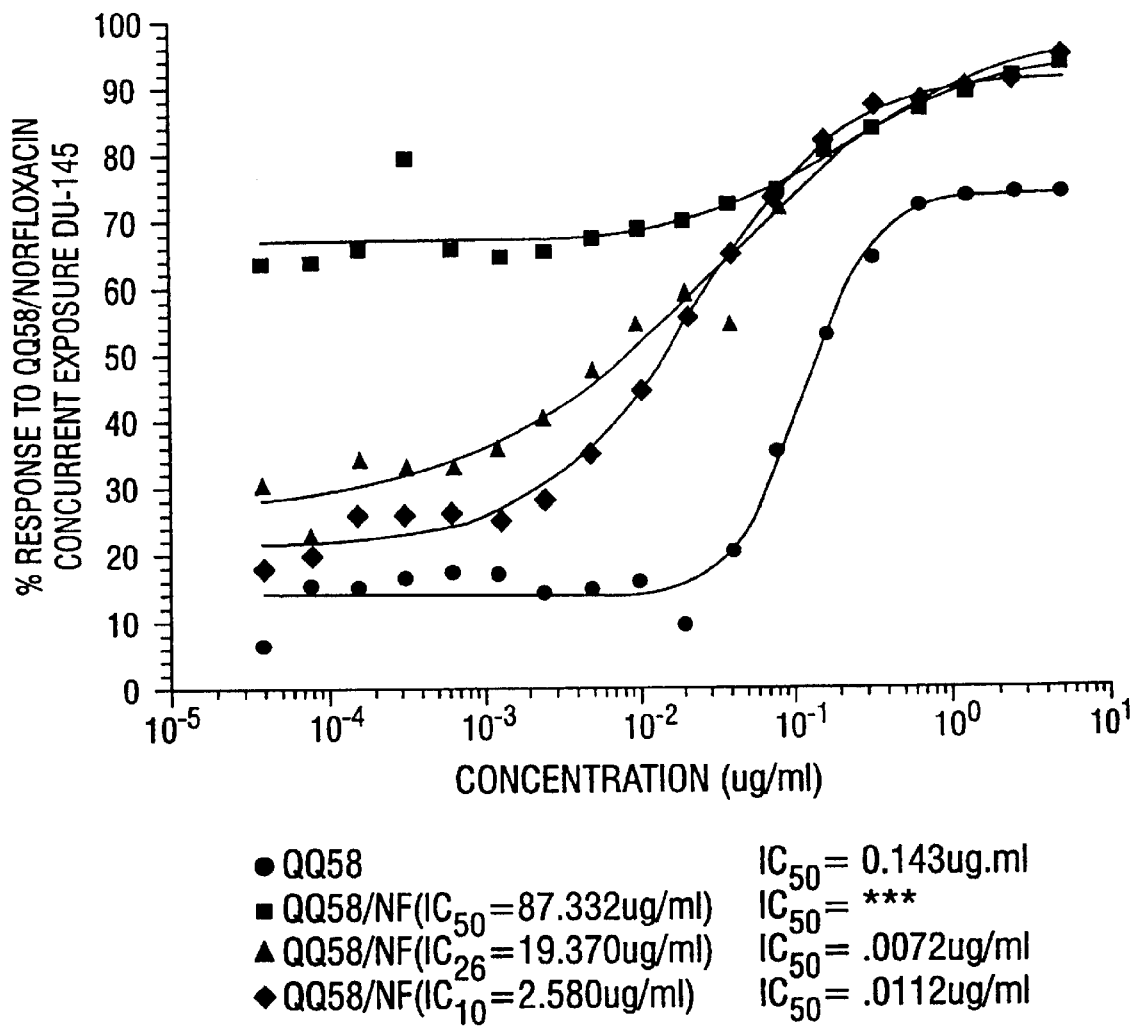

FIG. 11. Effect of increasing concentrations of Norfloxacin on the cytotoxic effect of QQ58, compound III in FIG. 2 in the prostate cell line DU-145. Compound III was either given alone (●) or in combination with Norfloxacin at concentrations of 2.58 (♦), 19.37 (♦), or 87.33 (■) $\mu$g/ml. For additions of 2.58 and 19.37 $\mu$/ml of Norfloxacin, the $IC_{50}$ of compound III was increased by approximately 14- and 20-fold.

Figure 12A:
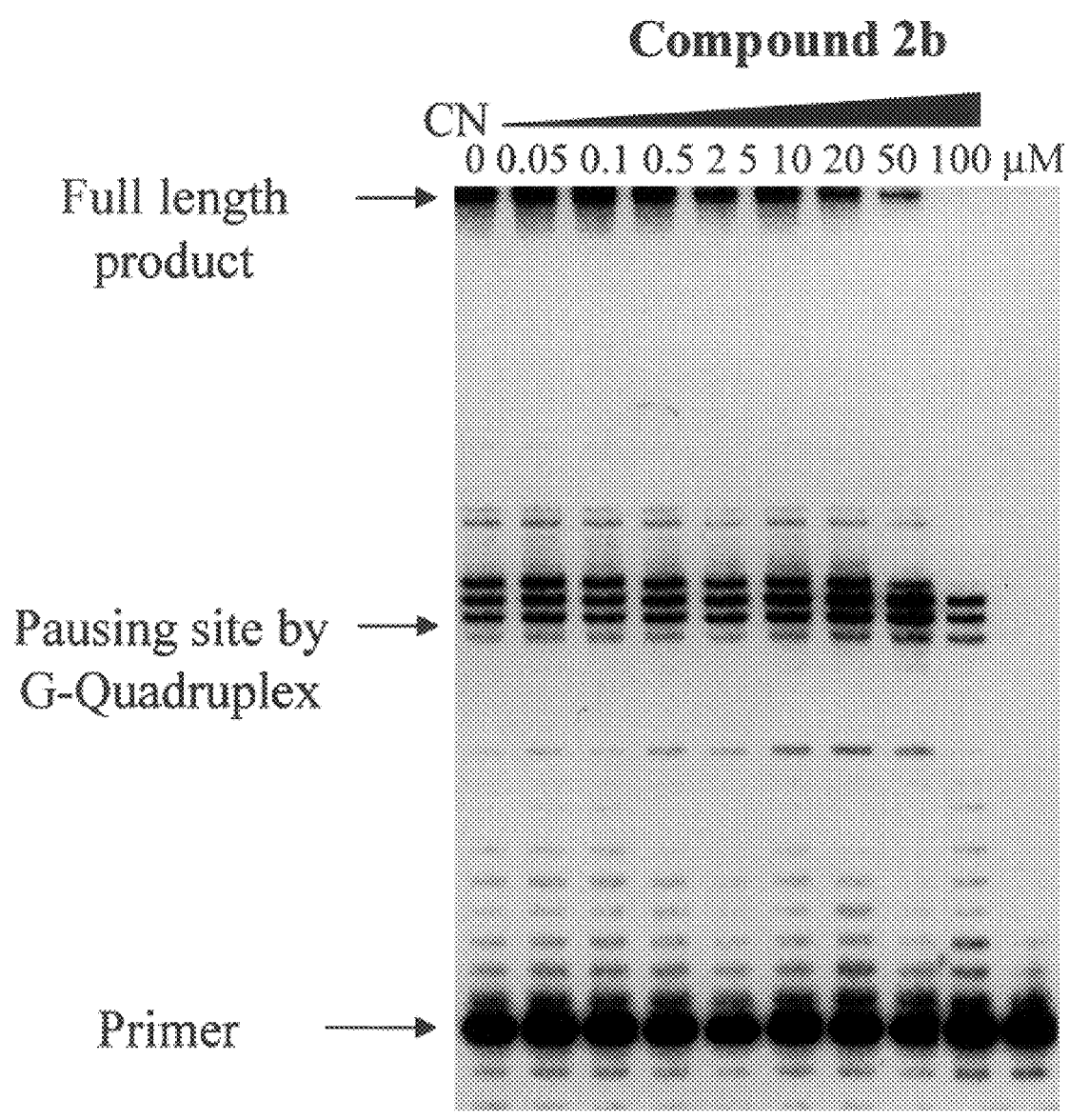
Figure 12B:
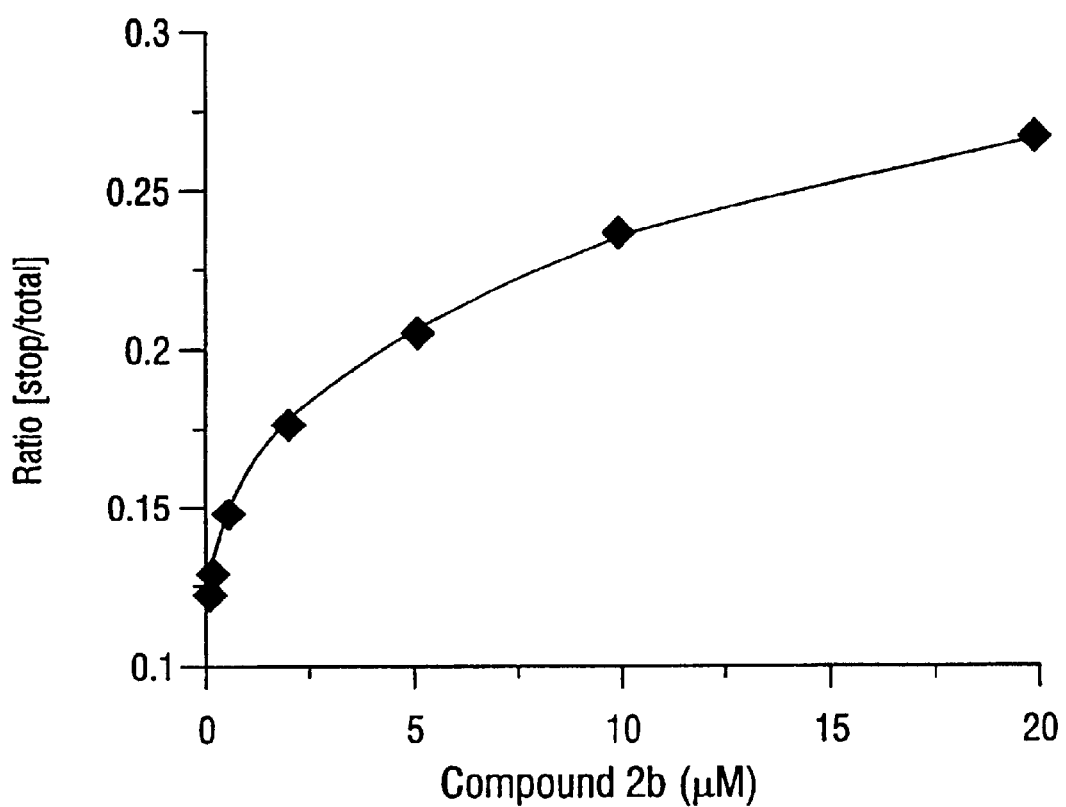

FIG. 12A and FIG. 12B. Compound 2b (see FIG. 3) concentration-dependent block of Taq polymerase DNA synthesis by the G-quadruplex structure formed on the HT4 template at 55° C. (A) Autoradiogram of a sequencing gel showing enhanced DNA synthesis pausing at the G-quadruplex site with increasing concentrations of 2b. Arrows indicate the positions of the full length product of DNA synthesis, the G-quadruplex pausing site, and the free primer. (B) Quantitation of the gel using ImageQuaNT software.

4.0 DESCRIPTION OF ILLUSTRATIVE EMBODIMENTS

4.1 A Model for Quinobenzoxazine Self-Assembly on DNA

Figure 1B:
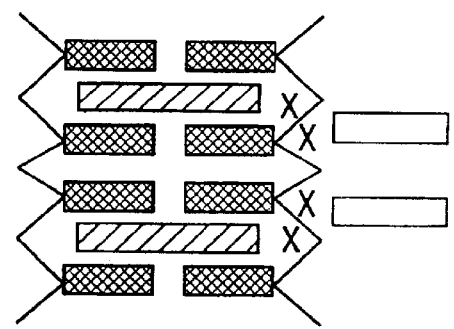
Figure 2A:
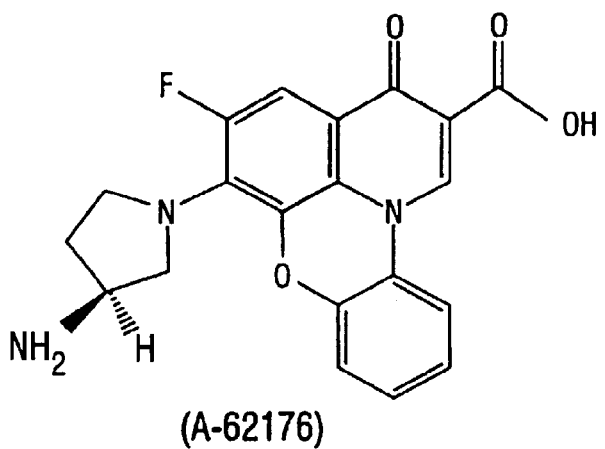
Figure 2B:
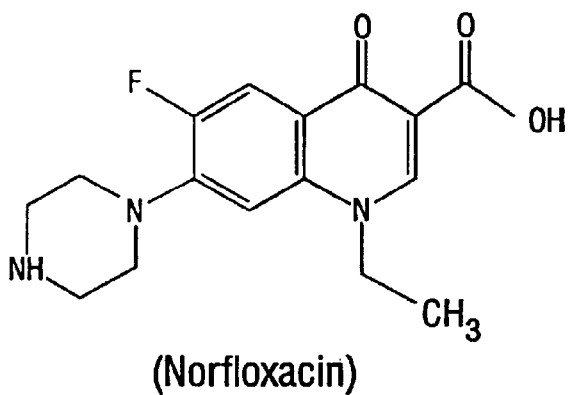
Figure 2C:
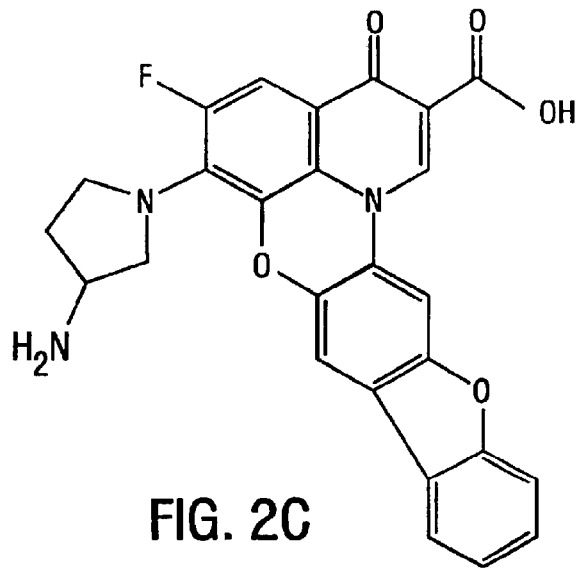
Figure 3C:
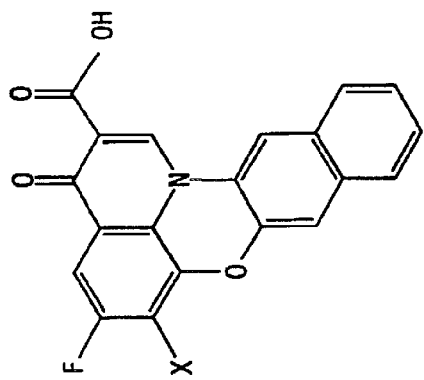
Figure 3B:
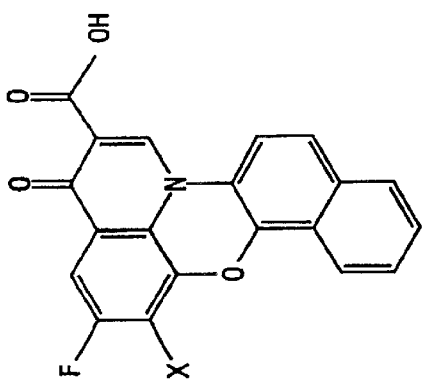
Figure 3A:
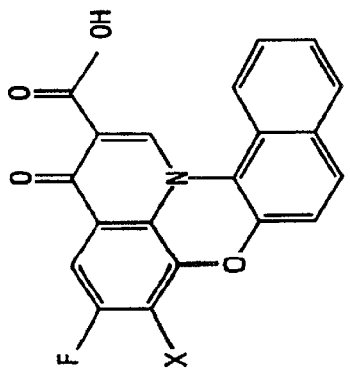

Norfloxacin, an antibacterial fluoroquinolone parent compound to the quinobenzoxazines that does not intercalate into duplex DNA, shows a cooperative effect on the DNA binding of the quinobenzoxazines, suggesting that Norfloxacin can replace the externally bound quinobenzoxazine of a DNA-bound 2:2 drug:$Mg^{2+}$ complex (Fan et al., 1995; Yu et al., 1996) (FIG. 1A). Additionally, Norfloxacin and the quinobenzoxazine A-62176 exhibit cooperative interaction with DNA in the presence of $Mg^{2+}$ and have an additive effect on lengthening of the DNA helix. On the basis of this information, it was suggested that the externally bound quinobenzoxazine molecule of the proposed model be replaced by the nonintercalating Norfloxacin (FIG. 1B). This suggestion was made, however, on the basis of experimental evidence on drug-DNA binary complex formation in the absence of topo II. It was not known, and may have been unlikely, that the model binary complex could form in the presence of topo II, and if it did, what activity it would exhibit.

The inventors have shown that the model dimer does form in the presence of topoisomerase II, and its component parts have certain structural and functional characteristics that may be exploited to develop a new series of antineoplastic and antibiotic agents. It is contemplated that the external portion of the assembly may be responsible for interacting with topoisomerase II. Thus, to design and synthesize more potent topoisomerase II inhibitors, the inventors have changed the two moieties systematically by changing either quinobenzoxazine's intercalation ability or its magnesium binding ability. For this reason, the 2:2 quinobenzoxazine:$Mg^{2+}$ heterodimer model of the instant invention has important implications for future drug design by exploiting the two moieties, one of which interacts exclusively with DNA through intercalation, while the other externally binds to DNA.

For example, it is contemplated that the external portion of the dimer interacts with topo II. Specifically, the inventors' results suggest that topo II induces transient structural distortion, possibly unwinding, that is captured or stabilized by the binding of a quinobenzoxazine at the topo II cleavage gate. This binding of the quinobenzoxazine:$Mg^{2+}$ heterodimer to the topo II-DNA complex includes not only the intercalation of one quinobenzoxazine molecule to the partially unwound DNA base pairs at the gate, but also the interaction of the externally bound molecule with topo II. The cooperative effects of these molecules in the dimer may result in an increased ability to stabilize the topoisomerase II-DNA complex either by increased topo II-interaction or by increased DNA binding abilities. This confirms the assertion that both the intercalation and the externally bound moieties, as well as the $Mg^{2+}$ binding ability of the quinobenzoxazine, should be considered for future drug design.

One approach taken in the instant invention was to extend the polyaromatic ring system that intercalates into the base bition effects on MDA-231 breast, H226 Non-small Cell, HT-29 Colon, Rali Lymphoma, DU-145 prostate human cancer cells, and B16 murine melanoma cells (Table 1). The $IC_{50}$ values of these inhibitors were in the range of 4 nM to 2 $\mu$M. They also showed potent inhibition effects against human topoisomerase II with $IC_{50}$ values in the micromolar range. Some of the compounds have a greater DNA unwinding ability than A-62176. It appears that the higher DNA unwinding ability of these compounds leads to higher potency of topoisomerase II inhibition and therefore cytotoxicity against tumor cells (Table 1).

The inventors also have shown that combining the non-intercalator Norfloxacin (II in FIG. 2) with III in FIG. 2 increases the cytotoxic potency of III up to 20-fold in an in vitro system using the prostate cell line DU-145. Thus, the 2:2 heterodimer model proves to be valid at the DNA, topoisomerase II-DNA complex, and the in vitro levels, and therefore may be expected to be valid at the in vivo level.

This model has allowed the development of a new series of quinobenzoxazines and their analogues that exhibit antineoplastic and antibiotic activity. On the basis of this model, a solid-state synthesis method was developed to provide large numbers of compounds to study in the model:dimer complex and to evaluate their potentially increased antineoplastic and antibiotic activity compared to the parent compounds.

TABLE 1

Decatenation Inhibition, DNA Unwinding, and Cytotoxicity Data for the Pyridobenzophenoxazines

| compd | topoisomerase II inhibition $IC_{50}$ ($\mu M$)[a] | DNA unwinding concn ($\mu M$)[b] | $IC_{50}$ (nM) | | | | | |
|---|---|---|---|---|---|---|---|---|
| | | | B16 melanoma | MDA-231 breast | H226 non-small-cell lung | HT-29 colon | Raji lymphoma | DU-145 prostate |
| A-62176 (S) | 0.51 | 50 | 170 ± 10 | 160 ± 20 | 90 ± 3 | 160 ± 10 | 50 ± 6 | 160 ± 30 |
| 1a (racemic) | 0.77 | | 440 ± 60 | 150 ± 40 | 140 ± 10 | 180 ± 10 | 86 ± 6 | 200 ± 30 |
| 1b (R) | 1.22 | 35 | 680 ± 50 | 350 ± 60 | 2400 ± 100 | 360 ± 40 | 160 ± 70 | 360 ± 120 |
| 1c (S) | 0.72 | 19 | 130 ± 20 | 190 ± 40 | 130 ± 10 | 270 ± 40 | 82 ± 8 | 140 ± 10 |
| 2a (racemic) | 0.55 | | 40 ± 4 | 27 ± 2 | 22 ± 2 | 30 ± 3 | 18 ± 1 | 17 ± 7 |
| 2b (R) | 0.24 | 3 | 20 ± 2 | 5 ± 1 | 13 ± 5 | 26 ± 1 | 34 ± 2 | 30 ± 10 |
| 2c (S) | 0.49 | 10 | 180 ± 20 | 84 ± 7 | 27 ± 4 | 51 ± 6 | 20 ± 4 | 64 ± 7 |
| 3a (racemic) | 0.77 | | 100 ± 10 | 23 ± 4 | 4 ± 2 | 28 ± 5 | 38 ± 6 | 25 ± 9 |
| 3b (R) | 0.42 | 15 | 140 ± 15 | 21 ± 2 | 22 ± 15 | 22 ± 3 | 32 ± 5 | 48 ± 8 |
| 3c (S) | 0.44 | 13 | 20 ± 6 | 10 ± 2 | 14 ± 2 | 23 ± 3 | 29 ± 5 | 30 ± 6 |
| 4 | 9.6 | >100 | 2100 ± 300 | 2200 ± 300 | 2100 ± 200 | 2000 ± 200 | 800 ± 50 | 840 ± 270 |
| 5 | 1.84 | >100 | 650 ± 60 | 380 ± 50 | 200 ± 30 | 360 ± 90 | 210 ± 40 | 140 ± 40 |
| 6 | 0.64 | >100 | 45 ± 48 | >$10^6$ | >$10^5$ | 6800 ± 1800 | 7.2 ± 7.6 | 75 ± 32 |

[a]Drug concentration that inhibits 50% of the conversion of catenated to decatenated KDNA by human topoisomerase II.
[b]Drug concentration that causes a shift of the topoisomers from the original to the middle position between the relaxed and the supercoiled bands.

pairs. In this manner, a series of new quinobenzoxazine analogues have been synthesized, and preliminary studies show that they are more potent against several cancer cell lines than the parent compound quinobenzoxazines. An additional new series of compounds may likewise be synthesized via further elucidation of the interaction between the two molecules of the model dimer, $Mg^{2+}$, DNA, and topoisomerase II.

In a use of the invention, it was noted that since the phenyl ring portion of I in FIG. 2 is actually inserted between DNA base pairs, the intercalation ability may be increased by extending the phenyl ring to a naphthyl ring. A series of new pyridobenzophenoxazine analogues were thus designed and synthesized (FIG. 3). These analogues showed strong inhi- On the basis of the inventors' prior experience with intercalators that interact with G-quadruplexes, the inventors designed pyridobenzophenoxazines that should interact with G-quadruplexes. 2b in FIG. 3 is an example of such a compound. Using UV spectral analysis, a DNA synthesis arrest assay (Han et al., 1999), a photocleavage assay (Wheelhouse et al., 1998), and NMR titrations, it was demonstrated that these compounds do interact with G-quadruplexes. Furthermore, this compound was shown to inhibit telomerase and cause chromosomal aberrations in a sea urchin embryo system.

4.2 Solid-Phase Synthesis of Quinobenzoxazines

Quinolone antibacterial agents represent a class of highly potent, broad-spectrum antibiotics. Thousands of quinolones have been synthesized to study their structure and activity relationships (Mitscher et al., 1990). Quinobenzoxazines, with a tetracyclic ring structure, are derived from quinolones. Some quinobenzoxazines show excellent antineoplastic activities (Chu and Maleczka Jr., 1987; Chu et al., 1994); however, only a limited number of quinobenzoxazine derivatives have been synthesized, and their structure-activity relationships have not been thoroughly investigated.

In studying the anticancer function of the quinobenzoxazines, several researchers have proposed a model of quinobenzoxazine self-assembly on DNA (Fan et al., 1995; Yu et al., 1996). On the basis of this model, the inventors designed a series of novel quinobenzoxazines, pyridobenzophenoxazines, pyrridonaphthophenoxazines, and other related compounds, some of which showed excellent anticancer activity. In particular, the synthesized compounds exhibit higher DNA binding affinities and greater DNA unwinding abilities in the quinobenzoxazine self-assembly model.

To study the structure-activity relationships of these compounds, a large number of derivatives is needed. Traditional solution-phase, one-by-one synthesis of these compounds is inefficient and highly limited by human resources. To solve this problem, a solid-phase synthesis technique was developed to make large libraries of these compounds in parallel or combinatorial fashion.

Organic synthesis on solid support has many advantages. First, isolation of support-bound reaction products is accomplished simply by washing away reagents from support-bound material so that reactions can be driven to completion by use of excess reagents. Second, innovative methods are available for the manipulation of discrete compounds when compounds are attached to a solid support. Third, solid-phase synthesis makes it easier to generate large libraries of compounds using existing automation technologies. Therefore, the use of solid-phase synthesis and combinatorial chemistry to generate small molecule libraries has rapidly become a major frontier in organic and medicinal chemistry.

Two solution-phase synthetic routes have been reported for the quinobenzoxazines (Chu and Maleczka Jr., 1987; Radl and Zikan, 1989). Additionally, there also is a solid-phase synthesis procedure for quinolones (MacDonald et al., 1996) as well as for fluoroquinolones; however, there are no solid phase synthetic routes for making libraries of the quinobenzoxazines or their analogues. To fill the need for reliable solid-state synthesis methods for these compounds, the inventors have provided a new solid-phase synthesis technique capable of producing a large number of quinobenzoxazine analogues more efficiently that the previously available solution-phase techniques.

4.3 Loading Precursor onto Solid Support

The first step in the new synthesis is to load a carboxy-acetophenone onto a solid support by a transesterification or acylation reaction, which produces a solid-bound ester. For example, one may employ a Wang resin as a solid support (see FIG. 4A and FIG. 4B). If it is desired to maintain the ester bond between the compound and the solid support, the solid support must be compatible with the protective groups to be utilized during the rest of the synthesis process. For example, if the protective group used for peptide synthesis is to be Teoc, the Wang resin serves as a compatible support because use of a fluoride ion to deprotect the amino group will not affect the support. Likewise, if the protective group tBoc is used, the solid support must maintain its integrity under acidic conditions, and if the protective group Fmoc is utilized, the solid support should be selected to withstand basic conditions.

Carboxy acetophenones such as ethyl 2,3,4,5-tetrafluorobenzoylacetate may be loaded on a resin by a transesterification reaction in the presence of a catalytic amount of 4-dimethylaminopridine to produce a solid-bound ester.

4.4 Generation of Enaminoketoester

Once the solid bound ester is prepared, a solid bound enaminoketoester is formed to serve as a branch point from which diversified chemical scaffolds may be synthesized. The enaminoketoester may be produced by treatment of the solid bound ester with a dimethyl formamide dimethyl acetal. After a brief wash step, the resin is treated with o-hydroxy aniline derivatives (for example, a compound of formula III in FIG. 4A) to generate the resin-bound enaminoketoester, a compound of formula IV in FIG. 4A.

4.5 Formation of Tetracyclic Scaffold

Quinobenzoxazines are structured around a fused tetracyclic "base". This base is synthesized during the disclosed process via a double cyclization step using an inorganic or organic base, TMG, to form the fused tetracyclic-ring system (a compound of formula V in FIG. 4A). The inventors contemplate that a variety of scaffolding may be constructed in this manner; however, the exact scaffolding will be determined by the type of enaminoketoester formed in the previous step.

4.6 Formation of Quinobenzoxazine

After construction of the tetracyclic scaffold, quinobenzoxazine analogues are synthesized by regio-specific substitution of fluorines by cyclic nitrogeneous bases. Nucleophilic substitution of the fluorine at position 7 by a nitrogen-containing base generates the quinobenzoxazine analogues (compounds of VIII and IX in FIG. 4A).

4.7 Quinobenzoxazine Analogue Formation

Once the quinobenzoxazine is made, it can be further derivatized by deprotection of the benzylic amino group and coupling with an amino acid, acylating agent, alkylating agent, or other compounds that increase the anticancer or antibiotic activity of the compounds.

4.8 Monitoring the Synthesis

The synthesis steps were monitored by gel-phase $^{19}$F NMR and $^{13}$C NMR, which helped to optimize the reaction conditions. Since all the synthetic intermediates contained fluorine atoms, gel-phase $^{19}$F NMR and $^{13}$C NMR techniques were developed to monitor the reaction processes. The starting 2,3,4,5-tetrafluorobenzolacetate showed two sets of four peaks due to the enolization of the β-ketoester. The enaminoketoester showed one set of four peaks that is different from the starting material. After the double cyclization, only two peaks were observed. The nucleophilic substitution generated a product with only one $^{19}$F NMR signal. The deprotection of the benzylic amino group can be monitored by the $^{13}$C NMR of the silyl group at about 0 ppm.

4.9 Application of Solid-Phase Synthesis to Additional Related Compounds

Figures 1, 4B:
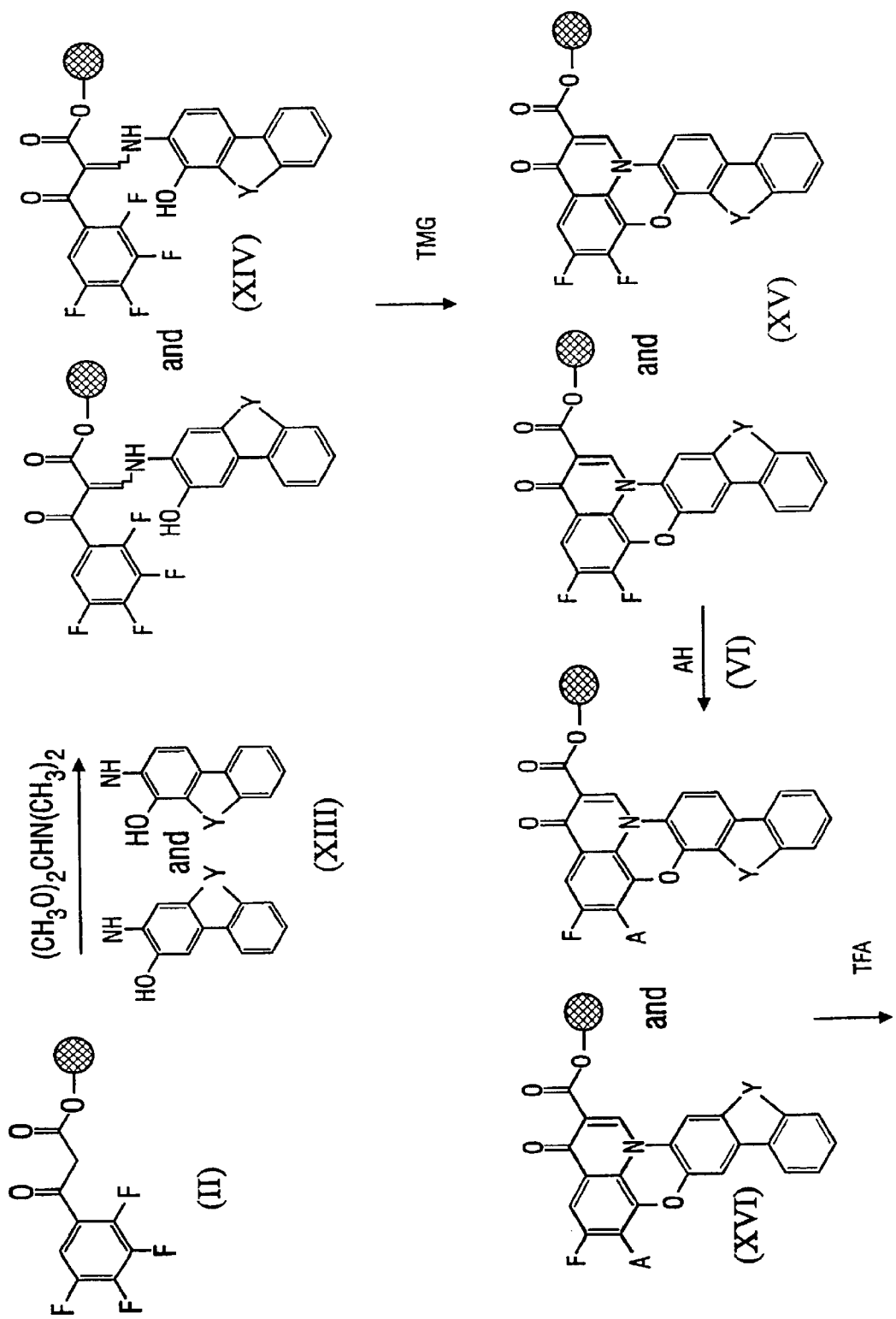
Figures 2, 4B:
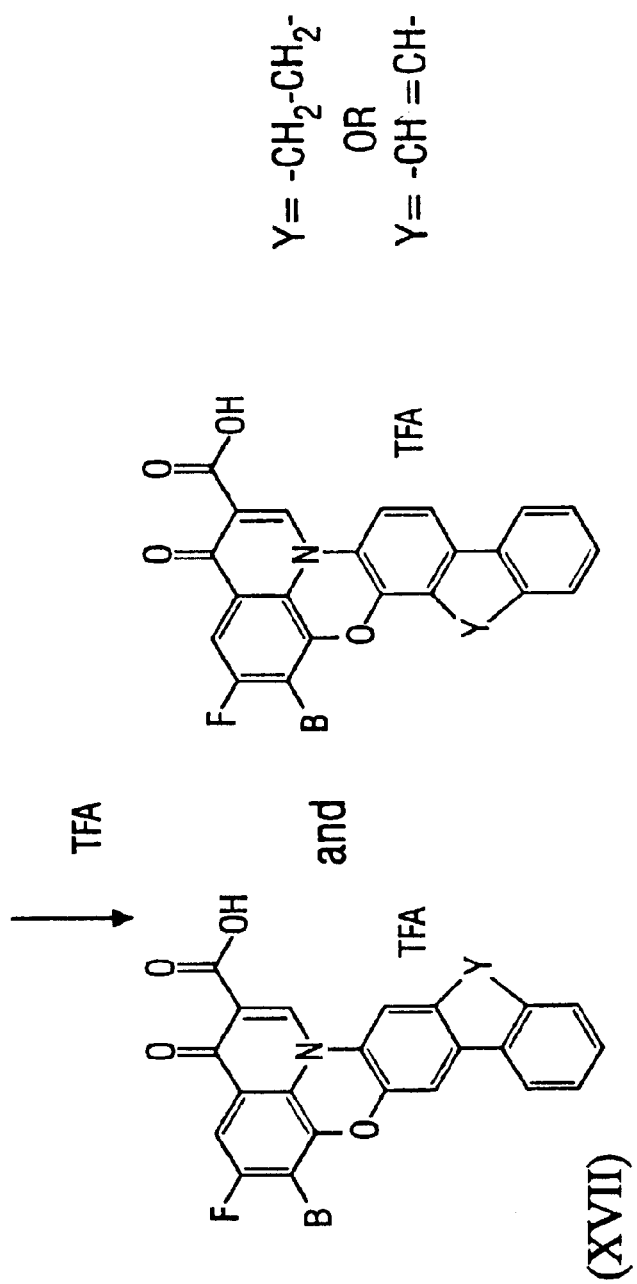

The new solid-phase synthesis of quinobenzoxazines can be applied to other related quinobenzoxazines. FIG. 4B shows an example of solid-phase synthesis of phenanthrene-fused quinobenzoxazine analogues. 2-Amino-9,10-dihydrophenanthren-3-ol or 2-aminophenanthren-3-ol, instead of 2-hydroxyaniline (a compound of formula III wherein $R_2$=H), is conjugated to the resin-bound β-ketoester (a compound of formula II in FIG. 4B) to give resin-bound enaminoketoester (XIV), which is cyclized using 1,1,3,3-tetramethylguanidine to generate 1,2-difluoroquinobenzoxazine (XV). The resulting tetracyclic scaffold is further derivatized by regio-selective substitution with pyrrolidine (IV) followed by resin cleavage reaction with 50% trifluoroacetic acid in dichloromethane to give the final product (XVIII) in the same manner as sections 4.3–4.8. In FIG. 4A, the $R_2$ group could be the alkyl group, acyl group, alkylating group, and peptides that are useful in building large libraries of quinobenzoxazine analogues as DNA intercalators having DNA alkylating agents and DNA groove binders. This method is not limited to FIG. 4A and FIG. 4B. A number of other derivatives such as (XXII) and acid-insensitive 1,2-hydroxyamine analogues could be synthesized using this solid-phase synthesis.

Figure 4C:
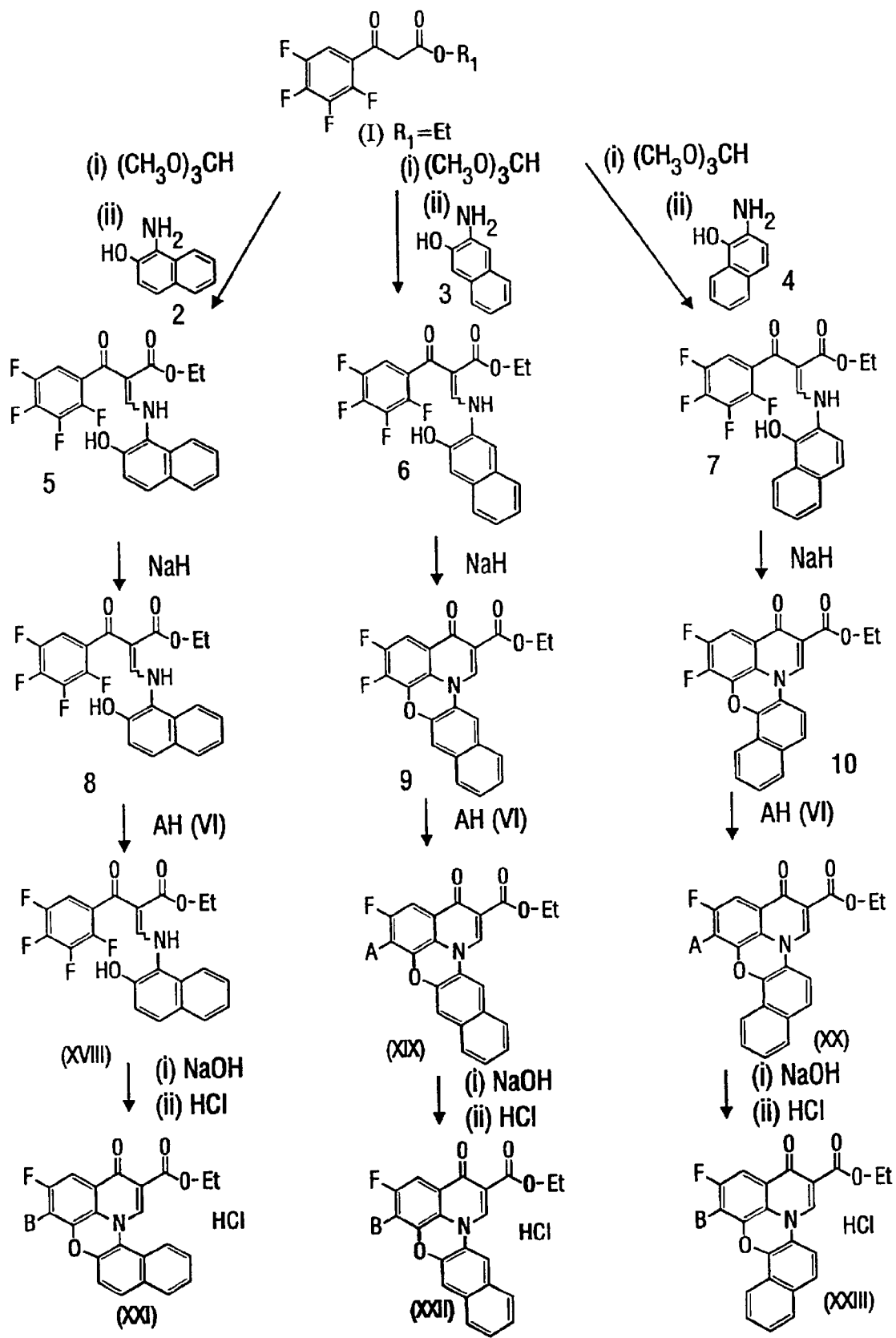
Figure 4D:
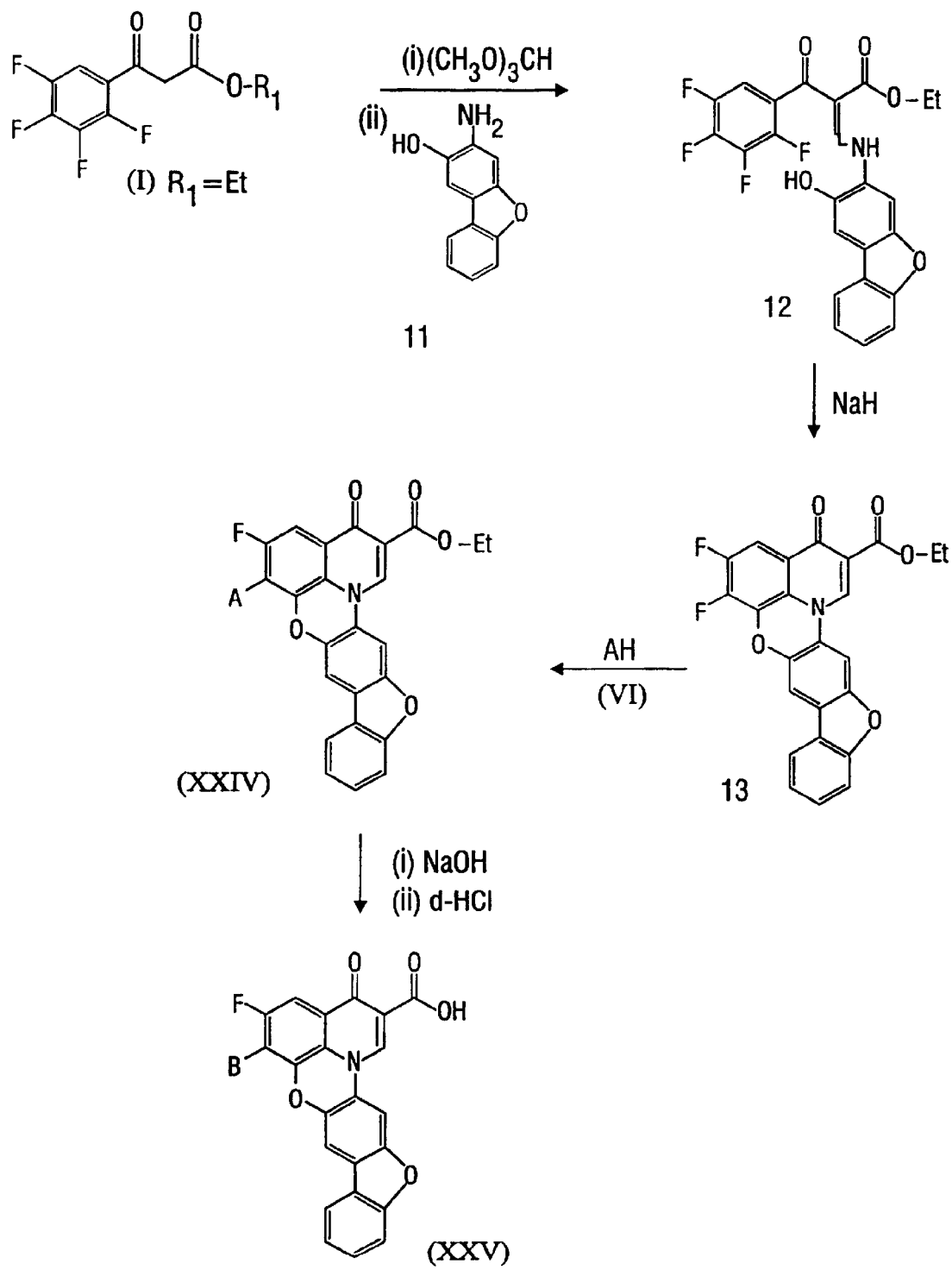
Figure 4E:
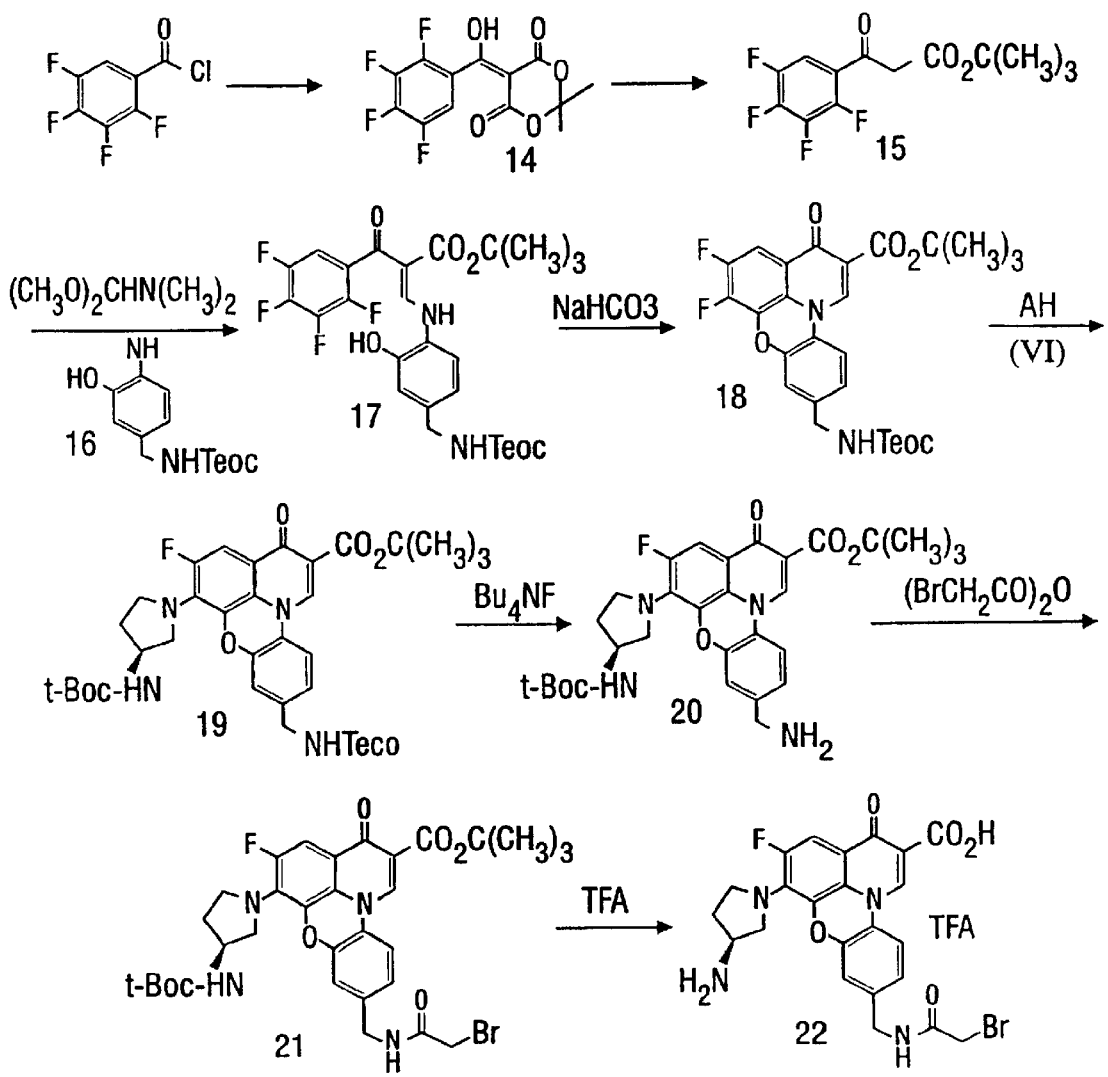

4.9.1 Solution Phase Synthesis of Benzo-Annulated and Di-Benzofuran-Conjugated Quinobenzoxazines (FIG. 4C and FIG. 4D) and Alkylating Bromoacetyl-Conjugated Quinobenzoxazine (FIG. 4E)

Novel compounds with increased ability to unwind duplex DNA and inhibit human topoisomerase II catalytic activity were designed and synthesized based on the quinobenzoxazine self-assembly model. The end products, as well as some intermediates, of the synthesis are novel compounds, with the end products being of a group termed pyridobenzophenoxazines. The synthesis of these compounds began with a carboxyacetophenone, 2,3,4,5-tetrafluorobenzoyl acetate prepared according to the literature (Chu and Malezka, Jr., 1987).

The aminoketoacid was then treated with sodium hydride by increasing reaction temperatures to reflux in THF to complete the double annulation. This step avoided the protection and deprotection of the hydroxyl group as in the synthesis of quinobenzoxazine (Chu and Maleczka, Jr., 1987), and therefore shortened the synthetic route by three steps and improved overall yields.

Nucleophilic substitution of the fluoride of compounds 8, 9, and 10 (FIG. 4C), regioselectively with racemic or optically pure 3-tert-butoxycarbonylamino pyrrolidine followed by hydrolysis of the carboxylate and deprotection of the amino group to yield the final product.

Using similar chemistry to that shown in FIG. 4C and FIG. 4D, the alkylating bromo-acetyl-conjugated quinobenzoxazine 22 was synthesized (FIG. 4E).

4.10 Quinobenzoxazine Analogues

As shown in FIG. 4C and FIG. 4D, the newly designed quinobenzoxazine analogues are distinct from the parent class of quinobenzoxazines by either having benzo-annulated ring systems or extended side chains. These add-on portions are expected to increase their DNA binding affinities and/or unwinding abilities. The parent compounds, including the quinobenzoxazines, quinobenzothiazines, and pyrido-acridine derivatives described herein, are novel and may be synthesized by a solid-state synthetic method, rather than by solution synthetic chemistry. Exemplary analogues include pyridobenzophenoxazines.

4.11 Pyridobenzophenoxazines

Several novel pyridobenzophenoxazine compounds have been designed and synthesized based on the quinobenzoxazine self-assembly model on DNA. The compounds unwind duplex DNA and inhibit human topoisomerase II catalytic activity. Furthermore, they show potent inhibitory effects on several tumor cell lines with $IC_{50}$ values in the micromolar range.

The series of pyridobenzophenoxazines that have been designed and synthesized as topoisomerase II inhibitors are shown in FIG. 3. The design was based on the 2:2 quinobenzoxazine:$Mg^{2+}$ self-assembly model for quinobenzoxazine A-62176. In this model, the benzene ring of A-62176 intercalates into DNA and binds with DNA by $^1$-$^1$ stacking with DNA base pairs. Additional stabilization is achieved by the chelation of two magnesium ions with the β-ketoacid, the amino group of the side chain, and a phosphate oxygen of the DNA backbone. Better intercalation may be achieved by extending the ring of A-62176 to a naphthalene ring.

Since the exact orientation of the benzene ring between DNA base pairs is uncertain, all three possible directions of benzo-annulation were explored to achieve the maximum $^1$-stacking interaction with DNA base pairs. Compounds of formulas XXI, XXII, and XXIII (wherein B=piperazin-1-yl) in FIG. 4C have a piperazine ring instead of a 3-aminopyrrolidine ring as side chains. Since the 3-amino group of A-62176 is proposed to chelate magnesium, the change may have some effect on its self-assembly on DNA and therefore, its topoisomerase II inhibition. For A-62176, the stereochemistry of the 3-aminopyrrolidine side-chain has effects on its topoisomerase II inhibition. The S-isomer is more potent than the R-isomer. To study the possible effects of the stereochemistry of the pyridobenzophenoxazines, the compounds were either racemic or enatiomerically pure. The synthetic procedure was based on a literature method for quinobenzoxazines with some modification (Chu and Maleczka, Jr., 1987).

4.12 Quinobenzoxazine Analogues as Antineoplastic Agents

Quinobenzoxazines are derived from quinolones, which are a class of potent, broad spectrum antibiotics. Some previously synthesized quinobenzoxazines have exhibited antineoplastic activity. Synthesis of additional antineoplastic quinobenzoxazines has been minimal, as has the study of the range of anticancer activity these compounds may exhibit. A variety of synthetic quinobenzoxazines and their analogues that display an increased ability to unwind DNA and to bind to DNA would present valuable tools to molecular biology, medicinal chemistry, and cancer chemotherapy. To meet this expectation, and to assess the antineoplastic agents claimed in this invention, the inventors conducted a series of tests to evaluate the mechanism of action that these compounds exert and to determine the range of anticancer activity they may possess.

As a reference point, the inventors studied the quinobenzoxazine A-62176 (1-(3-aminopyrrolidin-1-yl)-2-fluoro-4-oxo-4H-quino[2,3,4-i,j][1,4]benzoxazine-5-carboxylic acid), developed from antibacterial fluoroquinolones, which is active in vitro and in vivo against murine and human tumors. It has been demonstrated that A-62176 is a catalytic inhibitor of mammalian topoisomerase II (topo II) that does not stabilize the cleaved complex; however, at low drug concentrations, the inventors found that A-62176 enhances the cleaved complex formation at certain sites (FIG. 5). Using a photocleavage assay and mismatch sequences, the inventors were able to pinpoint the drug binding site to a region near the cleaved phosphodiester bonds (Kwok et al., 1999). These results indicate that a conformational change, possibly DNA unwinding, induced by topo II binding on DNA creates a high affinity binding pocket for quinobenzoxazines.

Interaction between benzo-annulated quinobenzoxazines and G-quadruplexes and resulting inhibition of telomerase also were proposed as a possible mechanism by which these compounds exert antineoplastic effects. To evaluate this interaction, some of the novel quinobenzoxazines and their analogues were screened for quinobenzoxazine analogsy effects (Sun et al., 1998). The results, shown in FIG. 6, indicate that a variety of the quinobenzoxazines do inhibit activity of telomerase. The benzo-annulated compounds are particularly effective in telomerase inhibition; however, the inventors propose that many of the quinobenzoxazines and their related analogues also will display inhibitory effects on telomerase.

The inventors have shown that the novel quinobenzoxazines act as antineoplastic agents that can exert their anticancer activity by targeting either topoisomerase II or G-quadruplexes or both at same time. This feature will enable the design and development of novel cancer chemotherapeutic agents by combining their activities against two types of cellular process and thereby generating more potent, less toxic anticancer agents with less drug resistant effects.

VII. EXAMPLES

The following examples are included to demonstrate preferred embodiments of the invention. It should be appreciated by those of skill in the art that the techniques

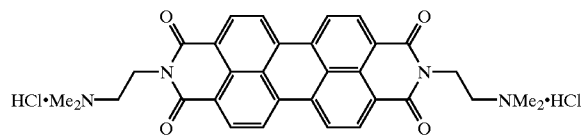

The relative inhibition of human telomerase by N,N'-bis(2-dimethylaminoethyl)-3,4,9,10-perylenetetracarboxylic acid diimide was determined in a standard primer extension assay that does not use a PCR™-based amplification of the telomerase primer extension products. Briefly, the 18-mer telomeric primer d[TTAGGG]$_3$ (1 μM) without or with N,N'-bis(2-dimethylaminoethyl)-3,4,9,10-perylenetetracarboxylic acid diimide was elongated with human telomerase in the presence of 1.5 μM of [α-$^{32}$P]-dGTP (800 Ci mmol$^{-1}$, 10 mCi ml$^{-1}$) with 1 mM dATP and 1 mM dTTP. The extension products were isolated and visualized by autoradiography after denaturing gel electrophoresis.

The IC$_{50}$ was determined to be 50 μM, and at 100 μM of N,N'-bis(2-dimethylaminoethyl)-3,4,9,10-perylenetetracarboxylic acid diimide there is an almost complete inhibition of telomerase activity. N,N'-bis(2-piperdinoethyl)-3,4,9,10-perylenetetracarboxylic acid diimide and 3 showed similar behavior.

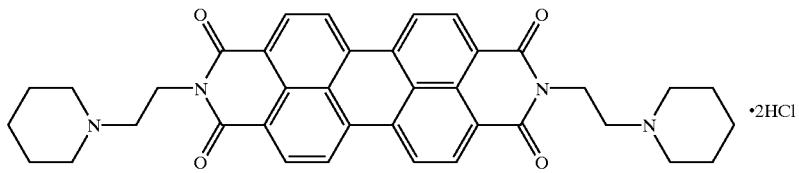

disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Telomerase Inhibition by N,N'-bis(2-Dimethylaminoethyl)-3,4,9,10-perylenetetracarboxylic Acid Diimide Selection of N,N'-bis(2-dimethylaminoethyl)-3,4,9,10-perylenetetracarboxylic acid diimide as a potential telomerase inhibitor was determined by Method (B) as described in Example 2.

Example 2

Screening Assays for Telomerase Inhibitors

Compounds that inhibit telomerase are potential drugs for the treatment of cancer. The method selects compounds based upon ability to interact with the human DNA-G-quadruplex. Several procedures for detecting this interaction include:

(A) A three dimensional structure of a candidate compound will be analyzed to determine their degree of complementarity to the three-dimensional structure of human telomeric DNA G-quadruplex. The NMR solution structure of d(AGGGTTAGGGTTAGGGTTAGGG) [pdb entry 143d] and its corresponding molecular surface, generated with the ms program, were used as inputs to the SPHGEN program. The resulting sphere cluster was used as input to DOCKv2.0 and a subset of the Cambridge crystallographic database was search using the contact scoring algorithm. N,N'-bis(2-dimethylaminoethyl)-3,4,9,10-perylenetetracarboxylic acid diimide was found to have one of the highest contact scores in the ~2000 compounds examined.

(B) Compounds may be selected for their ability to interact with human DNA G-quadruplex as indicated by UV/VIS spectroscopy. To a 10 μM solution of N,N'-bis(2-dimethylaminoethyl)-3,4,9,10-perylenetetracarboxylic acid diimide in 20 mM phosphate buffer containing 100 mM KCl, pH 7.0 in a quartz cuvette was added 10 µL aliquots of a 3 mM solution of d(TTAGGGT)$_4$. After each addition the UV/VIS spectrum was recorded. Pronounced changes in the UV/VIS spectrum of the compound were noted at wavelengths 488 nm (~40% hypochromicity), 510 nm ~50% hyperchromicity), and 548 nm (~200% hyperchromicity).

(C) Compounds may be selected for their ability to interact with human DNA G-quadruplex as indicated by NMR spectroscopy. The imino proton spectrum (9–12 ppm) of a solution of d(TTAGGG)4 in D2O/H2O (10:90) was determined at 500 MHz. Aliquot of N,N'-bis(2-piperdinoethyl)-3,4,9,10-perylenetetracarboxylic acid diimide were added and the imino proton spectrum recorded. At an overall stoichometry of 1:1 the G6 imino resonance becomes significantly broader and shifts >0.2 ppm upfield.

(D) Compounds may be selected for their ability to interact with human DNA g-quadruplex as indicated by an increase in the melting temperature of the G-quadruplex structure. Thermal denaturation of the parallel four-stranded G-quadruplex structure

4.13 Telomerase Inhibition

The cellular process involving maintenance of chromosome telomere length by telomerase activity was recently discovered as a new potential target for chemotherapy. Some of the newly developed agents also showed inhibition of human telomerase in an in vitro telomerase assay. Preliminary results from Taq polymerase primer extension assay and NMR titration suggest that some of the agents inhibit human telomerase activity by interacting with G-quadruplexes of human telomeres. The inventors contemplate that the quinobenzoxazines of the instant invention may serve as telomerase inhibitors. This additional mechanism of action will complement and augment the topoisomerase II inhibitory capabilities of the compounds to produce more potent antineoplastic compounds.

Telomerase inhibition assay results are shown in FIG. 6. The assay used crude HeLa cell extract as the source of human telomerase. It measures the incorporation of $^{32}$P-labeled dGTP into the primer extension of human telomere synthesis (Sun et al., 1998). These results indicate that many of the claimed benzo-annulated compounds are potent telomerase inhibitors. Again, it is contemplated that many of the compounds exhibiting telomerase inhibitory activity also possess the capacity to inhibit topoisomerase II activity. Specific examples of such dual-acting compounds include compounds 2b and 2a (FIG. 3).

4.14 Application of the 2:2 Drug:Mg$^{2+}$ Model for the Design of New Antibiotic Agents The 2:2 drug:Mg$^{2+}$ dimer model can be used equally well to predict that combining two different fluoroquinolones, one optimized for the intercalation role and the other for the external binding mode, will result in novel pairs of drugs useful in treating antibacterial infections. Because bacterial gyrase is also a type II topoisomerase, it is likely that these compounds will interact in like fashion with gyrase. This being the case, the pairs of different fluoroquinolones will present a useful means of controlling the proliferation of bacterial cells.

4.15 Pharmaceutical Formulations and Administration

The invention further comprises the therapeutic treatment of a wide variety of cancers by the administration of an effective dose of one or more quinobenzoxazine analogs, pyridobenzophenoxazines, pyrridonaphthophenoxazines and other related compounds. These compounds also have antibiotic properties and hence the invention also comprises the treatment of bacterial, fugal and parasitic diseases. Where clinical applications are contemplated, it will be necessary to prepare pharmaceutical compositions of drugs in a form appropriate for the intended application. Generally, this will entail preparing compositions that are essentially free of pyrogens, as well as other impurities that could be harmful to humans or animals.

The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra. A preferred route is direct intra-tumoral injection, injection into the tumor vasculature or local or regional admnistration relative to the tumor site.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the compounds developed in the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

4.16 Therapies

One of the major challenges in oncology today is the effective treatment of a given tumor. Tumors are often resistant to traditional therapies. Thus, a great deal of effort is being directed at finding efficous treatment of cancer. One way of achieving this is by combining new drugs with the traditional therapies and is discussed below. In the context of the present invention, it is contemplated that therapies directed against topoisomerases and telomerases could be used in conjunction with surgery, chemotherapy, radiothearpy and indeed gene therapeutic intervention. It also may prove effective to combine therapies targeted to topoisomerases and telomerases with antisense or immunotherapies directed toward tumor marker(s) or other oncogenes or oncoproteins.

"Effective amounts" are those amounts of a candidate substance effective to reproducibly decrease, reduce, inhibit or otherwise abrogate the growth of a cancer cell in comparison to levels in untreated cells. "Effective amounts" are also those amounts of a candidate substance effective to reproducibly decrease, reduce, inhibit or otherwise abrogate the growth of a bacterial or fungal cell in comparison to levels in untreated cells.

It is envisioned that the quinobenzoxazine analogs, pyridobenzophenoxazines, pyrridonaphthophenoxazines and other related compounds will provide therapy for a wide variety of tumors and cancers including skin cancers, connective tissue cancers, adipose cancers, breast cancers, lung cancers, stomach cancers, pancreatic cancers, ovarian cancers, cervical cancers, uterine cancers, anogenital cancers, kidney cancers, bladder cancers, colon cancers, prostate cancers, central nervous system (CNS) cancers, retinal cancer, blood and lymphoid cancers. Since these compounds are also capable of interacting and inhibiting bacterial type II topoisomerases, also called DNA-gyrases, they are useful as antibiotics for the treatment of bacterial and fungal diseases as well.

(i). Combination Cancer Therapies

To kill cells, inhibit cell growth, inhibit metastasis, inhibit angiogenesis or otherwise reverse or reduce the malignant phenotype of tumor cells, the methods of standard therapy discussed below are generally insufficient as tumors are often resistant to several of these agents. Often combining a host of different treatment methods prove most effective in cancer therapy. Further, several AIDS afflicted patients have a higher risk of developing cancers. Combination therapy in these cases is required to treat AIDS as well as the cancer. Using the methods and compounds developed in the present invention, one would generally contact a "target" cell with a quinobenzoxazine analogs and at least one other agent. These compositions would be provided in a combined amount effective to kill or inhibit proliferation of the cell. This process may involve contacting the cells with the topoisomerase-II and/or telomerase based therapy and the other agent(s) or factor(s) at the same time. This may also be achieved by contacting the cell with a single composition or pharmacological formulation that includes both agents, or by contacting the cell with two distinct compositions or formulations, at the same time, wherein one composition includes the topoisomerase-II or telomerase based therapy and the other includes the agent.

Alternatively, the quinobenzoxazine analogs may precede or follow the other agent treatment by intervals ranging from minutes to weeks. In embodiments where the other agent and topoisomerase-II and/or telomerase-based therapy are applied separately to the cell, one would generally ensure that a significant period of time did not expire between the time of each delivery, such that the agent and topoisomerase and/or telomerase-based treatment would still be able to exert an advantageously combined effect on the cell. In such instances, it is contemplated that one would contact the cell with both modalities within about 12–24 h of each other and, more preferably, within about 6–12 h of each other, with a delay time of only about 12 h being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either topoisomerase and/or telomerase-based treatment or the other agent will be desired. Various combinations may be employed, where the topoisomerase-II and/or telomerase-based treatment is "A" and the other agent is "B", as exemplified below:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations are also contemplated. Again, to achieve cell killing, both agents are delivered to a cell in a combined amount effective to kill the cell.

The invention also encompasses the use of a combination of one or more DNA damaging agents, whether chemotherapeutic compounds or radiotherapeutics as described in the section above, together with the quinobenzoxazine analogs. The invention also contempleats the use of the quinobenzoxazine analogs in combination with surgical removal of tumors to treat any remaining neoplastic or meatstasized cells. Further, immunotherapy may be directed at tumor antigen markers that are found on the surface of tumor cells. The invention also contemplates the use of quinobenzoxazine analogs in combination with gene therapy, directed toward a variety of oncogenes, such as, tumor markers, cell cycle controlling genes.

The other agent may be prepared and used as a combined therapeutic composition, or kit, by combining it with the quinobenzoxazines, pyridobenzophenoxazines, pyrridonaphthophenoxazines, and other related compounds developed in this invention as described above. The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

It is proposed that the regional delivery of quinobenzoxazines, pyridobenzophenoxazines, pyrridonaphthophenoxazines, and other related compounds to patients with tumors will be a very efficient method for delivering a therapeutically effective chemical to counteract the clinical disease. Similarly, other chemotherapeutics, radiotherapeutics, gene therapeutic agents may be directed to a particular, affected region of the subjects body. Alternatively, systemic delivery of quinobenzoxazines, pyridobenzophenoxazines, pyrridonaphthophenoxazines, and other related compounds and/or the agent may be appropriate in certain circumstances, for example, where extensive metastasis has occurred.

It also should be pointed out that any of the standard or other therapies may prove useful by themselves in treating a cancer. In this regard, reference to chemotherapeutics and quinobenzoxazine treatment in combination should also be read as a contemplation that these approaches may be employed separately.

When such combination therapy is employed for the treatment of a tumor, the cytotoxic agent may be administered at a dosage known in the art to be effective for treating the tumor. However, the topoisomerase-II or G-quadruplex interaction compounds may produce an additive or synergistic effect with a cytotoxic agent against a particular tumor. Thus, when such combination antitumor therapy is used, the dosage of the topoisomerase and/or G-quadruplex interaction compounds administered may be less than that administered when the cytotoxic agent is used alone. Similarly, for patients afflicted by AIDS, AZT/protease inhibitors will be used with the topoisomerase-II and/or G-quadruplex interaction compounds, or other herein mentioned therapeutic agent(s). Again the dosage of the quinobenzoxazines, pyridobenzophenoxazines, pyrridonaphthophenoxazines, and other related compounds compounds developed herein or other conjunctively utilized agent, may be altered to suit the AIDS treatment.

Preferably, the patient is treated with topoisomerase-II and/or G-quadruplex interaction compounds for about 1 to 14 days, preferably 4 to 14 days, prior to the beginning of therapy with a cytotoxic agent, and thereafter, on a daily basis during the course of such therapy. Daily treatment with the quinobenzoxazine analogs can be continued for a period of, for example, 1 to 365 days after the last dose of the cytotoxic agent is administered. This invention encompasses the use of topoisomerase-II and/or telomerease inhibitors-based cancer therapy for a wide variety of tumors and cancers affecting skin, connective tissues, adipose, breast, lung, stomach, pancreas, ovary, cervix, uterus, kidney, bladder, colon, prostate, anogenital, central nervous system (CNS), retina and blood and lymph.

(ii). Standard Therapies

Described herin are the therapies used as standard or traditional methods for treatment of cancers. The section on chemotherapy describes the use of the compounds developed in the present invention as chemotherapeutic agents in addition to several other well known chemotherapeutic agents. As detailed in the section above, all the methods described below can be used in combination with the compounds developed in the present invention.

a. Chemotherapy: A variety of chemical compounds, also described as "chemotherapeutic agents", function to induce DNA damage, are used to treat tumors. Chemotherapeutic agents contemplated to be of use, include, adriamycin, 5-fluorouracil (5FU), etoposide (VP-16), camptothecin, actinomycin-D, mitomycin, cisplatin (CDDP), hydrogen peroxide, carboplatin, procarbazine, mechlorethamine, cyclophosphamide, ifosfamide, melphalan, chlorambucil, bisulfan, nitrosurea, dactinomycin, daunorubicin, doxorubicin, bleomycin, plicomycin, tamoxifen, taxol, transplatinum, vincristin, vinblastin and methotrexate to mention a few.

Agents that damage DNA include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25–75 mg/m² at 21 day intervals for adriamycin, to 35–50 mg/m² for etoposide intravenously or double the intravenous dose orally.

Agents that disrupt the synthesis and fidelity of nucleic acid precursors and subunits also lead to DNA damage. A number of such agents have been developed, particularly useful are agents that have undergone extensive testing and are readily available. 5-fluorouracil (5-FU), is one such agent that is preferentially used by neoplastic tissue, making it particularly useful for targeting neoplastic cells. Thus, although quite toxic, 5-FU, is applicable with a wide range of carriers, including topical and even intravenous administrations with doses ranging from 3 to 15 mg/kg/day.

Agents that directly cross-link nucleic acids, specifically DNA, are envisaged to facilitate DNA damage leading to a useful antineoplastic treatment. For example, cisplatin, and other DNA alkylating agents may be used. Cisplatin has been widely used to treat cancer, with efficacious doses used in clinical applications of 20 mg/m² for 5 days every three weeks for a total of three courses. Cisplatin is not absorbed orally and must therefore be delivered via injection intravenously, subcutaneously, intratumorally or intraperitoneally.

The topoisomerase-II and/or G-quadruplex inhibitor compounds developed in this invention are chemotherapeutic agents that are cytotoxic by their abilities to inihibit topoisomerase-II and/or telomerase function which are critical for cell replication and maintainence of tumor cell immortality. These compounds also indirectly inhibit DNA polymerases by their strong interactions with topoisomerase-II and DNA G-quadruplex structures in telomeres and gene promoters.

b. Radiotherapy: Radiotherapeutic agents and factors include radiation and waves that induce DNA damage for example, γ-irradiation, X-rays, UV-irradiation, microwaves, electronic emissions, radioisotopes, and the like. Therapy may be achieved by irradiating the localized tumor site with the above described forms of radiations. It is most likely that all of these factors effect a broad range of damage DNA, on the precursors of DNA, the replication and repair of DNA, and the assembly and maintenance of chromosomes.

Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

c. Surgery: Surgical treatment for removal of the cancerous growth is generally a standard procedure for the treatment of tumors and cancers. This attempts to remove the entire cancerous growth. However, surgery is generally combined with chemothrapy and/or radiotherapy to ensure the destruction of any remaining neoplastic or malignant cells.

d. Gene Therapy: Gene therapy based treatments targeted towards oncogenes such as p53, p16, p21, Rb, APC, DCC, NF-1, NF-2, BCRA2, p16, FHIT, WT-1, MEN-I, MEN-II, BRCA1, VHL, FCC, MCC, ras, myc, neu, raf, erb, src, fms, jun, trk, ret, gsp, hst, bcl and abl, which are mutated versions of their normal cellular counterparts in cancerous tissues.

4.17. Screening for Anti-cancer and Anti-biotic Activity

In particular embodiments, one may test the inhibitors by measuring their ability to inhibit growth of cancer cells, to induce cytotoxic events in cancer cells, to induce apoptosis of the cancer cells, to reduce tumor burden and to inhibit metastases. For example, one can measure cell growth according to the MTT assay. A significant inhibition in growth is represented by decreases of at least about 30%–40% as compared to uninhibited, and most preferably, of at least about 50%, with more significant decreases also being possible. Growth assays as measured by the MTT assay are well known in the art. Other assays to measure cell death, apoptosis are well known in the art, for example, Mosmann et al., 1983; Rubinstein et al., 1990 (incorporated herein by reference). Similar assays to measure antibiotic properties to kill bacterial and fungal cells are also well known in the art.

Quantitative in vitro testing of the anti-tumor or antibiotic agents identified herein is not a requirement of the invention as it is generally envisioned that the agents will often be selected on the basis of their known properties or by structural and/or functional comparison to those agents already demonstrated to be effective. Therefore, the effective amounts will often be those amounts proposed to be safe for administration to animals in another context.

5.0 EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

5.1 Materials and Methods

5.2 General Methods for Chemistry

All melting points were recorded on a Thomas-Hoover capillary melting point apparatus and are uncorrected. $^1$H NMR and $^{19}$F NMR data were obtained on a Varian Unity 300 MHz NMR. $^{13}$C NMR data were obtained on a Varian Unity 500 MHz NMR. The chemical shifts are relative to the trace proton, carbon, or fluorine signals of the deuterated solvent. Coupling constants, J, are reported in Hz and refer to apparent peak multiplicity and not true coupling constants. Mass spectroscopic studies were performed by the Mass Spectroscopy Center of The University of Texas at Austin. Elemental analysis of C, H, N was done by Quantitative Technologies Inc., White House, N.J. Flash column chromatography was performed on silica gel 60, 230–400 mesh, purchased from Spectrum. All starting materials were obtained from commercial sources unless otherwise specified in the experimental.

5.3 Materials, Enzymes, and Drugs

Quinobenzoxazine A-62176 was prepared according to the literature (Chu and Maleczka Jr., 1987). Norfloxacin was purchased from Sigma. Psorospermin was obtained from Dr. John M. Cassady (The Ohio State University). Electrophoretic reagents (acrylamide, N,N'-methylenebisacrylamide, ammonium persulfate) were from J. T. Baker, Inc. and N,N,N',N'-tetramethylethylenediamine was from Fisher. T4 polynucleotide kinase, Drosophila topoisomerase II, and [γ-$^{32}$P]ATP were purchased from Amersham.

5.4 Preparation and End-Labeling of Oligonucleotides 80-base oligonucleotides for the topo II studies were synthesized on an Expedite 8900 Nucleic Acid Synthesis System (PerSeptive Biosystems) using the phosphoramidite method. The oligonucleotides were eluted out of the column by aqueous ammonia and deprotected at 75° C. for 1 hr, followed by a 12% denaturing polyacrylamide gel purification. The 5'-end-labeled single-stranded oligonucleotides were obtained by kination reaction using T4 polynucleotide kinase and [γ-$^{32}$P]ATP. The labeled strands were then annealed with the complementary strands and purified on an 8% native polyacrylamide gel.

5.5 Topo II Cleavage Reactions

5'$^{32}$P-labeled DNA was incubated with Drosophila topo II in 20 μl of a reaction buffer [10 mM imidazole-HCl (pH 6.0), 10 mM MgCl$_2$, 50 mM KCl, and 1 mM ATP] at 30° C. for 10 min in the presence of various amounts of A-62176. Reactions were terminated by adding SDS to 1%, and topo II was removed by proteinase K digestion (100 μg/ml) at 42° C. for 1 hr followed by phenol/chloroform extraction and ethanol precipitation.

5.6 Competition Studies

5'$^{32}$P-labeled DNA was incubated with Drosophila topo II in the same buffer as the one in the topo II cleavage reaction in the presence of various amounts of either A-62176, Norfloxacin, or both. The incubation reactions took place at 30° C. for 10 min before 10 μM (final concentration) of psorospermin was added to the mixtures. The reactions were continued for an additional 5 min and then terminated by adding 5 μg of calf thymus DNA, followed by heating at 95° C. for 15 min. In the presence of piperidine, this procedure induces strand breakage at the drug modification sites (Hansen et al., 1996). The samples were subjected to phenol/chloroform extraction followed by ethanol precipitation.

5.7 Gel Electrophoresis and Quantification

The samples were loaded on a 12% denaturing sequencing gel. The dried gels were exposed on both X-ray film and phosphor screen. Imaging and quantification were performed by a PhosphorImager and ImageQuaNT 4.1 software from Molecular Dynamics.

5.8 Materials for Biochemistry

Kinetoplast DNA (KDNA), human topoisomerase II (170 KDa form), and DNA Unwinding Kit including supercoiled pHOT1 DNA, relaxed DNA marker, buffers, and human topoisomerase I were purchased from TopoGEN, Inc. Agarose was purchased from Fisher. Quinobenzoxazine A-62176 (S-enantiomer) was provided by Abbott Laboratories or prepared by published procedure (Chu and Maleczka, Jr., 1987).

5.9 Decatenation Assay 0.25 μg of KDNA was incubated with various concentrations of the quinobenzoxazines in a 20-μl reaction mixture containing 50 mM Tris-HCl (pH 8), 120 mM KCl, 10 mM MgCl$_2$, and 0.5 mM each of ATP, dithiothreitol, and 30 mg/ml BSA for 10 min. Two units of human topoisomerase II (170 KDa form) were added to the mixture, which was then incubated at 37° C. for 30 min. The reaction was terminated with 0.1 volume of stop buffer (5% sarkosyl, 0.025% bromophenol blue, and 50% glycerol). The decatenation products were analyzed on 1% agarose gels run with 0.5 μg/ml ethidium bromide. The gels were scanned by FluoroImager and analyzed by ImageQuaNT software (Molecular Dynamics).

5.10 DNA Unwinding Assay

A 22 μl mixture of 0.25 μg of supercoiled pHOT1 DNA, 5 units of topoisomerase I in topoisomerase I buffer (provided with the kit) was incubated at 37° C. for 30 min. Two μl of various concentrations of drug was added, and the incubation was continued for another 30 min. The reactions were terminated by addition of SDS to 1%. Proteinase K was added to the reaction mixtures to ca. 50 μg/ml, and the reaction mixtures were incubated for 15–20 min at 56° C. After adding 0.1 volume of 10×gel loading buffer, the reaction mixtures were extracted with an equal volume of CIA (Chloroform:isoamyl Alcohol; 24:1). The samples were loaded on an 1% agarous gel that was cast in TPE buffer (36 mM Tris-HCl, pH 7.8, 1 mM EDTA, 30 mM NaH$_2$PO$_4$) and 0.2 μg/ml Chloroquine. The gel was run in TPE buffer at room temperature at 10 volts for 20 h, destained in water for 15 min, stained in 0.05 μg/ml ethidium bromide for 15 min, and destained again in water for 15 min. The gel was then photographed, scanned by FluoroImager, and analyzed by ImageQuaNT software (Molecular Dynamics).

5.11 Cancer Cell Growth Inhibition Assays

Exponentially growing cells in 0.1 ml medium were seeded on Day 0 in 96-well microtiter plates. On Day 1, 0.1-ml aliquots of medium containing graded concentrations test agent were added in duplicate to the cell plates. After incubation at 37° C. in a humidified incubator, the plates were centrifuged briefly (1–2 min at 1000 rpm), and 100 μl of the growth medium was removed. Cell cultures were incubated with 50 μl of 3-(4,5-dimethylthiazyl-2-yl)-2,5-diphenyltetrazolium bromide MTT, 1 mg/ml in Dubecco's PBS for 4 h at 37° C. The resulting purple formazan precipitate was solubilized with 200 μl of 0.4 N HCl in isopropyl alcohol. Absorbance was quantitated using a Bio-Rad Model 3550 microplate reader at a test wavelength of 570 nm and a reference wavelength of 630 nm. Absorbance values were transferred to a 486 personal computer, and the IC$_{50}$ values were determined using the computer program EZ-ED50 (Chen et al., 1993).

5.12 DNA Synthesis Arrest Assay

This assay is similar to that described by Han and co-workers (Han et al., 1999). Briefly, primers (24 nM) labeled with [γ-$^{32}$P] were mixed with template DNA (12 nM)) in a Tris-HCl buffer (10 mM Tris, pH 8.0) containing K$^+$ (50 mM for the HT4 template) and denatured by heating at 90° C. for 5 min. After cooling down to room temperature, 2b was added at various concentrations and incubated at room temperature for 15 min. The primer extension reactions were initiated by adding dNTP (final concentration 100 μM), MgCl$_2$ (final concentration 3 μM), and Taq DNA polymerase (2.5 U/reaction, Boehringer Mannheim). The products were separated on a 12% polyacrylamide sequencing gel. The gels were then dried and visualized on a PhosphorImager (Molecular Dynamics model 445 S1).

5.13 Telomerase Inhibition Assay

The assay was performed by using 5'-end biotinylated d[TTAGGG]$_3$ as the telomere primer. Reaction mixtures (20 µl) containing 5 µl cell lysate (S-100), 50 mM Tris-OAc (pH 8.5), 50 mM K-OAc, 1 mM MgCl$_2$, 5 mM BME, 1 mM spermidine, 1 µM telomere primer, 1.5 µM [α-$^{32}$P]-dGTP (800 Ci/mmol), 1 mM dATP, and 1 mM dTTP were incubated at 37° C. for 1 hr, and the reactions were terminated by adding 20 µl of [$^{32}$P ATP]-labeled streptavidin-coated Dynabeads suspension containing 10 mM Tris-HCl (pH 7.5), 1 mM EDTA, 2M KCl, and a 500 cpm biotinylated internal control. Streptavidin-coated Dynabeads bind selectively to the desired target (5'-biotinylated primer), forming a magnetic bead-targeted complex. The complex was separated from the suspension using a Dynal MPC magnet and washed several times with 2×SSC buffer containing 0.1% SDS to eliminate [α-$^{32}$P]-dGTP background. Telomerase reaction products were separated from the magnetic beads by protein denaturation with 5.7 M guanidine-HCl at 90° C. for 30 min. After ethanol precipitation, products were resolved on denaturating 10% polyacrylamide gel.

5.14 Example 1

Solid Phase Synthesis of Quinobenzoxazine Analogues (FIG. 4A and FIG. 4B)

Ethyl 2,3,4,5-tetrafluorobenzoylacetate (a compound of formula (1) wherein R$_1$=ethyl, as shown in FIG. 4A and FIG. 4B) was loaded on the resin (solid support) by a transesterification reaction with p-benzyloxybenzyl alcohol of Wang resin (1) as shown in FIG. 4A and FIG. 4B. Two equivalents of ethyl 2,3,4,5-tetrafluorobenzoylacetate to the hydroxy group of the resin (1.1 mmol/g) were used, and the reaction was completed by refluxing in toluene in the presence of a catalytic amount (5%) of 4-dimethylaminopridine (DMAP) for 36 h. (The reaction time can be shortened if more equivalents of ethyl 2,3,4,5-tetrafluorobenzoylacetate are used.) The loading level was determined by mass balance and elemental analysis of fluorine.

The solid-bound β-ketoester (a compound of formula (II), shown in FIG. 4A and FIG. 4B) was then treated with 2.5 equivalents of dimethylformamide dimethyl acetal in a peptide synthesis vessel in THF at 22° C. overnight. After removing the excess reagents and washing the resin with dichloromethane, the resin was treated with 2–4 equivalents of various o-hydroxy aniline derivatives (a compound of formula (III) wherein R$_2$=CH$_2$NHCO$_2$CH$_2$CH$_2$Si(CH$_3$)$_3$ or H, in FIG. 4A and a compound of formula (XIII) wherein Y=—CH$_2$CH$_2$— or —CHCH—, in FIG. 4B) in the presence of two equivalents of pyridine to generate a resin-bound enaminoketoester (a compound of formula (IV) wherein R$_2$=CH$_2$NHCO$_2$CH$_2$CH$_2$Si(CH$_3$)$_3$ or H, in FIG. 4A and a compound of formula (XIV) wherein Y=—CH$_2$CH$_2$— or —CHCH—, in FIG. 4B) in THF. This step was a branch point so that diversified scaffold could be made.

The benzylic amino group was protected as a 2-trimethylsilylethyl carbamate (Teoc), which was a cross-protection strategy that differentiated this amino group from the t-Boc-protected aminopyrrolidine group or other t-Boc-protected amino-group-containing bases that was introduced later in some cases. A double cyclization step using four equivalents of TMG in THF and stirring the mixture at 0–150° C., preferably at 40–70° C., rendered the tetracyclic scaffold (a compound of formula (V) wherein R$_2$=CH$_2$NHCO$_2$CH$_2$CH$_2$Si(CH$_3$)$_3$ or H, in FIG. 4A and a compound of formula (XV) wherein Y=—CH$_2$CH$_2$— or —CHCH—, in FIG. 4B). Regio-selective nucleophilic substitution of the fluorine by cyclic nitrogen-containing bases (a compound of formula (IV) wherein A=3-((tert-butoxy) carbonylamino)pyrrolidin-1-yl, 3-acetylamidopyrrolidin-1-yl or N-4-(tert-butoxy)carbonylpiperazin-1-yl, in FIG. 4A and FIG. 4B) generated the quinobenzoxazine analogues (a compound of formula (VII) wherein R$_2$=CH$_2$NHCO$_2$CH$_2$CH$_2$Si(CH$_3$)$_3$ or H, and B=3-aminopyrrolidin-1-yl, 3-acetylamidopyrrolidin-1-yl or piperazin-1-yl, in FIG. 4A and a compound of formula (XVI) wherein Y=—CH$_2$CH$_2$— or —CHCH—, in FIG. 4B). This was another branch point at which different derivatives can be synthesized.

The benzylic amino group-containing analogues were further derivatized by deprotection of the benzylic amino group with tetrabutylamonium fluoride in THF at 0–10° C., preferably at 10–40° C., to give resin-bound amine (a compound of formula (IX) wherein R$_2$=CH$_2$NH$_2$, in FIG. 5A), and coupling with varieties of amino acids, acylating, alkylating agents to give a compound of formula (XI) (whrein R$_3$=COCH$_3$). The cleavage of the final products from the resin was accomplished by treating the resin with 50% TFA in dichloromethane at 0–8° C., preferably 10–40° C. Trituration of the concentrated TFA solution in ethanol yielded the final products (a compound of formula (VIII) wherein R$_2$=H or acid-insensitive alkyl or functional group, (XII) wherein B=3-aminopyrrolidin-1-yl, 3-acetylamidopyrrolidin-1-yl or piperazin-1-yl, in FIG. 5A and a compound of formula (XVII) wherein Y=—CH$_2$CH$_2$— or —CHCH—, and B=3-aminopyrrolidin-1-yl, in FIG. 4B) as an amorphous yellow solid.

Because all the synthetic intermediates of quinobenzoxazines contain fluorine atoms, a gel-phase $^{19}$F NMR and $^{13}$C NMR technique was developed to monitor the reaction processes. The resin-bound 2,3,4,5-tetrafluorobenzoylacetate (a compound of formula (II)) showed two sets of four peaks due to the enolization of the β-ketoester. The enaminoketoester (a compound of formula (IV)) showed one set of four peaks that was different from the starting material. After the double cyclization, only two peaks were observed as in a compound of formula (V). The nucleophilic substitution generated a product (a compound of formula (VII)) with only one $^{19}$F NMR signal. The deprotection of the benzylic amino group can be monitored by the $^{13}$C NMR of the trimethylsilyl group at about 0 ppm. The sample of gel-phase NMR was typically prepared by suspending the resin in a 5% DMSO-d$_6$ in N-methylpyrrolidinone for $^{19}$F NMR and in deuterated dichloromethane for $^{13}$C NMR. All the solid-phase synthesis steps were monitored by the gel-phase $^{19}$F NMR and $^{13}$C NMR, and the reactions were forced to completion by adjusting the reaction conditions such as temperature, time, and reagents concentrations. The nucleophilic substitution step was the one that led to decreased mass balance, because $^{19}$F NMR of the reaction mixture indicated not only a broad peak for the resin bound product, but also a single sharp peak for the cleaved product. The gel-phase $^{19}$F NMR and $^{13}$C NMR also indicated that prolonging the reaction time for the deprotection step of the benzylic amino group with tetrabutylarnonium fluoride would lead to cleavage of the product from the resin.

5.14.1 Wang Resin-bound β-ketoester (a Compound of Formula (II) in FIG. 4A)

Gel-phase $^{19}$F NMR (5% DMSO-d6 and N-metylpyrrolidinone): δ 136.6 (br, 1F), −138.1 (br, 1F), −148.7 (br, 1F), −155.1 (br, 1F).

5.14.2 Wang Resin-bound Enaminoketoester (a Compound of Formula (IV) wherein $R_2$= $CH_2NHCO_2CH_2CH_2Si(CH_3)_3$, in FIG. 4A)

Gel-phase $^{19}$F NMR (5% DMSO-d6 and N-metylpyrrolidinone): δ −140.9 (br, 1F), −142.7 (br, 1F), −157.1 (br, 1F), −157.6 (br, 1F).

5.14.3 Wang Resin-bound 1,2-Difluoro-quinobenzoxazine Scaffold (a Compound of Formula (V) wherein $R_2$=$CH_2NHCO_2CH_2CH_2Si$ $(CH_3)_3$).

Gel-phase $^{19}$F NMR (5% DMSO-d6 and N-metylpyrrolidinone): δ −134.6 (br, 1F), −152.3 (br, 1F).

5.14.4 Wang Resin-bound 2-Monofluoro-quinobenzoxazine Analogues (a Compound of Formula (VII) wherein $R_2$=$CH_2NHCO_2CH_2CH_2Si$ $(CH_3)_3$).

Gel phase $^{19}$F NMR (5% DMSO-d6 and N-metylpyrrolidinone): δ −121.2 (br, 1F).

1-(S)-(3-Acetylaminopyrrolidin-1-yl)-2-fluoro-4-oxo-4H-9-acetylaminomethyl-pyrido[3,2,1-k,l] phenoxazine-5-carboxylic Acid TFA Salt (a Compound of Formula (XII) wherein B=(S)-(3-Acetylaminopyrrolidin-1-yl), $R_3$=$COCH_3$)

Yield=27%. $^1$H NMR (DMSO-d$_6$) δ 9.04 (s, 1H), 8.44 (b, 1H), 8.17 (d, J=6.1 Hz, 1H), 8.10 (b, 1H), 7.92 (d, J=8.1 Hz, 1H), 7.45 (d, $J_{F-H}$=13.8 Hz, 1H), 7.07 (d, J=8.1 Hz, 1H), 7.09 (s, 1H), 4.2–4.3 (b m, 3H), 3.7–3.9 (b m, 4H), 2.07 (s, 3H), 2.06 (b, 1H), 1.83 (s, 3H), 1.81 (b, 1H), $^{19}$F NMR (DMSO-d$_6$) δ −124 (d, $J_{H-F}$=14.1 Hz), HRMS Calculated for $C_{26}H_{26}N_4O_5F$ 495.1680, found 495.1662.

1-(S)-(3-Acetylaminopyrrolidin-1-yl)-2-fluoro-4-oxo-4H-9-aminomethyl-pyrido[3,2,1-k,l] phenoxazine-5-carboxylic Acid TFA Salt (a Compound of Formula (XII) wherein B=(S)-(3-Acetylaminopyrrolidin-1-yl), $R_3$=H)

Yield=34%. $^1$H NMR (DMSO-d$_6$) δ 9.10 (s, 1H), 8.30 (b, 4H), 8.09 (d, J=8.7 Hz, 1H), 7.49 (d, $J_{F-H}$=14.1 Hz, 1H), 7.37 (s, 1H), 7.29 (d, J=8.7 Hz, 1H), 4.30 (b m, 1H), 4.00 (b m, 2H), 3.97 (b, 1H), 3.84 (b m, 1H), 3.74 (b m, 2H), 2.07 (m, 1H), 1.84 (m, 1H), 1.83 (s, 3H), $^{19}$F NMR (DMSO-d$_6$) δ −124 (d, $J_{H-F}$=11.8 Hz).

1-(S)-(3-Aminopyrrolidin-1-yl)-2-fluoro-4-oxo-4H-pyrido[3,2,1-k,l]phenoxazine-5-carboxylic Acid TFA Salt (a Compound of Formula (VIII) wherein B=(S)-(3-Aminopyrrolidin-1-yl), $R_2$=H)

Yield=25%. $^1$H NMR as presented in reference 2 (Chu and Malezka, Jr., 1987).

1-(S)-(3-Aminopyrrolidin-1-yl)-2-fluoro-4-oxo-4H-pyrido[3,2,1-k,l]-8H,9H-naphtho[1,2-g] phenoxazine-5-carboxylic Acid TFA Salt and 1-(S)-(3-Aminopyrrolidin-1-yl)-2-fluoro-4-oxo-4H-pyrido[3,2,1-k,l]-13H,14H-naphtho[1,2-f]phenoxazine-5-carboxylic Acid TFA Salt Salt (Compounds of Formula (XVII) wherein B=(S)-(3-Aminopyrrolidin-1-yl), Y=—$CH_2CH_2$—)

Yield=40%. The titled compounds were synthesized as a 3:1 mixture, the first compound: $^1$H NMR (DMSO-d$_6$) δ 9.15 (s, 1H), 8.2 (b, 1H), 8.0 (s, 1H), 7.83 (d, J=7.8 Hz, 1H), 7.69 (s, 1H), 7.49 (d, $J_{F-H}$=13.5 Hz, 1H), 7.31 (bm, 3H), 3.8–4.0 (bm, 5H) (buried under $H_2O$ peak), 2.85 (bs, 4H), 2.30 (m, 1H), 2.05 (m, 1H), $^{19}$F NMR (DMSO-d$_6$) δ −123 (d, $J_{H-F}$=15.2 Hz), the second compound: $^{19}$F NMR (DMSO-d$_6$) δ −124 (d, $J_{H-F}$=15.2 Hz), HRMS Calcd for $C_{28}H_{23}N_3O_4F$ 484.1673, found 484.1669.

1-(S)-(3-Aminopyrrolidin-1-yl)-2-fluoro-4-oxo-4H-pyrido[3,2,1-k,l]-naphtho[1,2-g]phenoxazine-5-carboxylic Acid TFA Salt (12) and 1-(S)-(3-Aminopyrrolidin-1-yl)-2-fluoro-4-oxo-4H-pyrido[3,2,1-k,l]-naphtho[1,2-f]-phenoxazine-5-carboxylic Acid TFA Salt (Compounds of Formula (XVII) wherein B=(S)-(3-Aminopyrrolidin-1-yl), Y=—CH=CH—)

Yield=22%. The titled compounds were synthesized as a 3:1 mixture, the first compound: $^1$H NMR (DMSO-d$_6$) δ 9.20 (s, 1H), 8.61 (b, 1H), 8.55 (s, 1H), 8.38 (s, 1H), 8.27 (b, 3H), 7.79–7.86 (m, 3H), 7.59–7.68 (m, 3H), 7.38 (d, $J_{F-H}$= 13.5 Hz, 1H), 3.75–4.12 (b m, 5H), 2.36 (m, 1H), 2.1 (m, 1H), $^{19}$F NMR (DMSO-d$_6$) δ −123 (d, $J_{H-F}$=13.8 Hz), the second compound: $^{19}$F NMR (DMSO-d$_6$) δ −122 (d, $J_{H-F}$= 13.8 Hz), HRMS Calcd for $C_{28}H_{21}N_3O_4F$ 482.1516, found 482.1514.

5.15 Example 2 (FIG. 4C)

Synthesis of Pyridobenzophenoxazines

Ethyl 3-((2-Hydroxynaphthyl)amino)-2-((2,3,4,5-tetrafluorophenyl)carbonyl)prop-2-enoate (Compound 5 of FIG. 4C)

Ethyl 2,3,4,5-tetrafluorobenzoylacetate was treated with triethyl orthofomate and acetic anhydride, then with different aminonaphthols in the presence of pyridine to generate an aminoketoacid. The solution of ethyl 2,3,4,5-tetrafluorobenzoylacetate (1.10 g, 4.18 mmol) in triethylorthoformate (1 ml, 6.06 mmol) and acetic anhydride (1.8 ml, 19 mmol) was heated and stirred at 130° C. for 4 h. During the process, the formed ethyl acetate was removed. The mixture was then distilled under vacuum to yield an orange oil, which was dissolved in 30 ml dichloromethane. 1-aminonaphthalen-2-ol hydrogen chloride (90% pure from Aldrich) (1.36 g, 6.26 mmol), premixed with 2 equivalent of pyridine, was added to the dichloromethane solution, and the mixture was stirred overnight at 22° C. After the solvent was removed under reduced pressure, the remaining residue was absorbed on silica gel and subjected to flash column chromatography (gradient ethylacetate:hexanes=8:4) that yield a bright yellow powder (1.69 g). Yield=93%. $^1$H NMR (CDCl$_3$) δ 1.02 (t, J=7.2 Hz, 3H), 4.01 (q, J=7.2 Hz, 2H), 4.10 (m, 1H), 7.34 (d, J=9.0 Hz, 1H), 7.41 (m, 1H), 7.60 (m, 2H), 7.82 (8, 2H), 7.91 (d, J=8.1 Hz, 1H), 8.54 (b, 1H).

Ethyl 3-((1-Hydroxy(2-naphthyl))amino)-2-((2,3,4,5-tetrafluorophenyl)carbonyl)prop-2-enoate (Compound 6 of FIG. 4C)

The titled compound was synthesized in a similar way as compound 5 as a yellow amorphous solid. Yield=90%. $^1$H NMR (CDCl$_3$) δ 1.14 (t, J=7.2 Hz, 3H), 4.13 (q, J=7.2 Hz, 2H), 6.86 (m, 1H), 7.40–7.64 (b m, 4H), 7.80 (m, 1H), 7.93 (d, J=8.4 Hz, 1H), 8.69–8.79 (m, 1H).

Ethyl 3-((3-Hydroxy(2-naphthyl))amino)-2-((2,3,4,5-tetrafluorophenyl)carbonyl)prop-2-enoate (Compound 7 of FIG. 4C)

The titled compound was synthesized in a similar way as compound 5 as a yellow amorphous solid. Yield=90%. $^1$H NMR (CDCl$_3$) δ 1.08 (t, J=7.2 Hz, 3H), 4.07 (q, J=7.2 Hz, 2H), 7.30–7.40 (m, 3H), 7.51 (m, 1H), 7.71 (d, J=7.8 Hz, 1H), 7.85 (d, 7.0 Hz, 1H), 8.20 (b, 1H), 8.87 (b, 1H).

Ethyl 1,2-Difluoro-4-oxo-4H-pyrido[3,2,1-k,l]-benzo[h]phenoxazine-5-carboxylate (Compound 8 of FIG. 4C)

Ethyl-3-((2-hydroxynaphthyl)amino)-2-((2,3,4,5-tetrafluorophenyl)carbonyl)prop-2-enoate (0.11 g, 0.25 mmol) (compound 5 in FIG. 4C) and NaH (60% in mineral oil) (23.2 mg, 0.58 mmol) were mixed with freshly distilled THF and stirred at −78° C. for 15 min. The mixture was let to warmed to room temperature gradually and then heated at 65° C. for 30 min. The excess NaH was quenched by addition of 30 ml of methanol. The solution was evaporated to dryness and the product was purified through flash column chromatography, yielding a yellow powder (0.094 g). Yield=93%. $^1$H NMR (CDCl$_3$) δ 1.42 (t, J=7.2 Hz, 3H), 4.42 (q, J=7.2 Hz, 2H), 7.35 (d, J=8.7 Hz, 1H), 7.53 (t, J=7.2 Hz, 1H), 7.64 (t, J=9.0 Hz, 1H), 7.76 (dd, J$_{F-H}$=9.9, 7.5 Hz, 1H), 7.80 (d, J=8.7 Hz, 1H), 7.89 (d, J=7.5 Hz, 1H), 8.20 (d, J=8.7 Hz, 1H), 8.36 (s, 1H).

Ethyl 1,2-Difluoro-4-oxo-4H-pyrido[3,2,1-k,l]-benzo[f]phenoxazine-5-carboxylate (Compound 9 of FIG. 4C)

The titled compound was synthesized in a similar way as compound 8 as a yellow amorphous solid. Yield 60%. $^1$H NMR (CDCl$_3$) δ 1.46 (t, J=7.2 Hz, 3H), 4.45 (q, J=7.2 Hz, 1H), 7.50 (d, J=9.1 Hz, 1H), 7.54 (t, J=7.5 Hz, 1H), 7.60 (t, J=7.5 Hz, 1H), 7.66 (d, J=9.1 Hz, 1H), 7.74 (dd, J$_{F-H}$=10.8, 7.5 Hz, 1H), 7.77 (d, J=8.4 Hz, 1H), 8.18 (d, J=8.4 Hz, 1H), 8.93 (s, 1H).

Ethyl 1,2-Difluoro-4-oxo-4H-pyrido[3,2,1-k,l]-benzo[g]phenoxazine-5-carboxylate (Compound 10 of FIG. 4C)

The titled compound was synthesized in a similar way as compound 8 as a light yellow amorphous solid. Yield=52%. $^1$H NMR (CDCl$_3$) δ 1.48 (t, J=7.2 Hz, 3H), 4.49 (q, J 7.2 Hz, 2H), 7.51 (m, 2H), 7.62 (s, 1H), 7.75 (m, 1H), 7.79–7.85 (m, 2H), 7.89 (s, 1H), 9.19 (s, 1H).

Ethyl 1-(3-((tert-Butoxy)carbonylamino)pyrrolidin-1-yl)-2-fluoro-4-oxo-4H-pyrido[3,2,1-k,l]-benzo[h]phenoxazine-5-carboxylate (a Compound of Formula (XVIII, FIG. 4C) wherein A=3-((tert-Butoxy)carbonylamino)pyrrolidin-1-yl)

Ethyl 1,2-difluoro-4-oxo-4H-pyrido[3,2,1-k,l]-benzo[h]phenoxazine-5-carboxylate (8) (0.10 g, 0.25 mmol) and racemic 3-(tert-butoxycarbonylamino)pyrrolidine (0.14 g, 0.77 mmol) were dissolved in 15 ml pyridine, and the mixture was stirred under argon at 110° C. for 36 h. After removing the pyridine, the residue was purified using flash column chromatography (dichloromethane:ethylacetate= 2:3) to yield a yellow powder (0.12 g) Yield=91%. $^1$H NMR (CDCl$_3$) δ 1.41 (t, J=7.2 Hz, 3H), 1,46 (s, 9H), 1.94 (m, 1H), 2.20 (m, 1H), 3.52 (b m, 1H), 3.65 (m, 1H), 3.81 (m, 1H), 3.92 (m, 1H), 4.33 (b m, 1H), 4.40 (q, J=7.2 Hz, 2H), 5.05 (b, 1H), 7.18 (d, J=8.7 Hz, 1H), 7.45 (t, J=7.8 Hz, 1H), 7.54 (t, J=7.8 Hz, 1H), 7.56 (d, J$_{F-H}$=13.5 Hz, 1H), 7.69 (d, J=8.7 Hz, 1H), 7.83 (d, J=8.7 Hz, 1H), 8.09 (d, J=8.7 Hz, 1H), 9.12 (s, 1H).

Ethyl 1-(3-((tert-Butoxy)carbonylamino)pyrrolidin-1-yl)-2-fluoro-4-oxo-4H-pyrido[3,2,1-k,l]-benzo[f]phenoxazine-5-carboxylate (a Compound of Formula (XIX, FIG. 4C) wherein A=3-((tert-Butoxy)carbonylamino)pyrrolidin-1-yl)

The titled compound was synthesized in a similar way as the compound of formula (XVIII) (wherein A=3-((tert-butoxy)carbonylamino)pyrrolidin-1-yl) as a yellow amorphous solid. $^1$H NMR (CDCl$_3$) δ 1.42 (t, J=7.2 Hz, 3H), 1,48 (s, 9H), 2.02 (m, 1H), 2.28 (m, 1H), 3.55 (b m, 1H), 3.65 (m, 1H), 3.87 (b m, 1H), 3.92 (m, 1H), 4.33 (b m, 1H), 4.39 (q, J=7.2 Hz, 2H), 5.24 (m, 1H), 7.37 (d, J=9.0 Hz, 1H), 7.51–7.61 (m, 3H), 7.78 (d, j=7.8 Hz, 1H), 7.99 (d, J=7.8 Hz, 1H), 8.71 (s, 1H).

Ethyl 1-(3-((tert-Butoxy)carbonylamino)pyrrolidin-1-yl)-2-fluoro-4-oxo-4H-pyrido[3,2,1-k,l]-benzo[g]phenoxazine-5-carboxylate (a Compound of Formula (XX, FIG. 4C) wherein A=3-((tert-Butoxy)carbonylamino)pyrrolidin-1-yl)

The titled compound was synthesized in a similar way as the compound of formula (XVIII) (wherein A=3-((tert-butoxy)carbonylamino)pyrrolidin-1-yl) as a yellow amorphous solid. $^1$H NMR (CDCl$_3$) δ 1.45 (t, J=7.2 Hz, 3H), 1,48 (s, 9H), 1.96 (m, 1H), 2.22 (m, 1H), 3.54–3.70 (b m, 2H), 3.86–4.02 (b m, 2H), 4.33 (b m, 1H), 4.44 (q, J=7.2 Hz, 2H), 5.22 (b, 1H), 7.34 (s, 1H), 7.40–7.48 (m, 2H), 7.55 (d, J$_{F-H}$=13.5 Hz, 1H), 7.65 (d, J=7.8 Hz, 1H), 7.67 (s, 1H), 7.72 (d, J=7.8 Hz, 1H), 8.93 (s, 1H).

1-(3-Aminopyrrolidin-1-yl)-2-fluoro-4-oxo-4H-pyrido[3,2,1-k,l]-benzo[h]-phenoxazine-5-carboxylic Acid (a Compound of Formula (XXI, FIG. 4C) wherein B=3-Aminopyrrolidin-1-yl)

Ethyl-1-(3-((tert-butoxy)carbonylamino)pyrrolidin-1-yl)-2-fluoro-4-oxo-4H-pyrido[3,2,1-k,l]-benzo[h]phenoxazine-5-carboxylate (a compound of formula (XVIII) wherein A=3-((tert-butoxy)carbonylamino)pyrrolidin-1-yl) (77 mg, 0.138 mmol) was mixed with 3 ml ethanol and 1 ml 1N KOH. The mixture was refluxed for 30 min. 3 ml 2N HCl and 2 ml ethanol were then added to the mixture, and it was refluxed for 4 h. After the reaction mixture was cooled down slowly, a yellow powder was obtained by filtration, washing with water and ethanol, and drying under vacuum (65 mg). Yield=94%. m.p.>225° C. (decompose), $^1$H NMR (CF$_3$COOD) δ 2.65 (b m, 2H), 4.10 (b m, 1H), 4.37–4.54 (b m, 4H), 7.44 (d, J=9.0 Hz, 1H), 7.66 (t, J=7.5 Hz, 1H), 7.78 (t, J=7.5 Hz, 1H), 7.90 (d, J=13.0 Hz, 1H), 8.03 (d, J=8.5 Hz, 1H), 8.08 (d, J=9.0 Hz, 1H), 8.20 (d, J=8.5 Hz, 1H), 9.90 (s, 1H); $^{13}$C NMR (DMSO-d$_6$) δ 29.3, 49.0, 49.1, 54.3, 104.8 (d, J$_{C-F}$=24.6 Hz), 106.8, 114.1, 116.6 (d, J$_{C-F}$=9.2 Hz), 117.0, 118.5, 120.1, 123.8, 125.8, 128.5, 128.8 (d, J$_{C-F}$=14.2 Hz), 129.4, 130.4 (d, J$_{C-F}$=20.1 Hz), 131.9, 134.3 (d, J$_{C-F}$= 9.2 Hz), 143.7, 145.4, 153.0 (d, J$_{C-F}$=248 Hz), 165.4, 175.9, 180.2; $^{19}$F NMR (CF$_3$COOD) δ −113.2 (d, J$_{F-H}$=12.7 Hz); HRMS Calcd for C$_{24}$H$_{19}$FN$_3$O$_4$ 432.1360, found 432.1375; Anal. racemic compound (a compound of formula (XXI) wherein B=3-aminopyrrolidin-1-yl) (C$_{24}$H$_{18}$FN$_3$O$_4$.HCl.1/3H$_2$O) C, H, N. R-compound (a compound of formula (XXI) wherein B=(R)-3-aminopyrrolidin-1-yl): (C$_{24}$H$_{18}$FN$_3$O$_4$.HCl.3/2H$_2$O) C, H, N. S-compound (a compound of formula (XXI) wherein B=(S)-3-aminopyrrolidin-1-yl): (C$_{24}$H$_{18}$FN$_3$O$_4$.HCl.4/3H$_2$O) C, H, N.

1-(3-Aminopyrrolidin-1-yl)-2-fluoro-4-oxo-4H-pyrido[3,2,1-k,l]-benzo[f]-phenoxazine-5-carboxylic Acid Acid (a Compound of Formula (XXII, FIG. 4C) wherein B=3-Aminopyrrolidin-1-yl)

The titled compound was synthesized in a similar way as the compound of formula (XXI) (wherein A=3-aminopyrrolidin-1-yl) as a yellow amorphous solid. m.p.>207° C. (decompose), $^1$H NMR (CF$_3$COOD) δ 2.69 (b m, 2H), 4.19 (b m, 1H), 4.40–4.67 (b m, 4H), 7.73–7.81 (m, 3H), 7.87–7.99 (m, 3H), 8.20 (m, 1H), 9.47 (s, 1H); $^{13}$C NMR (DMSO-d$_6$) δ 29.4, 49.0, 49.3, 54.5, 104.6 (d, J$_{C-F}$= 24.8 Hz), 106.8, 114.1, 116.9 (d, J$_{C-F}$=9.2 Hz), 118.8, 121.4, 122.6, 125.2, 126.2, 127.6, 128.0 (d, J$_{C-F}$=10.6 Hz), 128.6 (d, J$_{C-F}$=14.2 Hz), 132.6, 134.7 (d, J$_{C-F}$=8.7 Hz), 137.7, 138.7, 154.0 (d, J$_{C-F}$=248 Hz), 165.4, 175.4, 180.2; $^{19}$F NMR (CF$_3$COOD) δ −111.4 (d, J$_{F-H}$=12.1 Hz); HRMS Calcd for C$_{24}$H$_{19}$FN$_3$O$_4$ 432.1360, found 432.1355; Anal. racemic compound (a compound of formula (XXII) wherein B=3-aminopyrrolidin-1-yl): (C$_{24}$H$_{18}$FN$_3$O$_4$.HCl.H$_2$O) C, H, N. R-compound (a compound of formula (XXII) wherein B=(R)-3-aminopyrrolidin-1-yl): (C$_{24}$H$_{18}$FN$_3$O$_4$.HCl.4/3H$_2$O) C, H, N. S-compound (a compound of formula (XXII) wherein B=(S)-3-aminopyrrolidin-1-yl): (C$_{24}$H$_{18}$FN$_3$O$_4$.HCl.4/3H$_2$O) C, H, N.

1-(3-Aminopyrrolidin-1-yl)-2-fluoro-4-oxo-4H-pyrido[3,2,1-k,l]-benzo[g]-phenoxazine-5-carboxylic Acid Acid (a Compound of Formula (XXIII, FIG. 4C) wherein B=3-Aminopyrrolidin-1-yl)

The titled compound was synthesized in a similar way as the compound of formula (XXI) (wherein A=3-aminopyrrolidin-1-yl) as a yellow amorphous solid. m.p.>220° C. (decompose), $^1$H NMR (CF$_3$COOD) δ 2.67 (b m, 2H), 4.17 (b m, 1H), 4.48–4.60 (b m, 4H), 7.60–7.67 (m, 2H), 7.76 (s, 1H), 7.84 (m, 1H), 7.92–7.96 (m, 2H), 8.40 (s, 1H), 9.78 (s, 1H); $^{13}$C NMR (DMSO-d$_6$) δ 29.4, 49.1, 49.2, 54.5, 104.4 (d, J$_{C-F}$=24.6 Hz), 108.0, 113.3, 114.9, 116.2 (d, J$_{C-F}$=9.0 Hz), 123.1, 125.4, 126.3 (d, J$_{C-F}$=15.1 Hz), 127.7, 128.3, 129.0 (d, J$_{C-F}$=14.2 Hz), 130.3, 132.3, 133.6 (d, J$_{C-F}$=8.7 Hz), 138.6, 141.8, 153.0 (d, J$_{C-F}$=248 Hz), 165.4, 175.9, 180.2; $^{19}$F NMR (DMSO-d$_6$) δ −119.2 (d, J$_{F-H}$=14.0 Hz); HRMS Calcd for C$_{24}$H$_{19}$FN$_3$O$_4$ 432.1360, found 432.1358; Anal. racemic compound (a compound of formula (XXIII) wherein B=3-aminopyrrolidin-1-yl): (C$_{24}$H$_{18}$FN$_3$O$_4$.HCl.3/2H$_2$O) C, H, N. R-compound (a compound of formula (XXIII) wherein B=(R)-3-aminopyrrolidin-1-yl): (C$_{24}$H$_{18}$FN$_3$O$_4$.HCl.1/2H$_2$O) C, H, N. S-compound (a compound of formula (XXIII) wherein B=(S)-3-aminopyrrolidin-1-yl): (C$_{24}$H$_{18}$FN$_3$O$_4$.HCl.1/2H$_2$O) C, H, N.

1-(Piperazin-1-yl)-2-fluoro-4-oxo-4H-pyrido[3,2,1-k,l]-benzo[h]phenoxazine-5-carboxylic Acid Acid (a Compound of Formula (XXI, FIG. 4C) wherein B=piperazin-1-yl)

Ethyl-1,2-difluoro-4-oxo-4H-pyrido[3,2,1-k,l]-benzo[h] phenoxazine-5-carboxylate (8) (77 mg, 0.2 mmol) was treated with tert-butyl 1-piperazine carboxylate (0.109 g, 0.6 mmol) in pyridine at 110° C. for 60 h. After removing the solvent, the residue was subjected to flash column chromatography to yield a yellow solid. The solid was refluxed in a 4 ml 1:3 mixture of 1N KOH and ethanol for 30 min. The solution was then mixed with equal volume of 1:1 2N HCl and ethanol and refluxed again for 2 h. After cooling down slowly, a yellow amorphous solid was obtained by filtration, extensively washing with water and ethanol, and dried under vacuum (55.6 mg) Yield=60%. m.p.>230° C. (decompose), $^1$H NMR (CF$_3$COOD) δ 3.73 (s, 4H), 3.97 (s, 4H), 7.44 (d, J=9.0 Hz, 1H), 7.68 (t, J=7.2 Hz, 1H), 7.80 (t, J=7.2 Hz, 1H), 7.96 (d, J$_{F-H}$=10.8 Hz, 1H), 8.05 (d, J=7.5HZ, 1H), 8.11 (d, J=8.7 Hz, 1H), 8.28 (d, J=8.7 Hz, 1H), 10.06 (s, 1H); HRMS Calcd for C$_{24}$H$_{19}$FN$_3$O$_4$ 432.1360, found 432.1366.

1-(Piperazin-1-yl)-2-fluoro-4-oxo-4H-pyrido[3,2,1-k,l]-benzo[f]phenoxazine-5-carboxylic Acid (a Compound of Formula (XXII, FIG. 4C) wherein B=piperazin-1-yl)

The titled compound was synthesized in a similar way as the compound of formula (XXI) (wherein A=piperazin-1-yl) as a yellow amorphous solid. Yield=42%. m.p.>210° C. (decompose), $^1$H NMR (CF$_3$COOD) δ 3.81 (s, 4H), 4.07 (s, 4H), 7.80 (b m, 3H), 7.97 (b m, 3H), 8.30 (b, 1H), 9.65 (s, 1H); HRMS Calcd for C$_{24}$H$_{19}$FN$_3$O$_4$ 432.1360, found 432.1351.

1-(Piperazin-1-yl)-2-fluoro-4-oxo-4H-pyrido[3,2,1-k,l]-benzo[g]phenoxazine-5-carboxylic Acid (a Compound of Formula (XXIII, FIG. 4C) wherein B=piperazin-1-yl)

The titled compound was synthesized in a similar way as the compound of formula (XXI) (wherein A=piperazin-1-yl) as a yellow amorphous solid. Yield=37%. m.p.>200° C. (decompose), $^1$H NMR (CF$_3$COOD) δ 3.79 (s, 4H), 4.03 (s, 4H), 7.60–7.72 (m, 2H), 7.81 (s, 1H), 7.89 (d, J=8.7 Hz, 1H), 7.97–8.02 (m, 2H), 8.53 (s, 1H), 9.93 (s, 1H); HRMS Calcd for C$_{24}$H$_{19}$FN$_3$O$_4$ 432.1360, found 432.1348.

5.16 Example 3 (FIG. 4D)

Ethyl 3-(6-Hydroxydibenzofuran-3-amino)-2-((2,3, 4,5-tetrafluorophenyl)carbonyl) prop-2-enoate (Compound 12 of FIG. 4D)

The titled compound was prepared in the same manner as compound 5 of FIG. 4C by using 3-amino-6-hydroxydibenzofuran hydrogen bromide (4.07 g, 14.6 mmol) in place of 1-aminonaphthalen-2-ol hydrogen chloride. Yield: 83%. MS (Cl): m/z 474 (M+H); $^1$H NMR (CDCl$_3$) δ (mixture of isomers) 1.17–1.26 (m, 3H), 2.95 (br s, 1H), 4.10–4.25 m2, 7.05–7.20 (m, 1H), 7.33 m2, 7.43 (m, 1H), 7.52 (m, 3H), 7.85 (m, 1H), 8.69 (s, 0.7H), 8.74 (s, 0.3H); $^{19}$F NMR δ −156.2 (m, 1F), −154.5 (m, 0.75F), −135.4 (m, 0.25F), −140.3 (m, 0.75F), −139.4 (m, 1F), 139.3 (m, 0.25F).

Ethyl 1,2-Difluoro-4-oxo-4H-pyrido[3,2,1-k,l]-(3-amino-6-hydroxydibenzofuranyl)[1,2-g] phenoxazine-5-carboxylate (Compound 13 of FIG. 4D)

The titled compound was prepared in the same manner as compound 8 of FIG. 4C by using compound 12 of FIG. 5D (2.32 g, 4.9 mmol) in place of compound 5. Yield: 89%. MS (CI): m/z 434 (M+H); $^1$H NMR (CDCl$_3$) δ 1.49 (t, J=7.2 Hz, 3H), 4.48 (q, J=7.2 Hz, 2H), 7.39 (t, J=3.6 Hz, 1H), 7.50–7.631, 7.80 (dd, J=7.8, 2.1 Hz, 1H), 7.90 (d, J=7.8 Hz, 1H), 9.01 (s, 1H); $^{19}$F NMR δ −1561.5 (dd, J=21, 9 Hz, 1F), −133.6 (dd, J=23, 10Hz, 1F).

Ethyl (S)-1-(3-((tert-Butoxy)carbonylamino) pyrrolidin-1-yl)-2-fluoro-4-oxo-4H-pyrido[3,2,1-k, l]-(3-amino-6-hydroxydibenzofuranyl)[1,2-g] phenoxazine-5-carboxylate (Compound XXIV of FIG. 4D)

The titled compound was prepared in the same manner as compound XVIII of FIG. 4C by using compound 13 of FIG. 4D (0.232 g, 0.54 mmol) in place of compound 8. Yield: 84%. MS (CI): m/z 600 (M+H); $^1$H NMR (CDCl$_3$) δ 1.46 (t, J=7.2 Hz, 3H), 1.49 (s, 9H), 2.00 (m, 1H), 2.29 (m, 1H), 3.61 (m, 1H), 3.70 (m, 1H), 3.40 (m, 2H), 4.42 (m, 1H), 4.44 (q, J=7.2 Hz, 2H), 5.35 (br s, 1H), 7.39 (t, J=6.9 Hz, 1H), 7.51 (t, J=6.9 Hz, 1H), 7.57 (s, 1H), 7.64 (m, 3H), 7.90 (d, J=7.5 Hz, 1H), 8.90 (s, 1H); $^{19}$F HMR δ −119.8 (d, J=13 Hz, 1F).

(S)-1-(3-Aminopyrrolidin-1-yl)-2-fluoro-4-oxo-4H-pyrido[3,2,1-k,l]-(3-amino-6-hydroxydibenzofuranyl)[1,2-g]phenoxazine-5-carboxylic Acid HCl Salt (Compound XXV of FIG. 4D)

The titled compound was prepared in the same manner as compound XXI of FIG. 4C by using compound XXIV of FIG. 4D (0.228 g, 0.526 mmol) in place of compound 8. Yield: 95%. MS (CI): m/z 472 (M+H); $^1$H NMR (DMSO-d$_6$) δ 2.08 (m, 1H), 2.31 (m, 1H), 3.80–4.05 (m, 5H), 7.40 (t, J=7.5 Hz, 1H), 7.47 (t, J=13.5 Hz, 1H), 7.54 (t, J=7.2 Hz, 1H), 7.69 (d, J=8.4 Hz, 1H), 8.05 (d, J=7.5 Hz, 1H), 8.12 (s, 1H), 8.49 (m, 1H), 9.24 (s, 1H); $^{19}$F NMR δ −119.1 (d, J=15 Hz, 1F).

Ethyl (R)-1-(3-((tert-Butoxy)carbonylamino) pyrrolidin-1-yl)-2-fluoro-4-oxo-4H-pyrido[3,2,1-k, l]-(3-amino-6-hydroxydibenzofuranyl)[1,2-g] phenoxazine-5-carboxylate (Compound XXIV of FIG. 4D)

The titled compound was prepared in the same manner as compound XVIII of FIG. 4C by using compound 13 of FIG. 4D (0.232 g, 0.54 mmol) in place of compound 8. Yield: 90%. MS (CI): m/z 600 (M+H); $^1$H NMR (CDCl$_3$) (same as XXIV).

(R)-1-(3-Aminopyrrolidin-1-yl)-2-fluoro4-oxo-4H-pyrido[3,2,1-k,l]-(3-amino-6-hydroxydibenzofuranyl)[1,2-g]phenoxazine-5-carboxylic Acid HCl Salt (Compound XXIV of FIG. 4D)

The titled compound was prepared in the same manner as compound XXI of FIG. 4C by using compound XXIV of FIG. 4D (0.228 g, 0.526 mmol) in place of compound 8. Yield: 85%. MS (CI): m/z 585 (M+H); $^1$H NMR (DMSO-d$_6$) (same as XXV).

5.17 Example 4 (FIG. 4E)

Synthesis of DNA Alkylating Quinobenzoxazine tert-Butyl 2,3,4,5-Tetrafluorobenzoylacetate (Compound 15 of FIG. 4E)

A solution of 2,3,4,5-tetrafluorobenzoyl chloride (21.25 g, 100 mmol), 2,2-dimethyl-1,3-dioxane-4,6-dione (14.41 g, 100 mmol), and 4-dimethylaminopyridine (30.50 g, 250 mmol) in dichloromethane was stirred at room temperature for 1 h. The reaction mixture was evaporated to dryness, dissolved with ether, and washed with 1N HCl and brine. The organic layer was dried with MgSO$_4$, filtered, and evaporated to give 29.9 g of a pale yellow solid (compound 14 of FIG. 4E). Yield: 90%. MS (CI): m/z 321 (M+H); $^1$H NMR (CDCl$_3$) δ 1.83 (s, 6H), 7.25 (s, 1H); $^{19}$F NMR δ −153.5 (m, 1F), −147.5 (m, 1F), −137.0 (m, 1F), −134.3 (m, 1F). The resulting solid was used for the next step without further purification. A solution of this compound (19.0 g, 59.35 mmol) (14 of FIG. 4E) in tert-butanol was refluxed for 1 h. After the solvent was removed in vacuo, the resulting solid was purified by flash column chromatography on silica gel (ethyl acetate:hexanes=1:10) to give 13.8 g of tert-butyl 2,3,4,5-tetrafluorobenzoylacetate as a white solid (compound 15 of FIG. 4E). Yield: 80%. MS (CI): m/z 293 (M+H); $^1$H NMR (CDCl$_3$) δ (two sets of signals) 1.45 (s, 0.9H), 1.54 (s, 8.1H), 3.88 (d, J=3.9 Hz, 0.2H), 5.74 (s, 0.9H), 7.50 (m, 0.9H), 7.61 (m, O.1H); $^{19}$F NMR δ (two sets of signals) −154.6 (m, 0.9F), −153.3 (m, 0.1F), −151.3 (m, 0.9F), −145.9 (m, 0.1F), −138.2 (m, 0.9F), −137.1 (m, 1F), −136.5 (m, 0.1F), −135.6 ({, 0.1F).

tert-Butyl 3-(2'-Hydroxyl-4'-(N-(2-trimethylsilylethoxycarbonyl)aminomethyl)anilino)-2-(2,3,4,5-tetrafluorobenzoyl)acrylate (Compound 17 of FIG. 4E)

The titled compound was prepared in the same manner as compound 5 of FIG. 4C by using tert-butyl 2,3,4,5-tetrafluorobenzoylacetate (2.433 g, 8.328 mmol) and 2'-hydroxyl-4'-((N-(2-trimethylsilyl)ethoxycarbonyl) aminomethyl)aniline (2.352 g, 8.328 mmol) in place of ethyl 2,3,4,5-tetrafluorobenzoylacetate and 1-aminonaphthalen-2-ol hydrogen chloride, respectively. Yield: 86%. MS (CI): m/z 585 (M+H); $^1$H NMR (CDCl$_3$) δ (two sets of signals) 0.32 (s, 9H), 1.01 (m, 2H), 1.29 (s, 2.7H), 1.34 (s, 6.3H), 4.22 (m, 2H), 4.30 (m, 2H), 5.11 (br s, 1H), 6.85 (m, 1H), 7.30 (m, 1H), 7.15 (m, 1H), 7.27 (m, 1H), 8.35 (br s, 1H), 8.53 (d, J=14.4 Hz, 0.3H), 8.62 (d, J=14.1 Hz, 0.7H); $^{19}$F NMR δ (two sets of signals) −156.5 (m, 0.3F), −153.2 (m, 0.7F), −153.9 (m, 0.7F), −153.6 (m, 0.3F), −139.7 (m, 0.7F), −139.3 (m, 0.3F), −138.9 (m, 1F).

tert-Butyl 1,2-Difluoro-9-(N-(2-trimethylsilylethoxycarbonyl)aminomethyl)-4-oxo-4H-quino[2,3,4-i,j][1,4]benzoxazine-5-carboxylate (Compound 18 of FIG. 4E)

A solution of tert-butyl 3-(2'-hydroxyl-4'-((N-(2-trimethylsilyl)ethoxycarbonyl)aminomethyl)anilino)-2-(2,3,4,5-tetrafluorobenzoyl)acrylate (compound 17 of FIG. 4E) (3.54 g, 6.06 mmol) and sodium bicarbonate (2.55 g, 30.30 mmol) in DMF was stirred at 100° C. for 3 hr under a nitrogen atmosphere and allowed to cool to room temperature. The solution was removed in vacuo. The residue was crystallized from ethyl acetate:hexanes (4:1) to give 2.67 g of tert-butyl 1,2-difluoro-9-((N-(2-trimethylsilyl) ethoxycarbonyl)aminomethyl)-4-oxo-4H-quino[2,3,4-i,j][1,4]benzoxazine-5-carboxylate (compound 18 of FIG. 4E). Yield: 80%. MS (CI): m/z 545 (M+H); $^1$H NMR (CDCl$_3$) δ 0.05 (s, 9H), 1.02 (m, 2H), 1.64 (s, 9H), 4.22 (m, 2H), 4.36 (d, J=6.3 Hz, 2H), 5.13 (br s, 1H), 7.12 (m, 2H), 7.39 (d, J=9.3 Hz, 1H), 7.77 (dd, J=7.8 and 10.2 Hz, 1H), 8.88 (s, 1H); $^{19}$F NMR δ −151.6 (m, 1F), −133.8 (m, 1F).

tert-Butyl 1-(3-tert-Butoxycarbonylaminopyrrolidin-1-yl)-2-fluoro-9-((N-(2-trimethylsilyl) ethoxycarbonyl)aminomethyl)-4-oxo-4H-quino[2,3, 4-i,j][1,4]benzoxazine-5-carboxylate (Compound 19 of FIG. 4E)

The titled compound was prepared in the same manner as the compound of formula (XVIII) (wherein A=3-((tert-butoxy)carbonylamino)pyrrolidin-1-yl) of FIG. 4C by using tert-butyl 1,2-difluoro-9-((N-(2-trimethylsilyl) ethoxycarbonyl)aminomethyl)-4-oxo-4H-quino[2,3,4-i,j][1, 4]benzoxazine-5-carboxylate (compound 18 of FIG. 4E) (1 g, 1.836 mmol) in place of compound 8 of FIG. 4C. Yield: 80%. MS (CI): m/z 711 (M+H); $^1$H NMR (CDCl$_3$) δ 0.06 (s, 9H), 1.03 (m, 2H), 1.47 (s, 9H), 1.64 (s, 9H), 1.96 (m, 1H), 2.24 (m, 1H), 3.47 (m, 1H), 3.62 (m, 1H), 3.84 (m, 1H), 3.93 (m, 1H), 4.22 (m, 2H), 4.33 (m, 3H), 5.04 (br s, 1H), 5.39 (br s, 1H), 6.90 (s, 1H), 6.99 (d, J=8.4 Hz, 1H), 7.24 (m, 1H), 7.56 (d, J=13.8 Hz, 1H), 8.68 (s, 1H); $^{19}$F NMR δ −120.0 (m, 1F).

tert-Butyl 1-(3-tert-Butoxycarbonylaminopyrrolidin-1-yl)-2-fluoro-9-(aminomethyl)-4-oxo-4H-quino[2,3, 4-i,j][1,4]benzoxazine-5-carboxylate (Compound 20 of FIG. 4E)

To a solution of tert-butyl 1-(3-tert-butoxycarbonylaminopyrrolidin-1-yl)-2-fluoro-9-((N-(2-trimethylsilyl)ethoxycarbonyl)aminomethyl)-4-oxo-4H-quino[2,3,4-i,j][1,4]benzoxazine-5-carboxylate (compound 19 of FIG. 4E) (400 mg, 0.563 mmol) in DMF was added 1M tetrabutylammonium fluoride (0.844 ml, 0.844 mmol) in THF under a nitrogen atmosphere. The reaction mixture was stirred for 3 hr at room temperature. The solution was removed under vacuum. The residue was purified by flash column chromatography on silica gel (ammonia water:methanol:chloroform=1:7:92) to give 287 mg of tert-butyl 1-(3-tert-butoxycarbonylaminopyrrolidin-1-yl)-2-fluoro-9-(aminomethyl)-4-oxo-4H-quino[2,3,4-i,j][1,4]benzoxazine-5-carboxylate (compound 20 of FIG. 4E). Yield: 90%. MS (CI): m/z 567 (M+H); $^1$H NMR (CDCl$_3$) δ 1.47 (s, 9H), 1.63 (s, 9H), 1.92 (m, 1H), 2.22 (m, 1H), 3.48 (m, 1H), 3.62 (m, 1H), 3.84 (m, 1H), 3.89 (s, 1H), 3.90 (m, 1H), 4.32 (br s, 1H), 4.94 (br s, 1H), 7.09 (m, 2H), 7.32 (d, J=8.4 Hz, 1H), 7.59 (d, J=13.8 Hz, 1H), 8.76 (s, 1H); $^{19}$F NMR δ −120.2 (m, 1F).

tert-Butyl 1-(3-tert-Butoxycarbonylaminopyrrolidin-1-yl)-2-fluoro-9-(N-(bromoacetyl)aminomethyl)-4-oxo-4H-quino[2,3,4-i,j][1,4]benzoxazine-5-carboxylate (Compound 8 of FIG. 4C)

A suspension of tert-butyl 1-(3-tert-butoxycarbonylaminopyrrolidin-1-yl)-2-fluoro-9-(aminomethyl)-4-oxo-4H-quino[2,3,4-i,j][1,4]benzoxazine-5-carboxylate (compound 20 of FIG. 4E) (34 mg, 0.060 mmol) and bromoacetic anhydride (31 mg, 0.120 mmol) in THF was stirred at room temperature for 1 h. The product was extracted with chloroform. The chloroform layer was evaporated and purified by flash column chromatography on silica gel (methanol:chloroform=2:98) to give 35 mg of tert-butyl 1-(3-tert-butoxycarbonylaminopyrrolidin-1-yl)-2-fluoro-9-(N-(bromoacetyl)aminomethyl)-4-oxo-4H-quino[2,3,4-i,j][1,4]benzoxazine-5-carboxylate (compound 21 of FIG. 4E). (5) Yield: 85%. MS (CI): m/z 689, 687 (M+H); $^1$H NMR (CDCl$_3$) δ 1.46 (s, 9H), 1.64 (s, 9H), 1.90 (m, 1H), 2.19 (m, 1H), 3.46 (m, 1H), 3.59 (m, 1H), 3.79 (m, 1H), 3.89 (m, 1H), 4.09 (s, 2H), 4.31 (m, 1H), 4.35 (dd, J=6.0 and 15.0 Hz, 1H), 4.85 (dd, J=6.0 and 15.0 Hz, 1H), 5.17 (br s, 1H), 6.73 (s, 1H), 6.88 (d, J=8.4 Hz, 1H), 7.07 (d, J=8.4 Hz, 1H), 7.50 (d, J=14.1 Hz, 1H), 7.71 (br s, 1H), 8.52 (s, 1H); $^{19}$F NMR δ −119.0 (d, J$_{F-H}$=12.1 Hz, 1F).

1-(3-tert-Aminopyrrolidin-1-yl)-2-fluoro-9-(N-(bromoacetyl)aminomethyl)-4-oxo-4H-quino[2,3,4-i,j][1,4]benzoxazine-5-carboxylic Acid TFA Salt (Compound 22 of FIG. 4E)

A solution of tert-butyl 1-(3-tert-butoxycarbonylaminopyrrolidin-1-yl)-2-fluoro-9-(N-(bromoacetyl)aminomethyl)-4-oxo-4H-quino[2,3,4-i,j][1,4]benzoxazine-5-carboxylate (compound 21 of FIG. 4E) (54 mg, 0.0785 mmol) and trifluoroacetic acid (TFA) (2 ml) in dichloromethane (2 ml) was stirred at room temperature for 16 h. After the solvent was removed in vacuo, the residue was triturated with ethanol and ethyl acetate. The resulting reddish brown solid was collected on filter paper by suction filtration. The filter cake was dried under vacuum at room temperature for 16 hr to give 37 mg of 1-(3-tert-Aminopyrrolidin-1-yl)-2-fluoro-9-(N-(bromoacetyl)aminomethyl)-4-oxo-4H-quino[2,3,4-i,j][1,4]benzoxazine-5-carboxylic acid TFA salt (compound 22 of FIG. 4E). Yield: 73%. $^1$H NMR (DMSO-d$_6$) δ 2.00 (m, 1H), 2.27 (m, 1H), 3.86 (m, 1H), 3.93 (m, 3H), 3.94 (s, 2H), 4.30 (br s, 1H), 7.15 (br s, 2H), 7.54 (d, J=13.5 Hz, 1H), 8.02 (d, J=9.0 Hz, 1H), 8.09 (br s, 3H), 8.92 (br s, 1H), 9.13 (s, 1H); $^{19}$F NMR δ −119.2 (d, J$_{F-H}$=11.9 Hz, 1F), −74.6 (s, 3F); HRMS calcd for C$_{23}$H$_{20}$N$_4$O$_5$BrF 530.0611, found 530.0602.

5.19 Competition Between Psorospermin and A-62176

Psorospermin, a potent DNA alkylating antitumor agent, has been shown to intercalate into the DNA helix and alkylate N-7 of guanine at the 3' side of the intercalation site (Hansen et al., 1996). In the presence of topo II, the reactivity of psorospermin is enhanced more than 40-fold with the guanine at the +4' position at site B in FIG. 7 (Kwok et al., 1998a and 1998b). A DNA strand breakage assay was used to locate the position of alkylation of DNA by the epoxide of psorospermin upon intercalation to the base pairs between the +1 and +2 positions at site B within the topo II-DNA complex (Kwok et al., 1998a). Psorospermin has subsequently been used to probe the binding sites for m-AMSA (Kwok et al., 1998a). In the present study, this same assay was performed to determine the binding site of A-62176 on DNA in the presence of topo II.

The A-62176 photocleavage studies have demonstrated that topo II produces a structural distortion at the +1 and +2 positions at site B that creates a binding pocket for A-62176. As an independent method for determining the specific location of A-62176, a competition study between psorospermin and A-62176 was carried out (FIG. 8). As demonstrated previously, psorospermin displayed relatively weak DNA reactivity at a 10 mM concentration in the absence of topo II (FIG. 8A, lane 5); however, in the presence of topo II, the psorospermin alkylation of the guanine at the +4' position of site B (band 2) was greatly enhanced (lane 6), while the reactivity of psorospermin with the guanines at other positions (such as bands 1 and 3) remained unchanged (Kwok et al., 1998). As the concentrations of A-62176 were increased (lanes 7–11), the amount of psorospermin alkylation at site B decreased (band 2), as shown by the reduction of the strand breakage product, while the reactivity of psorospermin with the guanines at other position (bands 1 and 3) showed little if any change (FIG. 8B). Since A-62176 is a DNA-interactive intercalator, this competition effect may be due to its nonspecific inhibition of topo II binding to DNA at site B. However, in this study nonhydrolyzable ATP was used. Under these conditions, a concentration of A-62176 (up to 10 μM) can enhance the topo II-mediated cleavage (FIG. 5). Therefore, these results indicate that A-62176 can specifically compete with psorospermin for intercalation between positions +1 and +2 in the presence of topo II. For comparison, Norfloxacin was used instead of A-62176 in a parallel study. In contrast to the intercalating A-62176, the nonintercalating Norfloxacin showed no competition with psorospermin (lanes 12–16). In fact, quantitative data showed that Norfloxacin produced a small but significant enhancement of the psorospermin alkylation at site B (FIG. 8B). Overall, these results strongly support the idea that A-62176 specifically interacts with DNA at the site where psorospermin binds in the presence of topo II (i. e. between positions +1 and +2).

5.16 The Cooperative Binding of A-62176 and Norfloxacin in the Presence of Topo II as Evidence for the Assembly of a 2:2 Drug:Mg$^{2+}$ Complex on the Topo II-DNA Complex In a previous study, it was proposed that a 2:2 drug:Mg$^{2+}$ complex forms a "heterodimer complex" with respect to DNA, in which one A-62176 molecule is intercalated into DNA and a second A-62176 molecule is externally bound, held to the first molecule by two Mg$^{2+}$ bridges (Fan el al., 1995). In this complex, on the basis of DNase I and viscometry studies, externally bound A-62176 molecules can be replaced by Norfloxacin, demonstrating that Norfloxacin and A-62176 bind to DNA in a cooperative manner. In the present study, competition studies between psorospermin and A-62176, in combination with Norfloxacin, were used to determine if the heterodimer complex is also formed in the presence of topo II. The psorospermin alkylation of guanine at the +4' position of site B (lane 5 of FIG. 9A) is greatly enhanced in the presence of topo II (compared to lane 4). As the concentrations of A-62176 were increased (lanes 6–11), the amount of alkylation by psorospermin at the same positions decreased. The effects of 20 and 100 mM of Norfloxacin in combination with A-62176 on psorospermin alkylation are shown in lanes 12–18 and 19–25, respectively. At face value, it appears that Norfloxacin has no effect on psorospermin alkylation in combination with A-62176 (FIG. 9B, Graph II); however, when the enhancement effect of Norfloxacin alone on psorospermin alkylation (lanes 12 and 19 in FIG. 9A; FIG. 9B, Graph I) is taken into account, it is evident that Norfloxacin does show an additive effect with A-62176. If the enhancement effect by Norfloxacin alone on psorospermin alkylation is subtracted from the combination effect, as shown in FIG. 9B, Graph III, A-62176, in combination with 20 mM of Norfloxacin, shows an additive effect on the inhibition of psorospermin alkylation. This additive effect is even more dramatic when 100 mM of Norfloxacin is used. Hence, A-62176 and Norfloxacin bind to the topo II-DNA complex in a cooperative manner, which is consistent with the 2:2 drug:$Mg^{2+}$ model originally proposed for the binary complex between the quinobenzoxazines and DNA (Fan et al., 1995).

5.17 The Experimental Findings are Consistent with a 2:2 Quinobenzoxazine:$Mg^{2+}$ Heterodimer Complex, Which Can Assemble in the Presence of Topo II The results of previous studies have led to a proposal of a 2:2 quinobenzoxazine:$Mg^{2+}$ heterodimer complex model on duplex DNA, in which one quinobenzoxazine molecule serves as an intercalator and the other quinobenzoxazine molecule binds externally, held to the first drug molecule by two $Mg^{2+}$ ions (FIG. 10A) (Fan et al., 1995). Since Norfloxacin and A-62176 can cooperatively interact with DNA in the presence of $Mg^{2+}$, and together they can further lengthen the DNA helix, it was suggested that the externally bound A-62176 molecule could be replaced by the nonintercalating Norfloxacin (Fan et al., 1995), thereby forming a 1:1:2 A-62176:Norfloxacin:$Mg^{2+}$ heterodimer (FIG. 10B). However, this model was proposed based on the experimental evidence on the drug-DNA binary complex in the absence of topo II. The inventors' results (FIG. 9) show that A-62176 and Norfloxacin have cooperative effects in the competition with psorospermin in the presence of topo II, indicating that this heterodimer complex may also assemble in the topo II-DNA complex (FIG. 10, A and B). Surprisingly, in the presence of topo II, the externally bound Norfloxacin itself can facilitate the alkylation of psorospermin, although Norfloxacin is not able to produce the same effect in the absence of topo II. It is not known whether this cooperative effect results from the complex formation between psorospermin and Norfloxacin at the topo II cleavage gate or by the direct interaction between Norfloxacin and topo II, although Norfloxacin, a gyrase (bacterial topo II) poison, has not been shown to be a eukaryotic topo II inhibitor.

5.18 Implications for Drug Design

The 2:2 quinobenzoxazine:$Mg^{2+}$ and 1:1:2 quinobenzoxazine:Norfloxacin:$Mg^{2+}$ heterodimer models have important implications for future drug design, not only for eukaryotic topo II but also for gyrase, since Norfloxacin is known to be a gyrase inhibitor. The proposed drug:$Mg^{2+}$ heterodimers have two moieties: one of them interacts exclusively with DNA through intercalation and the other binds externally to DNA (FIG. 9A and FIG. 9B). The results presented here suggest that topo II induces transient structural distortion, possibly unwinding, that is captured or stabilized by the binding of A-62176 at the topo II cleavage gate. Therefore, the binding of the A-62176:$Mg^{2+}$ heterodimer to the topo II-DNA complex includes not only the intercalation of one A-62176 molecule to the partially unwound DNA base pairs at the gate, but also the interaction of the externally bound A-62176 molecule to topo II. This model provides substantial information for drug design. One of the inventors current approaches is to extend the polyaromatic ring system that intercalates into the base pairs. A series of new quinobenzoxazine analogues have been synthesized, and studies show that they are more potent against several cancer cell lines than the parent compound A-62176 (Zeng et al., 1998). Further studies are underway to fine-tune the two quinobenzoxazine molecules in their interaction with $Mg^{2+}$, DNA, and topo II.

In summary, the inventors have shown that quinobenzoxazine A-62176 can be both a topo II poison (at site B) and a catalytic inhibitor (at site A) at pH 6–7. It is suggested that topo II induces a conformational change or a distortion at positions +1 and +2 at site B, which creates a binding pocket for A-62176. The inventors' results are consistent with the proposed 2:2 quinobenzoxazine:$Mg^{2+}$ heterodimer, which may assemble in the presence of topo II, in which the intercalation molecule of the heterodimer interacts with the base pairs within the topo II cleavage gate, while the externally bound molecule might interact with topo II. Last, the inventors propose, by analogy with the 2:2 quinobenzoxazine:$Mg^{2+}$ complex, that a 2:2 quinolone:$Mg^{2+}$ complex can form on bacterial gyrase.

Cooperative effect of Norfloxacin with the DNA intercalating quinolone QQ58 (III in FIG. 2) on its in vitro cytotoxic potency.

On the basis of the 2:2 quinobenzoxazine:$Mg^{2+}$ model and the derivative quinobenzoxazine:Norfloxacin:$Mg^{2+}$ 1:1:2 heterodimer model (see before), the inventors predict that addition of the nonintercalating Norfloxacin to an intercalating topoisomerase II-interactive compound such as III should increase its cytotoxic potency.

In separate studies, the $IC_{50}$ of III and the $IC_{10}$, $IC_{20}$, and $IC_{50}$ of Norfloxacin were determined for DU-145, a prostate cell line. As expected, Norfloxacin was at least 1000-fold less potent than III, since it does not stabilize the topo II-DNA complex. However, in combination with III, Norfloxacin at 34 and 5 lower concentrations than required to produce its $IC_{50}$ values produced a significant increase (13× and 20×, respectively) in the cytotoxic potency of III (FIG. 11).

Compound 2b (FIG. 3) binds to G-quadruplex DNA and blocks DNA synthesis in a concentration dependent manner.

Although it has been shown that G-quadruplex structures block primer extension by DNA polymerase in a $K^+$ dependent manner (Wietzmann et al., 1996), the inventors are unaware of any reports showing enhanced blockage by G-quadruplex-interactive agents. To determine if 2b binding to G-quadruplex enhances the block to DNA synthesis, primer extension reactions were carried out in the absence and presence of 2b. FIG. 12A shows the results of Taq DNA polymerase primer extension on DNA templates containing four repeats of TTGGGG in the presence of different concentrations of 2b at 55° C. These results are presented in graph form in FIG. 11B. In these studies, $K^+$ was added at low concentrations in order to prevent overwhelming polymerase pausing due to formation of highly stable G-quadruplex structures. In the absence of 2b, there is only a slight pausing of the Taq DNA polymerase when it reaches the 3'-end of the G-rich site on the template DNA at 55° C. (CN in FIG. 12A). However, upon increasing the concentration of 2b, enhanced pausing is observed at the same site as that seen with low K+ concentrations. This suggests that 2b enhances the polymerase pausing by stabilizing the G-quadruplex structure formed in the K+ buffer. At high 2b concentrations, the inventors observed not only enhanced pausing at the 3'-end of the G-quadruplex site but also increased premature termination resulting from nonspecific interactions between 2b and the single-stranded template DNA. At a 2b concentration of 100 μM, the primer extension is completely inhibited due presumably to nonspecific interactions between 2b and the single- and/or double-stranded DNA or between 2b and the polymerase itself.

All of the compositions and methods of synthesis disclosed and claimed herein can be made and executed without undue experimentation in light of the present disclosure. While the compositions and methods of this invention have been described in terms of preferred embodiments, it will be apparent to those of skill in the art that variations may be applied to the compositions and methods of synthesis and in the steps or in the sequence of steps of the method described herein without departing from the concept, spirit, and scope of the invention. More specifically, it will be apparent that certain agents that are both chemically and physiologically related may be substituted for the agents described herein, while the same or similar results would be achieved. All such similar substitutes and modifications apparent to those skilled in the art are deemed to be within the spirit, scope, and concept of the invention as defined by the appended claims.

7.0 REFERENCES

The following references, to the extent that they provide exemplary procedural or other details supplementary to those set forth herein, are specifically incorporated herein by reference.

Chen, Behrens, Behrens, Czerniak, Dexter, Dusak, Fredericks, Gale, Gross, Jiang, Kirshenbaum, McRipley, Papp, Patten, Perrella, Seitz, Stafford, Sun, Sun, Von Hoff, *Anticancer Drugs*, 4:447–457, 1993.
Chu and Maleczka Jr., *J. Heterocyclic Chem.*, 24:453–456, 1987.
Chu, Hallas, Clement, Alder, Mcdonald, Plattner, *Drugs Exptl. Clin. Res.*, 18:275–282, 1992.
Chu, Hallas, Tanaka, Alder, Balli, Plattner, *Drugs Exptl. Clin. Res.*, 20:177–183, 1994.
Clement, Burres, Jarvis, Chu, Swiniarski, Alder, *Cancer Res.*, 55:830–835, 1995.
Fan, Sun, Yu, Kerwin, Hurley, *J. Med. Chem.*, 38:408–424, 1995.
Fedoroff, Salazar, Han, Chemeris, Kerwin, Hurley, *Biochemistry*, 37:12367–12374, 1998.
Hansen, Lee, Cassady, Hurley, *J. Am. Chem. Soc.*, 118:5553–5561, 1996.
Henderson, Moore, Malcolm, *Biochemistry*, 29:732–737, 1990.
Kwok, Zeng, Hurley, *Proc. Natl. Acad. Sci. USA.*, 95:13531–13536, 1998a.
Kwok and Hurley, *J. Biol. Chem.*, 49:33020–33026, 1998.
Liu, *Annu. Rev. Biochem.*, 58:351–375, 1989.
MacDonald, DeWitt, Hogan, Ramage, *Tetrahedron Lett.*, 37:4815–4818, 1996.
Maxam and Gilbert, *Methods Enzymol.*, 65:499–560, 1980.
Mergny and Héléne, *Nature Medicine*, 4:1366–1367, 1998.
Mitscher, Devasthale, Zavod, *Structure-Activity Relationships of Fluoro-4-Quinolones*, Springer-Verlag: New York, 1990.
Morin, *J. Natl. Cancer Inst.*, 87:859–861, 1995.
Parkinson, *Br. J. Cancer*, 73:1–4, 1996.
Permana, Snapka, Shen, Chu, Clement, Plattner, *Biochemistry*, 33:11333–11339, 1994.
Radl and Zikan, *Collect. Czech. Chem. Commun.*, 54:506–515, 1989.
Raymond, Sun, Chen, Windle, Von Hoff, *Curr. Opinion Biotch.*, 7:583–591, 1996.
Rodi, Holton, Wallace, *J. Mol. Biol.*, 285:197, 1999.
Shen, Baranowski, Pemet, *Biochemistry*, 28:3879–3885, 1989a.
Shen, Kohlbrenner, Weigl, Baranowski, *J. Biol. Chem.*, 264:2973–2978, 1989b.
Shen, Mitscher, Sharma, O'Donnell, Chu, Cooper, Rosen, Pemet, *Biochemistry*, 28:3886–3894, 1989c.
Sun, Thompson, Cathers, Salazar, Kerwin, Trent, Jenkins, Neidle, Hurley, *J. Med. Chem.*, 40:2113–2116, 1997.
Wang and Patel, *Structure*, 1:263–282, 1993.
Weitzmann, Woodword, Usdin, *J. Biol. Chem.*, 271:20958–20964, 1996.
Wheelhouse, Sun, Han, Han, Hurley, *J. Am. Chem. Soc.*, 120:3261–3262, 1998.
Willmott and Maxwell, *Antimicrob. Agents Chemother.*, 37:126–127, 1993.
Yu, Hurley, Kerwin, *J. Am. Chem. Soc.*, 118:7040–7048, 1996.
Zeng, Kwok, Kerwin, Mangold, Hurley, *J. Med. Chem.*, 41:4273–4278, 1998.

What is claimed is:

1. A method for stabilizing a topoisomerase II-DNA complex comprising the step of contacting a cell containing said complex with a DNA intercalating quinobenzoxazine derivative that has a formula:

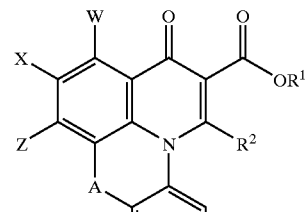

or

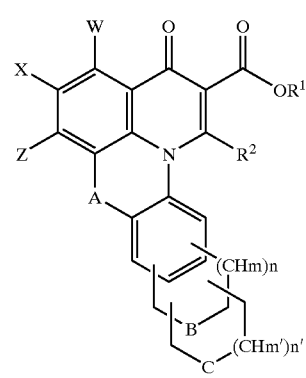

or a pharmaceutically acceptable salt, ester, or amide thereof, in which m=0, 1, 2;

m'=0, 1, 2;

n=0, 1, 2;

n'=0, 1, 2;

$R^1$=hydrogen or carboxy-protecting group;

$R^2$=hydrogen, halogen, or alkyl consisting of 1 to 6 carbon atoms;

$R^3$ or $R^4$=alkyl, acyl, amino acids, short peptides, or DNA alkylating, groove binding, intercalating functionalities, or any ligand for nuclear receptors;

A=oxygen, sulfur, or carbon;

Z=a halogen or nitrogen-containing group consisting of 1 to 6 carbon atoms;

X=hydrogen or halogen;

W=hydrogen, nitro, amino, alkyl amino, halo-substituted alkyl, or halogen;

B=N, O, S, C, CH, $CH_2$;

C=N, O, S, C, CH, $CH_2$;

whereby said quinobenzoxazine derivative binds to and stabilizes said complex.

2. The method of claim 1, wherein said quinobenzoxazine has the formula of:

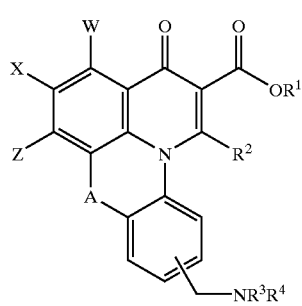

or a pharmaceutically acceptable salt, ester, or amide thereof.

3. The method of claim 1, further comprising contacting said cell with a fluoroquinolone other than said quinobenzoxazine derivative, wherein said fluoroquinolone interacts with topoisomerase II-DNA complex in the presence of said quinobenzoxazine derivative.

4. The method of claim 3, wherein said fluoroquinolone is Norfloxacin.

5. A method for screening a fluoroquinolone for the ability to enhance the antineoplastic or antibiotic activity of an intercalating quinobenzoxazine derivative comprising (a) contacting a candidate fluoroquinolone and an intercalating quinobenzoxazine derivative with a cell and (b) determining the effect of said fluoroquinolone of the cytotoxicity on said quinobenzoxazine derivative, whereby an increase in the cytotoxcity of said quinobenzoxazine derivative in the presence of said fluoroquinolone, a compared to the cytotoxcity of said quinobenzoxazine derivative in the absence of said fluoroquinolone, identifies said fluoroquinolone as an enhancer of quinobenzoxazine cytotoxicity, wherein said quinobenzoxazine derivative has a formula:

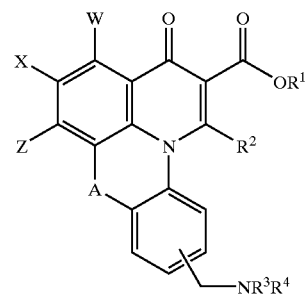

or

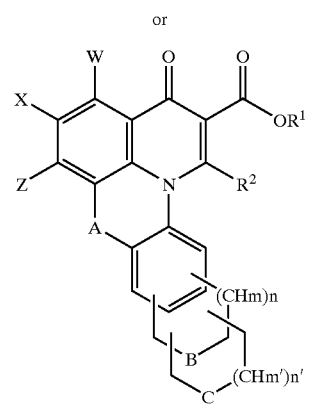

or a pharmaceutically acceptable salt, ester, or amide thereof, in which m=0, 1, 2;

m'=0, 1, 2;

n=0, 1, 2;

n'=0, 1, 2;

$R^1$=hydrogen or carboxy-protecting group;

$R^2$=hydrogen, halogen, or alkyl consisting of 1 to 6 carbon atoms;

$R^3$ or $R^4$=alkyl, acyl, amino acids, short peptides, or DNA alkylating, groove binding, intercalating functionalities, or any ligand for nuclear receptors;

A=oxygen, sulfur, or carbon;

Z=a halogen or nitrogen-containing group consisting of 1 to 6 carbon atoms;

X=hydrogen or halogen;

W=hydrogen, nitro, amino, alkyl amino, halo-substituted alkyl, or halogen;

B=N, O, S, C, CH, $CH_2$;

C=N, O, S, C, CH, $CH_2$.

6. The method of claim 5, wherein said determining comprises measuring growth inhibition of cancer cells.

7. The method of claim 5, wherein the quinobenzoxazine derivative has the formula:

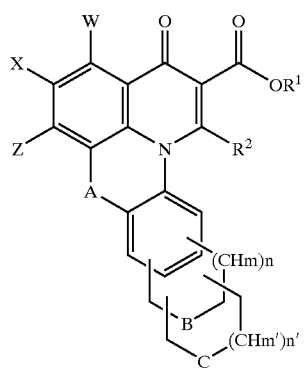

or a pharmaceutically acceptable salt, ester, or amide thereof.

8. The method of claim 5, wherein the quinobenzoxazine derivative has the formula:

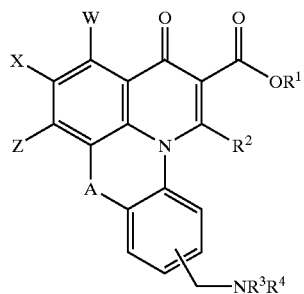

or a pharmaceutically acceptable salt, ester, or amide thereof.

9. A quinobenzoxazine substituted at the isolated benzyl group with an aromatic moiety, and having the dual mechanism of action of (i) stabilization of topoisomerase II-DNA complexes and (ii) interaction with G-quadruplexes.

10. A method of synthesizing quinobenzoxazines comprising the steps:

binding a carboxyacetophenone to a solid support through transesterification to form a solid bound ester;

generating an enaminoketoester from the solid bound ester;

forming a tetracyclic scaffold from the solid bound enaminoketoester;

adding a nitrogen-containing base to the enaminoketoester to form the solid bound quinobenzoxazine; and coupling the solid bound quinobenzoxazine with a compound selected from the group consisting of alkylating agent, acylating agent, amino acid and peptide, thereby producing a quinobenzoxazine.

11. A compound of the formula:

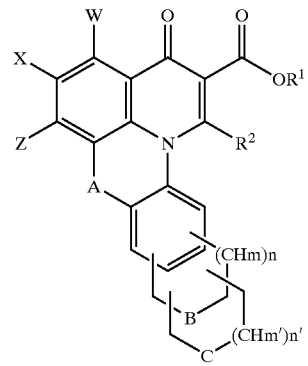

or a pharmaceutically acceptable salt, ester, or amide thereof, in which m=0, 1, 2;
m'=0, 1, 2;
n=0, 1, 2;
n'=0, 1, 2;
B=N, O, S, C, CH, $CH_2$;
C=N, O, S, C, CH, $CH_2$;
$R^1$=hydrogen or carboxy-protecting group;
$R^2$=hydrogen, halogen, or alkyl consisting of 1 to 6 carbon atoms;
A=oxygen, sulfur, or carbon;
Z=a halogen or nitrogen-containing group consisting of 1 to 6 carbon atoms;
X=hydrogen or halogen;
W=hydrogen, nitro, amino, alkyl amino, halo-substituted alkyl, or halogen.

12. The method of claim 1, wherein said quinobenzoxazine derivative has the formula of claim 11.

13. A compound of the formula:

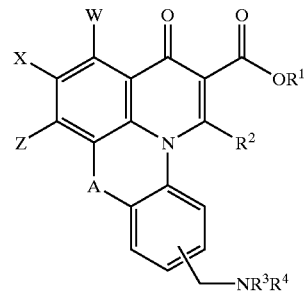

or a pharmaceutically acceptable salt, ester, or amide thereof, in which $R^1$=hydrogen or carboxy-protecting group
$R^2$=hydrogen, halogen, or alkyl consisting of 1 to 6 carbon atoms
$R^3$ or $R^4$=alkyl, acyl, amino acids, short peptides, or DNA alkylating, groove binding, intercalating functionalities, or any ligand for nuclear receptors
A=oxygen, sulfur, or carbon
Z=a halogen or nitrogen-containing group consisting of 1 to 6 carbon atoms
X=hydrogen or halogen
W=hydrogen, nitro, amino, alkyl amino, halo-substituted alkyl, or halogen.

14. A method of inhibiting proliferation of a neoplastic cell comprising contacting said cells with a quinobenzoxazine derivative that intercalates with DNA, whereby said quinobenzoxazine derivative intercalates with DNA and inhibits proliferation of said cell, and wherein said quinobenzoxazine derivative has a formula:

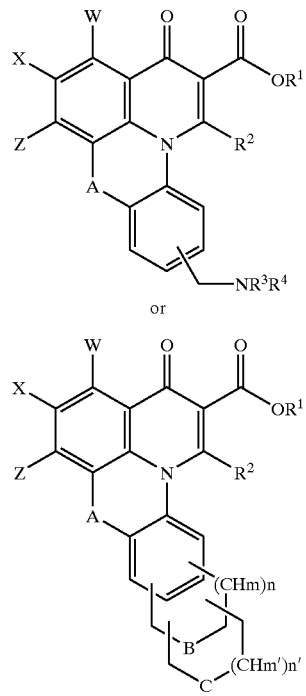

or a pharmaceutically acceptable salt, ester, or amide thereof, in which m=0, 1, 2;
m'=0, 1, 2;
n 0, 1, 2;
n'=0, 1, 2;
$R^1$=hydrogen or carboxy-protecting group;
$R^2$=hydrogen, halogen, or alkyl consisting of 1 to 6 carbon atoms;
$R^3$ or $R^4$=alkyl, acyl, amino acids, short peptides, or DNA alkylating, groove binding, intercalating functionalities, or any ligand for nuclear receptors;
A=oxygen, sulfur, or carbon;
Z=a halogen or nitrogen-containing group consisting of 1 to 6 carbon atoms;
X=hydrogen or halogen;
W=hydrogen, nitro, amino, alkyl amino, halo-substituted alkyl, or halogen;
B=N, O, S, C, CH, $CH_2$;
C=N, O, S, C, CH, $CH_2$.

15. The method of claim 14, wherein said quinobenzoxazine derivative has the formula of claim 11.

16. The method of claim 14, wherein said quinobenzoxazine has the formula of:

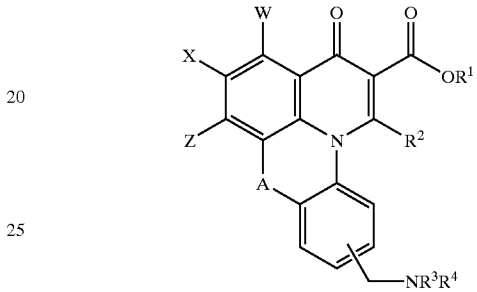

or a pharmaceutically acceptable salt, ester, or amide thereof.

17. The method of claim 14, wherein said cell is a benign neoplastic cell.

18. The method of claim 14, wherein said cell is a malignant neoplastic cell.

19. The method of claim 18, wherein said malignant cell is a breast cancer cell, a prostate cancer cell, liver cancer cell, a pancreatic cancer cell, a lung cancer cell, a brain cancer cell, an ovarian cancer cell, a testicular cancer cell, a skin cancer cell, a leukemia cell, a head and neck cancer cell, an esophageal cancer cell, a stomach cancer cell, a colon cancer cell, a retinal cancer cell, a bladder cancer cell, an anal cancer cell and a rectal cancer cell.

20. The method of claim 14, wherein said cell is located in a human subject.

* * * * *

UNITED STATES PATENT AND TRADEMARK OFFICE
CERTIFICATE OF CORRECTION

PATENT NO.   : 6,528,517 B1  Page 1 of 1
DATED        : March 4, 2003
INVENTOR(S)  : Hurley et al.

It is certified that error appears in the above-identified patent and that said Letters Patent is hereby corrected as shown below:

<u>Column 41,</u>
Line 63, please delete "a" and insert -- as -- therefor.

<u>Column 45,</u>
Line 40, after "n" please insert -- = -- therefor.

Signed and Sealed this

Nineteenth Day of August, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,528,517 B1
APPLICATION NO. : 09/245019
DATED : March 4, 2003
INVENTOR(S) : Laurence H. Hurley et al.

It is certified that error appears in the above-identified patent and that said Letters Patent is hereby corrected as shown below:

In column 1, lines 9-11, delete
"The government may have rights in the present invention pursuant to grant number CA-49751 from the National Cancer Institute" and insert
--This invention was made with government support under grant number CA049751 awarded by the National Institutes of Health. The government has certain rights in the invention.-- therefor.

Signed and Sealed this

Twenty-second Day of December, 2009

David J. Kappos
*Director of the United States Patent and Trademark Office*